US011696950B2

(12) United States Patent
Cui et al.

(10) Patent No.: US 11,696,950 B2
(45) Date of Patent: Jul. 11, 2023

(54) DRY SOLID ALUMINUM ADJUVANT-CONTAINING VACCINES AND RELATED METHODS THEREOF

(71) Applicant: BOARD OF REGENTS, THE UNIVERSITY OF TEXAS SYSTEM, Austin, TX (US)

(72) Inventors: Zhengrong Cui, Austin, TX (US); Robert O. Williams, III, Austin, TX (US); Xinran Li, Waltham, MA (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/156,511

(22) Filed: Oct. 10, 2018

(65) Prior Publication Data

US 2019/0142936 A1 May 16, 2019

Related U.S. Application Data

(60) Division of application No. 14/941,323, filed on Nov. 13, 2015, now abandoned, which is a continuation of application No. PCT/US2014/038475, filed on May 16, 2014.

(60) Provisional application No. 61/824,181, filed on May 16, 2013.

(51) Int. Cl.
| | | |
|---|---|---|
| *A61K 39/395* | (2006.01) | |
| *A61K 39/39* | (2006.01) | |
| *A61K 39/08* | (2006.01) | |
| *A61K 9/14* | (2006.01) | |
| *A61K 39/00* | (2006.01) | |

(52) U.S. Cl.
CPC ............ *A61K 39/39* (2013.01); *A61K 9/14* (2013.01); *A61K 39/0005* (2013.01); *A61K 39/08* (2013.01); *A61K 2039/55505* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,714,374 A | 2/1998 | Arnold et al. | |
| 6,284,282 B1 | 9/2001 | Maa et al. | |
| 6,585,957 B1 | 7/2003 | Adjei et al. | |
| 6,655,381 B2 | 12/2003 | Keane et al. | |
| 7,011,818 B2 | 3/2006 | Staniforth | |
| 7,229,645 B2 | 6/2007 | Maa et al. | |
| 7,306,787 B2 | 12/2007 | Tarara et al. | |
| 8,968,786 B2 | 2/2015 | Johnston et al. | |
| 9,044,391 B2 | 5/2015 | Williams et al. | |
| 9,061,027 B2 | 6/2015 | Hitt et al. | |
| 9,175,906 B2 | 10/2015 | Scherzer et al. | |
| 9,622,974 B2 | 4/2017 | Johnston et al. | |
| 10,092,512 B2 | 10/2018 | Johnston et al. | |
| 10,434,062 B2 | 10/2019 | Johnston et al. | |
| 2003/0064029 A1 | 4/2003 | Tarara et al. | |
| 2003/0090715 A1 | 5/2003 | Yoshikawa | |
| 2003/0232020 A1 | 12/2003 | York et al. | |
| 2004/0105821 A1 | 6/2004 | Bernstein et al. | |
| 2004/0137070 A1 | 7/2004 | Scherzer et al. | |
| 2004/0176391 A1 | 9/2004 | Weers et al. | |
| 2007/0287675 A1 | 12/2007 | Hitt et al. | |
| 2008/0118442 A1 | 5/2008 | Mohsen et al. | |
| 2009/0208582 A1 | 8/2009 | Johnston et al. | |
| 2010/0158951 A1* | 6/2010 | Randolph | A61K 9/19 424/278.1 |
| 2010/0221343 A1 | 9/2010 | Johnston et al. | |
| 2018/0147161 A1 | 5/2018 | Williams et al. | |
| 2019/0142936 A1 | 5/2019 | Cui et al. | |
| 2021/0170019 A1 | 6/2021 | Cui et al. | |
| 2021/0338671 A1 | 11/2021 | Williams et al. | |

FOREIGN PATENT DOCUMENTS

| | | |
|---|---|---|
| WO | WO 2003/090715 | 11/2003 |
| WO | WO 2005/025506 | 3/2005 |
| WO | WO 2006/026502 | 3/2006 |
| WO | WO 2008/118691 A2 | 10/2008 |
| WO | WO 2008/118691 A3 | 10/2008 |
| WO | WO 2009/103035 | 8/2009 |
| WO | WO 2011/129120 A1 | 4/2011 |
| WO | WO 2011/151760 A2 | 5/2011 |
| WO | WO 2011/151760 A3 | 5/2011 |

OTHER PUBLICATIONS

Braun, L.J. (Mar. 27, 2012). Interactions between antigen and adjuvant: Implications for formulation, 34 pages.
Buitink, Julia, et al. "High critical temperature above Tg may contribute to the stability of biological systems." *Biophysical Journal* 79.2 (2000): 1119-1128.
Chen, D., el al. "Thermostable formulations of a hepatitis B vaccine and a meningitis A polysaccharide conjugate vaccine produced by a spray drying method." *Vaccine* 28.31 (2010): 5093-5099.
Chen, Dexiang, and Debra Kristensen. "Opportunities and challenges of developing thermostable vaccines." *Expert Review of Vaccines* 8.5 (2009): 547-557.
Clausi, Amber L., et al. "Influence of protein conformation and adjuvant aggregation on the effectiveness of aluminum hydroxide adjuvant in a model alkaline phosphatase vaccine." *Journal of Phatmaceutical Sciences* 98.1 (2009): 114-121.
Clausi, Amber L., et al. "Inhibition of aggregation of aluminum hydroxide adjuvant during freezing and drying." *Journal of Pharmaceutical Sciences* 97.6 (2008): 2049-2061.

(Continued)

*Primary Examiner* — Yunsoo Kim
(74) *Attorney, Agent, or Firm* — Parker Highlander PLLC

(57) ABSTRACT

Described herein are dry vaccine compositions and methods of freezing aluminum-containing vaccines such that when converted into a dried powder, the dry vaccine can be readily reconstituted to form a stable liquid vaccine without significant loss of activity.

19 Claims, 32 Drawing Sheets

(56) References Cited

OTHER PUBLICATIONS

Clausi, Amber, et al. "Influence of particle size and antigen binding on effectiveness of aluminum salt adjuvants in a model lysozyme vaccine." *Journal of Pharmaceutical Sciences* 97.12 (2008): 5252-5262.

Crowe, Lois M., David S. Reid, and John H. Crowe. "Is trehalose special for preserving dry biomaterials?." *Biophysical Journal* 71.4 (1996): 2087-2093.

Diminsky, Dvorah, et al. "Physical, chemical and immunological stability of CHO-derived hepatitis B surface antigen (HBsAg) particles." *Vaccine* 18.1-2 (1999): 3-17.

Eisenbarth, Stephanie C., et al. "Crucial role for the Nalp3 inflammasome in the immunostimulatory properties of aluminium adjuvants." *Nature* 453.7198 (2008): 1122.

Engstrom, Joshua D., et al. "Formation of stable subimcron protein particles by thin film freezing." *Pharmaceutical Research* 25.6 (2008): 1334-1346.

Franchi, Luigi, and Gabriel Núñez. "The Nlrp3 inflammnasome is critical for aluminium hydroxide-mediated IL-1β secretion but dispensable for adjuvant activity." *European Journal of Immunology* 38.8 (2008): 2085-2089.

Hem, Stanley L., and Harm HogenEsch. "Relationship between physical and chemical properties of aluminum-containing adjuvants and immunopotentiation," *Expert Review of Vaccines* 6.5 (2007): 685-698.

Hornung, Veit, et al. "Silica crystals and aluminum salts activate the NALP3 inflammasome through phagosomal destabilization." *Nature Immunology* 9.8 (2008): 847.

International Search report dated Dec. 5, 2014, for PCT Application No. PCT/US2014/038475, filed on May 16, 2014, 4 pages.

Jiang, G. E., et al. "Anthrax vaccine powder formulations for nasal mucosal delivery." *Journal of Pharmaceutical Sciences* 95.1 (2006): 80-96.

Kinsinger, Linda S., et al. "Chemoprevention of breast cancer: a summary of the evidence for the US Preventive Servicess Task Force." *Annals of internal medicine* 137.1 (2002): 59-69.

Kool, Mirjam, et al. "Cutting edge: alum adjuvant stimulates inflammatory dendritic cells through activation of the NALP3 inflammasome." *The Journal of Immunology* 181.6 (2008): 3755-3759.

Leach, W. Thomas, et al. "Uniform encapsulation of stable protein nanoparticles produced by spray freezing for the reduction of burst release." *Journal of Pharmaceutical Sciences* 94.1 (2005): 56-69.

Maa, Yuh-Fun, et al. "Stabilization of alum-adjuvanted vaccine dry powder formulations: mechanism and application." *Journal of pharmaceutical sciences* 92.2 (2003): 319-332.

Méndez, Ilia Z. Romero, et al. "Potentiation of the immune response to non-adsorbed antigens by aiuminum-containing adjuvants." *Vaccine* 25.5 (2007): 825-833.

Overhoff, K. A., et al. "Use of thin film freezing to enable drug delivery: a review." *Journal of Drug Delivery Science and Technology* 19.2 (2009): 89-98.

Seeber, Sally J., Joe L. White, and Stanley L. Hem. "Predicting the adsorption of proteins by aluminium-containing adjuvants." *Vaccine* 9.3 (1991): 201-203.

Shi, Yi, Harm HogenEsch, and Stanley L. Hem. "Change in the degree of adsorption of proteins by aluminum-containing adjuvants following exposure to interstitial fluid: freshly prepared and aged model vaccines." *Vaccine* 20.1-2 (2001): 80-85.

Sloat, Brian R., et al. "Strong antibody responses induced by protein antigens conjugated onto the surface of lecithin-based nanoparticles." *Journal of Controlled Release* 141.1 (2010): 93-100.

Tritto, Elaine, Flaviana Mosca, and Ennio De Gregorio. "Mechanism of action of licensed vaccine adjuvants." *Vaccine* 27.25-26 (2009): 3331-3334.

Vaccine Excipient & Media Summary, downloaded Mar. 2017 from Centers for Disease Control and Prevention, National Center for Emerging and Zoonotic Infectious Diseases (NCEZID), Division of Healthcare Quality Promotion (DHQP); www.cdc.gov/vaccines/pubs/pinkbook/downloads/appendices/b/excipient-table-2.pdf.

Violette, Philippe D., and Fred Saad. "Chemoprevention of prostate cancer: myths and realities." *The Journal of the American Board of Family Medicine* 25.1 (2012): 111-119.

Wang, Wei. "Lyophilization and development of solid protein pharmaceuticals." *International Journal of Pharmaceutics* 203.1-2 (2000): 1 -60.

Watts, Alan B., et al. "Respirable low-density microparticles formed in situ from aerosolized brittle matrices." *Pharmaceutical Research* 30.3 (2013): 813-825.

Wolff, Lena, et al. "Protection of aluminum hydroxide during lyophilisation as an adjuvant for freeze-dried vaccines." *Colloids and Surfaces A: Physicochemical and Engineering Aspects* 330.2-3 (2008): 116-126.

Written Opinion dated Dec. 5, 2014, for PCT Application No. PCT/US2014/038475, filed on May 16, 2014, 4 pages.

Zapata, Marv I., et al. "Mechanism of freeze-thaw instability of aluminum hydroxycarbonate and magnesium hydroxide gels." *Journal of Pharmaceutical Sciences* 73.1 (1984): 3-8.

Zhang, Meimei, et al. "Formulation and delivery of improved amorphous fenofibrate solid dispersions prepared by thin film freezing." *European Journal of Pharmaceutics and Biopharmaceutics* 82.3 (2012): 534-544.

Abramowitz, et al., "Welding Colloidal Crystals with Carbon Dioxide," Macromolecules (2004) 37:7316-7324.

Adler, et al., "Stability and Surface Activity of Lactate Dehydrogenase in Spray-Dried Trehalose," Journal of Pharmaceutical Sciences (1999) 88(2):199-208.

Agu, et al., "The lung as a route for systemic delivery of therapeutic proteins and peptides," Respir Res (2001) 2:198-209.

Ashayer, et al., "Investigation of the molecular interactions in a pMDI formulation by atomic force microscopy," European Journal of Pharmaceutical Sciences (2004) 21:533-543.

Barro, et al., "Rotavirus NSP1 Inhibits Expression of Type I Interferon by Antagonizing the Function of Interferon Regulatory Factors IRF3, IRF5, and IRF7," Journal of Virology (2007) 81(9):4473-4481.

Benfait, "Kos reports achievement of new research and development milestones," Kos Press Release (2004).

Ben-Jebria, et al., "Large Porous Particles for Sustained Protection from Carbachol-Induced Bronchoconstricition in Guinea Pigs," Pharmaceutical Research (1999) 16(4):555-561.

Berlin, et al., "Densities of Several Proteins and L-Amino Acids in the Dry State," J_Phys. Chem. (1968) 72 (6):1887-1889.

Bevan, M.A., "An Approach to Low-Power, High-Performance, Fast Fourier Transform Processor Design," PhD Dissertation, Carnegie Mellon University, 1999, 186 pages.

Blondino, et al., "Surfactant Dissolution and Water Solubilization in Chlorine-Free Liquified Gas Propellants," Drug Dev. Ind. Pharm., 1998; 24:935-945.

Bodhmage, "Correlation between physical properties and flowability indicators for fine powders", M.S. Thesis, Cept. Chem. Eng., Univ. Saskatchewan, 2006.

Bower, C., et al., "Fractal Morphology of Drug Aggregates in Aerosol Propellant Suspensions," International Journal of Pharmaceutics, (1995), 118:229-235.

Carpenter, et al., "Rational Design of Stable Lyophilized Protein Formulations: Theory and Practice," in: J.F. Carpenter, M.C. Manning (Eds), Pharmaceutical Biotechnology_ 13. Rational Design of Stable Protein Formulations, Kluwer Academic/Plenum Press, New York, 2002, pp. 109-133.

Chow, et al., "Particle Engineering for Pulmonary Drug Delivery," Pharmaceutical Research (2007) 24(3):411-437.

Codrons, et al., "Systemic Delivery of Parathyroid Hormone (1-34) Using Inhalation Dry Powders in Rats," Journal of Pharmaceutical Sciences (2003) 92(5):938-950.

Costantino, et al., "Protein Spray-Freeze Drying. Effect of Atomization Conditions on Particle Size and Stability," Pharmaceutical Research (2000) 17(11):1374-1383.

Courrier, et al., "Pulmonary Drug Delivery Systems: Recent Developments and Prospects," Crit. Rev. Therapeutic Drug Carrier Systems, 2002; 19(4&5):425-498.

(56) References Cited

OTHER PUBLICATIONS

De Boer, A. H., et al. "Characterization of inhalation aerosols: a critical evaluation of cascade impactor analysis and laser diffraction technique." *International journal of pharmaceutics* 249.1-2 (2002): 219-231.
Dellamary, et al., "Hollow Porous Particles in Metered Dose Inhalers," Pharmaceutical Research (2000) 17 (2):168-174.
Edwards, et al., "Large Porous Particles for Pulmonary Drug Delivery," Science (1997) 276:1868-1871.
Engstrom, et al., "Formation of Stable Submicron Protein Particles by Thin Film Freezing," Pharmaceutical Research (2008) 25(6):1334-1346.
Engstrom, et al., "Morphology of protein particles produced by spray freezing of concentrated solutions," European Journal of Pharmaceutics and Biopharmaceutics (2007) 65:149-162.
Engstrom, et al., "Stable high surface area lactate dehydrogenase particles produced by spray freezing into liquid nitrogen," European Journal of Pharmaceutics and Biopharmaceutics (2007) 65:163-174.
Engstrom, J.D., et al., "Templated Open Flocs of Nanorods for Enhanced Pulmonary Delivery with Pressurized Metered Dose Inhalers," Pharmaceutical Research, (2009), 26:101-117.
Farahnaky, et al., "Enthalpy Relaxation of Bovine Serum Albumin and Implications for its Storage in the Glassy State," Biopolymers (2005) 78:69-77.
Fargues, et al., "Structural characterization of flocs in relation to their settling performances," Chemical Engineering Research and Design 81(A9):1171-1178.
Fargues, et al., "Structural characterization of flocs in relation to their settling performances," (Erratum), Chemical Engineering Research and Design 81(A9):1171-1178.
French, et al., "THe influence of formulation on emission, deaggregation and deposition of dry powders for inhalation," J_ Aerosol Sci. (1996) 27(5):769-783.
Garcia-Contreras, L., et al., "Liquid-Spray or Dry-Powder Systems for Inhaled Delivery of Peptide and Proteins?" Am. J_ Drug Delivery, (2005), 3:29-45.
Gonda, I, "Development of a Systematic Theory of Suspension Inhalation Aerosols. I. A Framework to Study the Effects of Aggregation on the Aerodynamic Behaviour of Drug Particles," Int. J_ Pharm., 1985; 27:99-116.
Goodarz-Nia, et al., "Floc Simulation. Effects of Particle Size and Shape," Chem. Eng. Sci., 1975; 30:407-12.
Heyder, et al., "Deposition of Particles in the Human Respiratory Tract in the Size Range 0.005-15 mm," J_ Aerosol Sci., 1986; 17(5):811-825.
Hilfiker, et al. "Polymorphism in the Pharmaceutical Industry" Wiley-VCH Verlag GmbH & Co., 2006; pp. 1-19 (2006).
Johnson, KA, "Interfacial Phenomena and Phase Behavior in Metered Dose Inhaler Formulations," in: A.J. Hickey (Ed), Inhalation Aerosols: Physical and Biological Basis for Therapy, 2007.
Keller, "Innovations and perspectives of metered dose inhalers in pulmonary drug delivery," International Journal of Pharmaceutics (1999) 186:81-90.
Kim, et al., "Determination of Water in Pressurized Pharmaceutical Metered Dose Aerosol Products," Drug Dev. And Ind. Pharm., 1992; 18(20):2185-95.
Kwon, et al., "Long acting porous microparticle for pulmonary protein delivery," International Journal of Pharmaceutics (2007) 333:5-9.
Labiris, N. R.. and M. B. Dolovich. "Pulmonary drug delivery. Part I: physiological factors affecting therapeutic effectiveness of aerosolized medications." *British journal of clinical pharmacology* 56.6 (2003): 588-599.
Lechuga-Ballesteros, et al., "Trileucine Improves Aerosol Performance and Stability of Spray-Dried Powders for Inhalation," Journal of Pharmaceutical Sciences (2008) 97(1 ):287-302.
Li, et al., "Aerodynamics and aerosol particle deaggregation phenomena in model oral-pharyngeal cavities," J_ Aerosol Sci. (1996) 27(8): 1269-1286.
Liao, et al., "The effects of polyvinyl alcohol in the in vitro stability and delivery of spray-dried protein particles from surfactant-free HFA 134a-based pressurized metered dose inhalers," International Journal of Pharmaceutics (2005) 304:29-39.
Maa, et al., "Biopharmaceutical Powders: Particle Formation and Formulation Considerations," Curr. Pharm. Biotechnol., 2000; 1(3):283-302.
Maa, et al., "Protein inhalation powders: spray drying vs spray freeze drying," Pharmaceutical Research (1999) 16 (2):249-254.
Maa, et al., Spray freeze-drying of biopharmaceuticals: applications and stability considerations, in: H.R. Costantino, M.J. Pikal (Eds), Biotechnology: Pharmaceutical Aspects. 2. Lyophilization of Biopharmaceuticals, A Merican Association of Pharmaceutical Scientists, Arlington, 2004, pp. 519-561.
Merriam-Webster Online: medical dictionary definitions: atomize, compact, floc, flocculate, flocculent, porous, template. Accessed at http://www.merriam-webster.com/on May 19, 2012.
Nail, et al., "Fundamentals of Freeze-Drying," in: S.L. Nail, M.J. Akers (Eds), Pharmaceutical Biotechnology_ 14. Development and Manufacture of Protein Pharmaceuticals, Kluwer Academic/Plenum Publishers, New York, 2002, pp. 281-360.
Nguyen, et al., "Protein Powders for Encapsulation: A comparison of Spray-Freeze Drying and Spray Drying of Darbepoetin Alfa," Pharmaceutical Research (2004) 21(3):507-514.
Office Communication issued in U.S. Appl. No. 12/778,795, dated Apr. 11, 2017.
Office Communication issued in U.S. Appl. No. 16/115,888, dated Feb. 14, 2019.
Oliver, et al., "Initial Assessment of a Protein Formulated in Pressurized Metered Dose Inhalers for Pulmonary Delivery," Respiratory Drug Delivery VII, 2000.
Patton, J.S., et al., "Inhaling Medicines: Delivering Drugs to the Body Through the Lungs," Nature Rev Drug Discovery, (2007), 6:67-74.
PCT/US2009/034162—PCT Search Report & Written Opinion of the International Searching Authority, dated Sep. 22, 2009.
Peguin, et al., "Microscopic and Thermodynamic Properties of the HFA134a-Water Interface: Atomistic Computer Simulations and Tensiometry under Pressure," Langmuir (2006) 22:8826-8830.
Philipse, "The Random Contact Equation and its Implications for (Colloidal) Rods in Packings, Suspensions, and Anisotropic Powders," Langmuir (1996) 12:1127-1133.
Philipse, AP, "The Random Contact Equation and Its Implications for (Colloidal) Rods in Packings, Suspensions, and Anisotropic Powders," (Additions and Corrections), Langmuir, 1996; 12:5971.
Philipse, et al., "On the Density and Structure Formation in Gels and Clusters of Colloidal Rods and Fibers," Langmuir (1998) 14:49-54.
Quinn, et al., "Protein conformational stability in the hydrofluoroalkane propellants tetrafluoroethane and heptafluoropropane analysed by Fourier transform Raman Spectroscopy," International Journal of Pharmaceutics (1999) 186:31-41.
Rogers, et al., "A novel particle engineering technology to enhance dissolution of poorly water soluble drugs: spray'freezing into liquid," European Journal of Pharmaceutics and Biopharmaceutics (2002) 54:271-280.
Rogers, et al., "Micronized powders of a poorly water soluble drug produced by a spray-freezing into liquid-emulsion process," European Journal of Pharmaceutics and Biopharmaceutics (2003) 55:161-172.
Rogueda, "HPFP, a Model Propellant for pMD1s," Drug Development and Industrial Pharmacy (2003) 29(1):39-49.
Rogueda, "Novel hydrofluoroalkane suspension formulations for respiratory drug delivery," Expert Opinion Drug Del. (2005) 2:625-63 8.
Sakagami. "In vivo, in vitro and ex vivo models to assess pulmonary absorption and disposition of inhaled therapeutics for systemic delivery." *Advanced drug delivery review* 58.9-10 (2006): 1030-1060.
Shekunov, et al., "Particle size analysis in pharmaceutics: principles, methods and applications," Pharmaceutical Research (2007) 24(2):203-227.

(56) References Cited

OTHER PUBLICATIONS

Shoyele, et al., "Prospects of formulating proteins/peptides as aerosols for pulmonary drug delivery," International Journal of Pharmaceutics (2006) 314:1-8.
Sigma Aldrich catalog entry: itraconazole. Accessed on Oct. 11, 2011 at <http://www.sigmaaldrich.com/catalog/Lookup.do?N3=mode+matchpartialmax&N4-itraconacole&D7=0&D10=itraconazole&N1=S_ID&ST=RS&N25=O&F=PR>.
Smith, et al., "Electrostatically Stabilized Metal Oxide Particle Dispersions in Carbon Dioxide," J_ Phys. Chem. B (2005) 109:20155-20165.
Smyth, et al., "Aerosol Generation from Propellant-Driven Metered Dose Inhalers," in: J_ Hickey Anthony (Ed), Inhalation Aerosols: Physical and Biological Basis for Therapy, 2007, pp. 399-416.
Steckel, et al., "In vitro evaluation of dry powder inhalers I: drug depostition of commonly used devices," International Journal of Pharmaceutics (1997) 154:19-29.
Stein, S.W., et al., "The Relative Influence of Atomization and Evaporation on Metered Dose Inhaler Drug Delivery Efficiency," Aerosol Science and Technology, (2006), 40:335-347.
Tadmor, "The London-van der Waals interaction energy between objects of various geometries," J_ Phys.: Condens. Matter(2001) 13:L195-L202.
Takashima, et al., "A Study of Proton Fluctuation in Protein. Experimental Study of the Kirkwood-Shumaker Theory," The Journal of Physical Chemistry (1965) 69(7):2281-2286.
Tam, et al., "Amorphous Cyclosporin Nanodispersions for Enhanced Pulmonary Deposition and Dissolution," Journal of Pharmaceutical Sciences (2008) 97(11 ):4915-4933.
Tang, et al., "A Model to Describe the Settling Behavior of Fractal Aggregates," Journal of Colloid and Interface Science (2002) 247:210-219.
Traini, et al., "In Vitro Investigation of Drug Particulates Interactions and Aerosol Performance of Pressurised Metered Dose Inhalers," Pharmaceutical Research (2007) 21 (1):125-135.
Traini, et al., "Surface Energy and Interparticle Force Correlation in Model pMDI Formulations," Pharmaceutical Research, (2005) 22(5):816-825.
Traini, et al., "The Use of AFM and Surface Energy Measurements to Investigate Drug-Canister Material Interactions in a Model Pressurized Metered Dose Inhaler Formulation," Aerosol Science and Technology (2006) 40:227-236.
Tsapis, et al., "Trojan particles: Large Porous Carriers of Nanoparticles for Drug Delivery," PNAS (2002) 99 (19):12001-12005.
Ulrich, DR, "Chemical Processing of Ceramics," Chem. Eng. News, 1990; 68:28-40.
US Pharmacopeia Ch. 1174: Powder Flow, 2004.
Vanbever, et al., "Formulation and Physical Characterization of Large Porous Particles for Inhalation," Pharmaceutical Research (1999) 16(11): 1735-1742.
Vervaet, et al., "Drug-surfactant-propellant interactions in HFA-formulations," International Journal of Pharmaceutics (1999) 186:13-30.
Watts, "Pulmonary Delivery of Tacrolimus for Lung Transplant and Asthma Therapy," Ph.D. Dissertation, The University of Texas at Austin, 2009.
Webb, et al., A New Mechansim for Decreasing Aggregation of Recombinant Human Interferon-γ by a Surfactant Slowed Dissolution of Lyophilized Formulations in a Solution Containing 0.03% Polysorbate 20.
Webb, et al., "Surface Adsorption of Recombinant Human Interferon-γ in Lyophilized and Spray-Lyophilized Formulations," Journal of Pharmaceutical Sciences (2002) 91(6):1474-1487.
White, et al., "EXUBERA: Pharmaceutical Development of a Novel Product for Pulmonary Delivery of Insulin," Diabetes Technology & Therapeutics (2005) 7:896-906.
Williams, et al., "Formulation of a protein with a propellant HFA 134a for aerosol delivery," European Journal of Pharmaceutical Sciences (1998) 7:137-144.
Williams, et al., "Influence of Metering Chamber vol. and Water Level on the Emitted Dose of a Suspension-Based pMDI Containing Propellant 134a," Pharmaceutical Research (1997) 14(4):438-443.
Williams, III, et al., "Influence of Propellant Composition on Drug Delivery from a Pressurized Metered-Dose Inhaler," Drug Dev. Ind. Pharm., 1998; 24(8):763-770.
Wu, et al., "Molecular Scale Behavior in Alternative Propellant-Based Inhaler Formulations," in: A.J. Hickey (Ed), Inhalation Aerosols: Physical and Biological Basis for Therapy, 2007.
Yu, et al., "Preparation and characterization of microparticles containing peptide produced by a novel process: spray freezing into liquid," European Journal of Pharmaceutics and Biopharmaceutics (2002) 54:221-228.
Yu, et al., "Spray freezing into liquid nitrogen for highly stable protein nanostructured microparticles," European Journal of Pharmaceutics and Biopharmaceutics (2004) 58:529-537.
Yu, et al., "Spray freezing into liquid versus spray-freeze drying: Influence of atomization on protein aggregation and biological activity," European Journal of Pharmaceutical Sciences (2006) 27:9-18.
Zhanpeng, J., et al., "Flocculation Morphology: Effect of Particulate shape and *Coagulant* Species on Flocculation," Water Sci Technol., (2006), 53:9-16.

\* cited by examiner

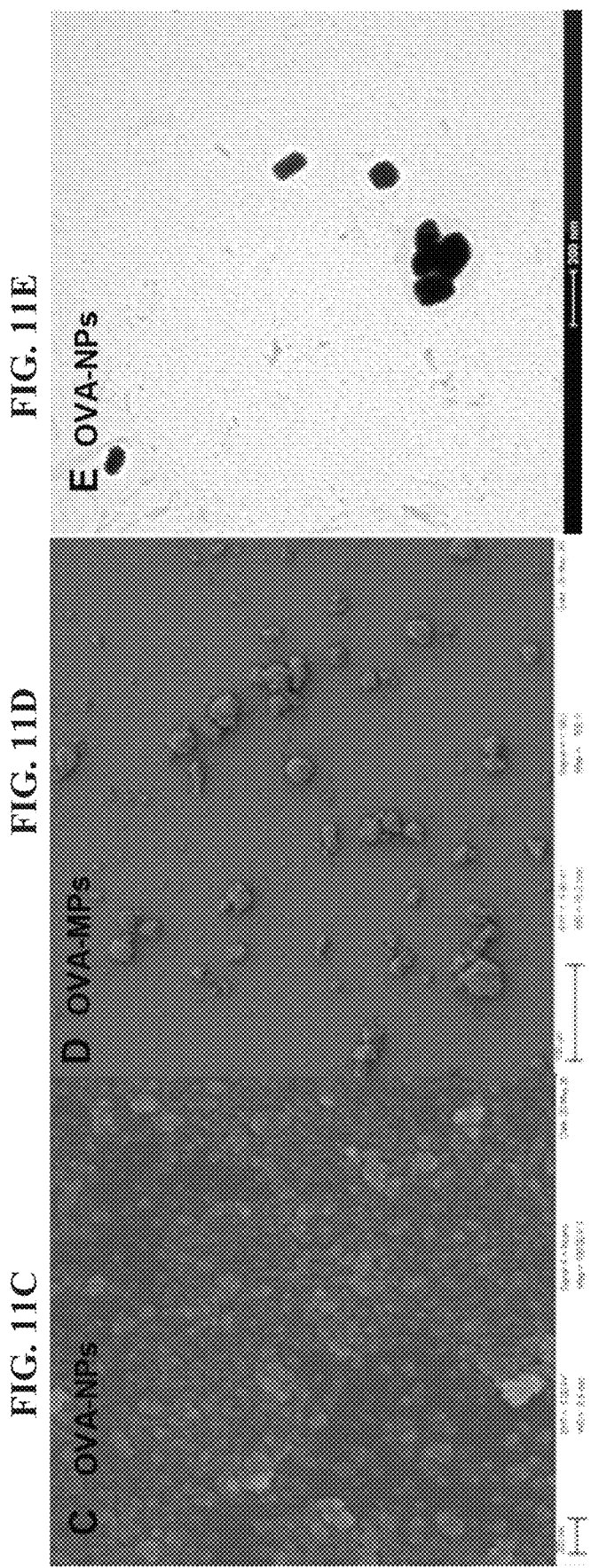

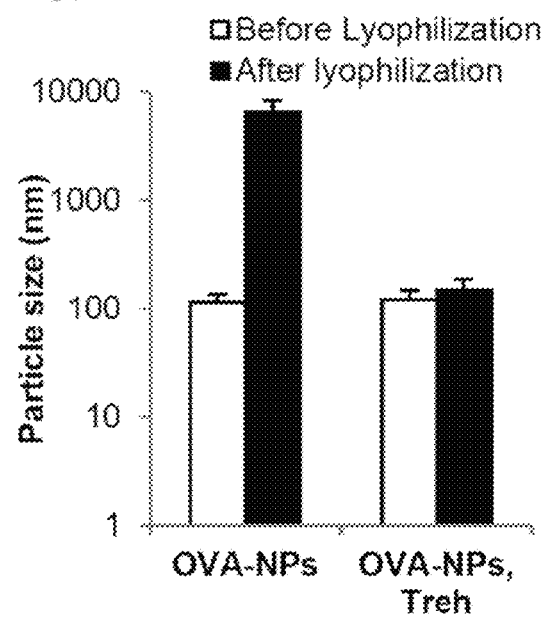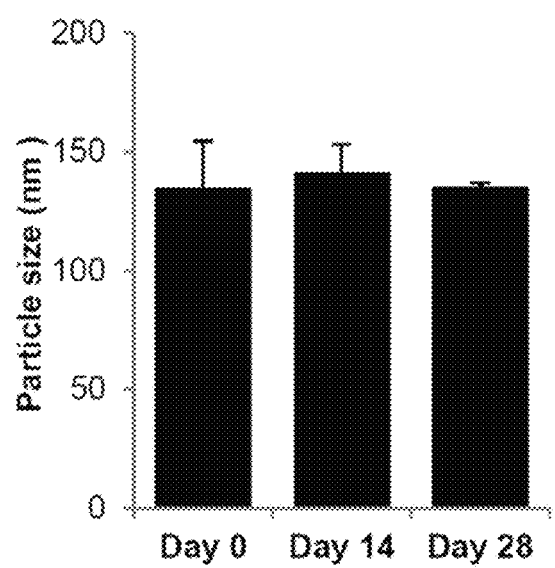
FIG. 12A
FIG. 12B

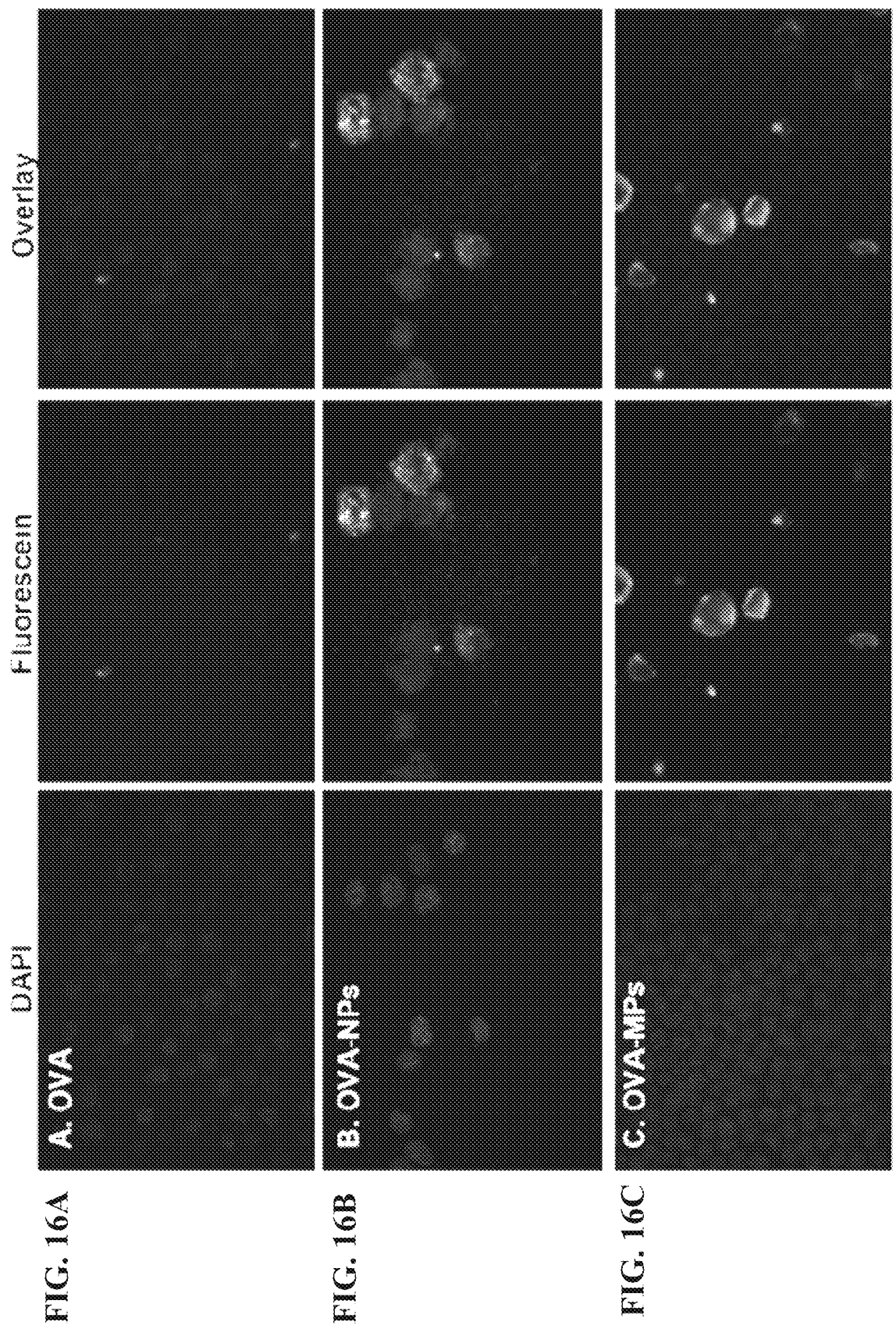

A. OVA/Al(OH)$_3$, fresh

B. OVA/Al(OH)$_3$, TFFD

C. OVA/Al(OH)$_3$, -20°C then drying

D. OVA/Al(OH)$_3$, -80°C then drying

A. TT, before TFFD

B. TT, after TFFD

E. Fresh TT, after freeze-thaw

F. Dry TT, after freeze-thaw

G. Engerix-B, before TFFD

H. Engerix-B, after TFFD

DRY SOLID ALUMINUM ADJUVANT-CONTAINING VACCINES AND RELATED METHODS THEREOF

CROSS-REFERENCES TO RELATED APPLICATIONS

This application is a continuation of U.S. patent application Ser. No. 14/941,323, filed Nov. 13, 2015, now abandoned, which is a national phase application under 35 U.S.C. § 371 of International Application No. PCT/US2014/038475, filed May 16, 2014, which claims the benefit of U.S. Provisional Patent Application No. 61/824,181, filed May 16, 2013, each of which are incorporated herein by reference in their entirety and for all purposes.

BACKGROUND OF THE INVENTION

The invention generally relates to vaccine compositions. More particularly, the invention relates to vaccine powders produced from aqueous vaccine compositions.

Aluminum-containing compounds such as aluminum hydroxide and aluminum phosphate have been used as human vaccine adjuvants for decades. Many currently commercially available vaccines, such as diphtheria-tetanus-pertussis vaccine, Hepatitis A vaccines, Hepatitis B vaccines, Pneumococcal conjugate vaccines, anthrax vaccines, and Rabies vaccines, contain aluminum-containing adjuvants. However, a major limiting factor with these vaccines is that they cannot be frozen (i.e., the vaccines must remain stored as a refrigerated liquid dispersion from manufacturing through to administration to patients), because freezing of the dispersion causes irreversible coagulation that damages the vaccines (e.g., loss in potency and stability). Aluminum-containing vaccines are formulated as liquid suspensions and are required to be kept refrigerated at 2-8° C. during transport and storage. Vaccines that have been inadvertently exposed to freezing conditions before being administered to patients must be discarded, causing significant product waste and limited utility. This is significant considering that this cold-chain storage alone accounts for up to 80% of the financial cost of vaccination, and complicating matters further, an estimated 75-100% of the vaccine shipments are actually exposed to freezing temperatures, resulting in costly waste and the loss of nearly half of all global vaccine supplies (WHO data). It is evident that having aluminum-containing vaccines in a solid form that can be easily reconstituted just prior to injection would be hugely beneficial to our health care system today. It is also evident that administration of the solid form of the aluminum-containing vaccines, without having to reconstitute into a liquid suspension, for example for administration by inhalation, would be hugely beneficial as well.

There are several main aluminum-containing adjuvants, aluminum hydroxide, aluminum phosphate, and aluminum potassium sulfate. Aluminum hydroxide adjuvant is composed of small primary fibers with an average calculated dimension of 4.5×2.2×10 nm, whereas the primary particles of aluminum phosphate adjuvant are around 50 nm. In solutions, however, the size of the primary particles of both aluminum hydroxide and aluminum phosphate becomes 1-20 µm as a result of aggregation. Aggregation is typically irreversible. Due to their favorable safety profile, aluminum-containing adjuvants have been widely used in human vaccines for decades. Recently, there had been extensive efforts in identifying the relationship between the size of particulate vaccine carriers and their adjuvant activities. Although it remains controversial as to what particle size is associated with the most potent adjuvant activity, it is clear now that the size of particulate vaccine carriers significantly affects their adjuvant activities.

Methods of making dry vaccines that retain particle size and immunogenicity upon reconstitution would be useful and would address the deficiencies that current exist in the field. Provided herein are methods and compositions addressing these and other needs in the art.

BRIEF SUMMARY OF THE INVENTION

In an aspect is provided a dry vaccine including an antigenic protein and an aluminum adjuvant, wherein at least 75% of the antigenic protein is adsorbed to the aluminum adjuvant.

In an aspect is provided a pharmaceutical composition including a pharmaceutically acceptable excipient and any of the compositions (e.g. vaccines) described herein (including embodiment).

In an aspect is provided a method for preparing a vaccine thin film including: applying a liquid vaccine to a freezing surface; allowing the liquid vaccine to disperse and freeze on the freezing surface thereby forming a vaccine thin film.

In an aspect is provided a method of treating a disease in a patient in need of such treatment, the method including administering a therapeutically effective amount of a solvated dry vaccine as described herein (e.g. in an aspect, embodiment, example, table, figure, or claims) (e.g. a reconstituted liquid vaccine as described herein) to the patient.

BRIEF DESCRIPTION OF THE DRAWINGS

FIG. 6A shows the images of OVA-adsorbed aluminum hydroxide particles lyophilized with different concentrations of trehalose. FIG. 6B shows the sizes of the reconstituted OVA-adsorbed aluminum hydroxide powders lyophilized with various concentrations of trehalose.

FIGS. 7A and 7B show photos of lyophilized OVA-adsorbed aluminum hydroxide and OVA-adsorbed aluminum phosphate using thin-film freezing, respectively. FIGS. 7C and 7D show microscopic images of lyophilized OVA-adsorbed aluminum hydroxide and OVA-adsorbed aluminum phosphate after reconstitution in water. Shown in insets in FIG. 7C and FIG. 7D are the particle sizing results from the laser diffraction instrument.

FIGS. 8A-B show the microscopic images of the physical mixture of OVA-adsorbed Alhydrogel and the OVA-adsorbed Alhydrogel dry powder after reconstitution, respectively.

FIG. 9A. Original vaccine. FIG. 9B. Vaccine after TFF with 2% trehalose. FIG. 9C. Vaccine after TFF with 3% trehalose.

FIG. 10A depicts the particle sizes (open bar) and zeta potentials (●) of aluminum hydroxide nanoparticles (NPs) and microparticles (MPs). FIG. 10B the aluminum hydroxide nanoparticles were stable when stored at 4° C. for a month, whereas the microparticles were slightly less stable. The X-ray powder patterns of aluminum hydroxide particles are presented in FIGS. 10C and 10D. FIG. 10C the nanoparticles were completely amorphous. FIG. 10D the microparticles were mostly crystalline $Al(OH)_3$, although the large peak in the left showed that some amorphous AlO(OH) materials existed as well.

FIG. 11A-E. FIG. 11A Sizes (open bar) and zeta potentials (●) of the aluminum hydroxide nanoparticles and microparticles after the adsorption of OVA protein at a 1:2 ratio (OVA vs. particle, w/w). FIG. 11B Fractions of free OVA when a fixed amount of OVA was mixed with an increasing amount of the aluminum hydroxide nanoparticles or microparticles. FIGS. 11C and 11D depict SEM pictures of OVA-adsorbed aluminum hydroxide nanoparticles (OVA-NPs) and OVA-adsorbed aluminum hydroxide microparticles (OVA-MPs). FIG. 11E depicts a TEM picture of OVA-NPs.

FIG. 12A-B. FIG. 12A The OVA-adsorbed aluminum hydroxide nanoparticles were successfully lyophilized with trehalose (2%) as a lyoprotectant. FIG. 12B In a short-term 28-day study, the size of the lyophilized, OVA-adsorbed aluminum hydroxide nanoparticles did not change when stored as a lyophilized powder at 4° C.

FIG. 13A The anti-OVA IgG level in mice that were immunized with the OVA-adsorbed aluminum hydroxide nanoparticles was significantly higher than that in mice that were immunized with OVA alone or OVA-adsorbed microparticles at 100-fold dilution. FIG. 13B. 31 days after tumor cell injection, tumors were detected only in one of the 5 mice that were immunized with the OVA-adsorbed aluminum hydroxide nanoparticles.

FIG. 14A, open bars The mean diameters of the resultant PA-adsorbed aluminum hydroxide nanoparticles and microparticles were 204±25 nm and 7.1±3.4 μm, respectively. FIG. 14B Mice were then immunized with the PA-adsorbed aluminum hydroxide nanoparticles or microparticles on days 0 and 14. One week after the first dose, anti-PA IgG was not detectable in any mice. One week after the second dose, significant anti-PA IgG responses were detected in mice that were immunized with the PA-adsorbed aluminum hydroxide nanoparticles or microparticles, although the levels of the anti-PA IgG response were not different. FIG. 14C However, 4 weeks after the second immunization, the anti-PA IgG levels in mice that were immunized with the PA-adsorbed aluminum hydroxide nanoparticles were significantly higher than that in mice that were immunized with the PA-adsorbed aluminum hydroxide microparticles. FIG. 14D Anti-PA IgG1 levels 4 weeks after the second immunization are shown. FIG. 14E The kinetics of the anti-PA IgG levels within 4 weeks is shown in. Significant higher anti-PA IgG1 level was detected in mice immunized with PA-adsorbed aluminum hydroxide nanoparticles as compared to in mice immunized with PA-adsorbed aluminum hydroxide microparticles. Anti-IgE level was not detected 4 weeks after immunization with PA-adsorbed aluminum hydroxide nanoparticles or microparticles.

FIG. 16A-C. Green fluorescence signal, an indication of the location of the OVA protein, was detected only inside cells that were incubated with OVA-adsorbed aluminum hydroxide nanoparticles, not in cells that were incubated with OVA-adsorbed aluminum hydroxide microparticles.

FIG. 18B is a representative image of the Engerix-B vaccine after reconstitution from the TFFD powder. The particle size of the Engerix-B after it was subjected to TFFD and reconstitution was 3.29±0.15 μm, and particle size of the fresh vaccine was 5.64±0.01 μm, as determined using a Sympatec Helos laser diffraction instrument (Sympatec GmbH, Germany) equipped with a R3 lens. Clearly, the human hepatitis B vaccine Engerix-B can be converted into a dry powder using the TFFD method.

FIG. 19A is a representative image of the fresh TT vaccine under a microscope. Shown in FIG. 19B is a representative image of the TT vaccine reconstituted from dry powder after the powder was subjected to three cycles of freezing-and-thawing. Shown in FIG. 19C is a representative image of the fresh TT vaccine after 3 cycles of freezing-and-thawing. Clearly, repeated freezing-and-thawing of the fresh TT vaccine caused significant aggregation, while the dry TT vaccine powder is not sensitive to freezing anymore.

FIG. 20A is a representative image of the fresh TT vaccine. Shown in FIG. 20B and FIG. 20C are representative images of the TT vaccine 0 and 6 days after reconstitution, respectively. The TT vaccine does not have to be used immediately after it is reconstituted from a dry powder.

In FIG. 22B-D, the method of freezing was TFF, shelf-freezing at –20° C., and shelf-freezing at –80° C., respectively.

FIG. 23A. Particle sizes of OVA-adsorbed aluminum hydroxide reconstituted from powders that were lyophilized using various concentrations of trehalose. FIG. 23B. Representative images of dried OVA-adsorbed aluminum hydroxide powders prepared with 1%, 2%, or 3% (w/v) trehalose.

FIG. 24A. The binding efficiency of OVA to aluminum hydroxide before and after TFFD (inset, OVA protein band in SDS-PAGE gel). FIG. 24B. DSC curves of OVA-adsorbed aluminum hydroxide dry powder, OVA, trehalose, and aluminum hydroxide alone. FIG. 24C. A representative SEM image OVA-adsorbed aluminum hydroxide dry powder. FIG. 24D. A representative SEM image of the freshly prepared OVA-adsorbed aluminum hydroxide.

FIG. 26A. A representative microscopic image of OVA-adsorbed aluminum phosphate. FIG. 26B-C Representative images of OVA-adsorbed Alhydrogel® reconstituted immediately after TFFD (FIG. 26B) or after 10 months of storage at room temperature (FIG. 26C), respectively.

FIG. 27A. A representative microscopic image of the original TT vaccine after dilution in 2% (w/v) of trehalose. FIG. 27B. A representative microscopy image of the TT vaccine after TFFD and reconstitution in a phosphate buffer. FIG. 27C. Intrinsic tryptophan fluorescence spectra of TT vaccine before and after TFFD. FIG. 27D. Anti-tetanus toxin IgG levels in serum samples of mice immunized with TT vaccine before and after TFFD. Female BALB/c mice (n=5) were s.c. injected with TT vaccine, before or after TFFD and reconstitution, on days 0, 14 and 28 with 3.75 Lf of tetanus toxoid per mouse per injection. Sterile PBS and original TT vaccine diluted in sterile PBS or 2% trehalose were used as controls. Total anti-tetanus toxin IgG levels in serum samples were measured 16 days after the third dose. FIG. 27E. A representative image of the fresh TT vaccine after 3 cycles of freeze-and-thaw. FIG. 27F. A representative images of TT vaccine reconstituted from dry powder after the powder was subjected to three cycles of freeze-and-thaw. FIG. 27G-H. Representative images of fresh Engerix-B vaccine (FIG. 27G) and Engerix-B after reconstitution from TFFD powder (FIG. 27H).

DETAILED DESCRIPTION

Figure 1A:
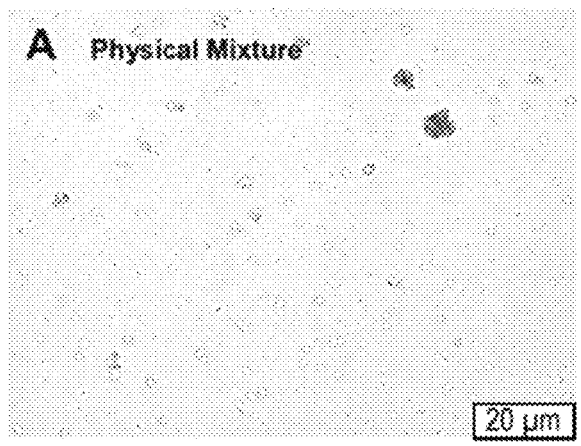
FIG. 1A-D. Microscopic images of OVA-adsorbed aluminum hydroxide particles before freeze-drying (FIG. 1A) and after high speed thin-film freeze-drying and reconstitution (FIG. 1B), slow freezing at −20° C., drying and reconstitution (FIG. 1C), and slow freezing at −80° C., drying and reconstitution (FIG. 1D).
Figure 1B:
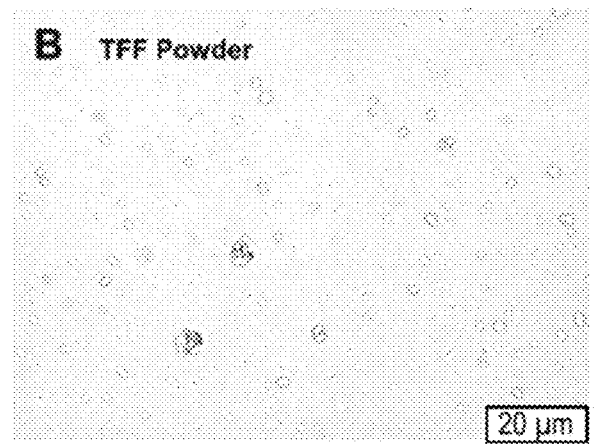
Figure 1C:
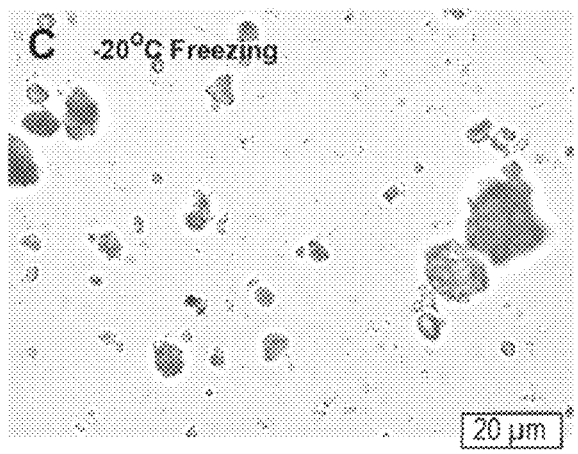
Figure 1D:
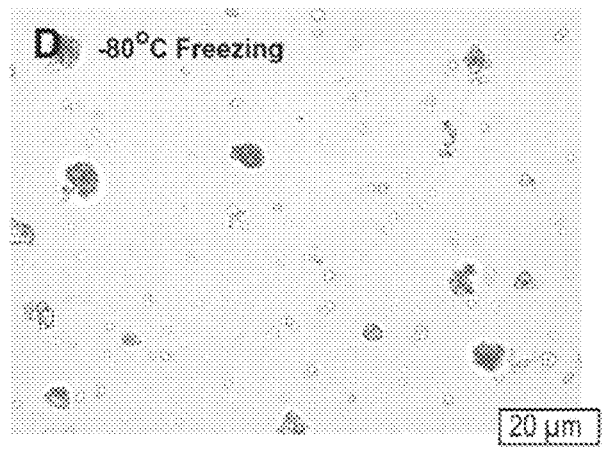

Described herein is a new method to freeze aluminum-containing vaccines with a very low percentage cryoprotectant(s) such that when converted into a dried powder, the solid can be readily reconstituted to form a stable dispersion without significant loss of stability or activity. The solid form of the vaccines may now be transported and stored in a wide range of temperatures without concern of accidental exposure to freezing conditions. In addition, the solid form of the vaccine may also be stored at room temperature, which will potentially decrease the costs of vaccines.

Some aluminum salts, such as aluminum hydroxide and aluminum phosphate, have been widely used as human vaccine adjuvants for decades. The primary particles of aluminum hydroxide and aluminum phosphate are in the nanometer-scale. However, when dispersed in an aqueous solution, the primary particles aggregate to form larger microparticles of 1-20 μm [S. L. Hem, H. Hogenesch, *Expert review of vaccines*, 6 (2007) 685-698; I. Z. Romero Mendez et al., *Vaccine*, 25 (2007) 825-833]. Thus, a vaccine that is prepared by mixing an antigen with an aluminum salt is physically a suspension of aluminum salt particles with antigens adsorbed on them. Three mechanisms are frequently cited to explain the mechanisms underlying the adjuvant activity of aluminum salts [I. Z. Romero Mendez et al., *Vaccine*, 25 (2007) 825-833; H. HogenEsch, *Vaccine*, 20 Suppl 3 (2002) S34-39; L. S. Jones et al., *The Journal of biological chemistry*, 280 (2005) 13406-13414; J. W. Mannhalter et al., *Clinical and experimental immunology*, 61 (1985) 143-151; M. Ulanova et al., *Infection and immunity*, 69 (2001) 1151-1159]: i) for decades, it was thought to be the depot effect. Aluminum salts form an antigen depot at the injection site, from where the antigens are slowly released [A. T. Glenny et al., *J. Pathol.Bacteriol*, 34 (1931) 267-275]; ii) Aluminum salts induce inflammation, thus recruiting and activating antigen-presenting cells that capture antigens [E. Tritto et al., *Vaccine*, 27 (2009) 3331-3334]; iii) The adsorption of soluble antigens on aluminum salt particles makes them readily taken up by antigen-presenting cells [E. Tritto et al., *Vaccine*, 27 (2009) 3331-3334]. Finally, recent data showed that the molecular target for the pro-inflammatory activity of aluminum salts is the NOD-like receptor protein 3 (NLRP3) (or NALP3) [E. Tritto et al., *Vaccine*, 27 (2009) 3331-3334; S. C. Eisenbarth et al., *Nature*, 453 (2008) 1122-1126; L. Franchi et al., *Eur J Immunol*, 38 (2008) 2085-2089; M. Kool et al., *Journal of immunology*, 181 (2008) 3755-3759; V. Hornung et al., *Nat Immunol*, 9 (2008) 847-856].

Thin-film freezing (TFF) has been recently studied in the biopharmaceutical field for preparing submicron protein particles [J. D. Engstrom et al., *Pharmaceutical research*, 25 (2008) 1334-1346]. In TFF process, a liquid (e.g., solution) is spread out on a cryogenic substrate to form a thin film in less than one second. The resultant frozen film is then dried by lyophilization. For example, Engstrom et al. produced dried protein powders with a diameter of 300 nm using TFF, and the enzyme activity of the proteins was fully preserved [J. D. Engstrom et al., *Pharmaceutical research*, 25 (2008) 1334-1346]. In the present study, the feasibility of freeze drying vaccines that are adjuvanted with aluminum salts using high speed TFF was tested. Ovalbumin (OVA) was initially used as a model protein antigen, and it was adsorbed onto aluminum hydroxide or aluminum phosphate and lyophilized after thin film freezing. In addition, a commecially availble veterinary tetanus toxoid vaccine (tetanus antitoxin concentrated/purified, Colorado Serum Company) and a human hepatitis B vaccine (Engerix-B, GlaxoSmithKline Biologics) were also prepared using the TFF method.

A. Definitions

The abbreviations used herein have their conventional meaning within the chemical and biological arts. Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions.

The terms "a" or "an," as used in herein means one or more. In addition, the phrase "substituted with a[n]," as used herein, means the specified group may be substituted with one or more of any or all of the named substituents.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat a disease associated with (e.g. caused by) an infectious agent (e.g. bacterium or virus). The term "treating" and conjugations thereof, include prevention of an injury, pathology, condition, or disease. The term "preventing" or "prevention" refers to any indicia of success in protecting a subject or patient (e.g. a subject or patient at risk of developing a disease or condition) from developing, contracting, or having a disease or condition (e.g. an infectious disease or diseases associated with an infectious agent), including preventing one or more symptoms of a disease or condition or diminishing the occurrence, severity, or duration of any symptoms of a disease or condition following administration of a prophylactic or preventative composition as described herein.

An "effective amount" is an amount sufficient for a composition (e.g. compound, vaccine, drug) to accomplish a stated purpose relative to the absence of the composition (e.g. compound, vaccine, drug) (e.g. achieve the effect for which it is administered, treat a disease (e.g. reverse or prevent or reduce severity), reduce spread of an infectious disease or agent, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a composition (vaccine) is an amount of a composition that, when administered to a subject, will have the intended prophylactic effect, e.g., preventing or delaying the onset (or reoccurrence) of an injury, disease (e.g. infectious disease), pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses (e.g. prime-boost). Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of infection or one or more symptoms of infection in the absence of a composition (e.g. vaccine) as described herein (including embodiments).

"Contacting" is used in accordance with its plain ordinary meaning and refers to the process of allowing at least two distinct species (e.g. compositions, vaccines, bacterium, virus, biomolecules, or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a composition (e.g. vaccine) as described herein and a cell, virus, virus particle, protein, enzyme, or patient. In some embodiments contacting includes allowing a composition described herein to interact with a protein or enzyme that is involved in a signaling pathway. In some embodiments contacting includes allowing a composition described herein to interact with a component of a subject's immune system involved in developing immunity to a component of the composition.

As defined herein, the term "inhibition", "inhibit", "inhibiting" and the like in reference to a protein-inhibitor or interaction means negatively affecting (e.g. decreasing) the activity or function of the protein. In some embodiments inhibition refers to reduction of a disease or symptoms of disease. In some embodiments inhibition refers to reduction of the growth, proliferation, or spread of an infectious agent (e.g. bacterium or virus). In some embodiments inhibition refers to preventing the infection of a subject by an infectious agent (e.g. bacterium or virus). In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating the signaling pathway or enzymatic activity or the amount of a protein.

The term "modulator" refers to a composition that increases or decreases the level of a target (e.g. molecule, cell, bacterium, virus particle, protein) or the function of a target or the physical state of the target.

The term "modulate" is used in accordance with its plain ordinary meaning and refers to the act of changing or varying one or more properties. "Modulation" refers to the process of changing or varying one or more properties. For example, as applied to the effects of a modulator on a target, to modulate means to change by increasing or decreasing a property or function of the target or the amount of the target.

"Patient" or "subject in need thereof" refers to a living organism suffering from or prone to a disease or condition that can be treated by administration of a composition (e.g. vaccine or pharmaceutical composition) as provided herein. Non-limiting examples include humans, other mammals, bovines, rats, mice, dogs, monkeys, goat, sheep, cows, deer, and other non-mammalian animals. In some embodiments, a patient is human. In some embodiments, a patient or subject in need thereof, refers to a living organism (e.g. human) at risk of developing, contracting, or having a disease or condition associated with an infectious agent (e.g. bacterium or virus).

"Disease" or "condition" refer to a state of being or health status of a patient or subject capable of being treated with the compositions (e.g. vaccines) or methods provided herein. In some embodiments, the disease is a disease related to (e.g. caused by) an infectious agent (e.g. bacterium or virus).

"Pharmaceutically acceptable excipient" and "pharmaceutically acceptable carrier" refer to a substance that aids the administration of an active agent to or absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention. In embodiments, an excipient is a salt, sugar (saccharide), buffer, detergent, polymer, amino acid, or preservative. In embodiments, the excipient is disodium edetate, sodium chloride, sodium citrate, sodium succinate, sodium hydroxide, Sodium glucoheptonate, sodium acetyltryptophanate, sodium bicarbonate, sodium caprylate, sodium pertechnetate, sodium acetate, sodium dodecyl sulfate, ammonium citrate, calcium chloride, calcium, potassium chloride, potassium sodium tartarate, zinc oxide, zinc, stannous chloride, magnesium sulfate, magnesium stearate, titanium dioxide, DL-lactic/glycolic acids, asparagine, L-arginine, arginine hydrochloride, adenine, histidine, glycine, glutamine, glutathione, imidazole, protamine, protamine sulfate, phosphoric acid, Tri-n-butyl phosphate, ascorbic acid, cysteine hydrochloride, hydrochloric acid, hydrogen citrate, trisodium citrate, guanidine hydrochloride, mannitol, lactose, sucrose, agarose, sorbitol, maltose, trehalose, surfactants, polysorbate 80, polysorbate 20, poloxamer 188, sorbitan monooleate, triton n101, m-cresol, benyl alcohol, ethanolamine, glycerin, phosphorylethanolamine, tromethamine, 2-phenyloxyethanol, chlorobutanol, dimethylsulfoxide, N-methyl-2-pyrrolidone, propyleneglycol, polyoxyl 35 castor oil, methyl hydroxybenzoate, tromethamine, corn oil-mono-di-triglycerides, poloxyl 40 hydrogenated castor oil, tocopherol, n-acetyltryptophan, octa-fluoropropane, castor oil, polyoxyethylated oleic glycerides, polyoxytethylated castor oil, phenol, glyclyglycine, thimerosal, parab ens, gelatin, Formaldehyde, Dulbecco's modified eagles medium, hydrocortisone, neomycin, Von Willebrand factor, gluteraldehyde, benzethonium chloride, white petroleum, p-aminopheyl-p-anisate, monosodium glutamate, beta-propiolactone, acetate, citrate, glutamate, glycinate, histidine, Lactate, Maleate, phosphate, succinate, tartrate, tris, carbomer 1342 (copolymer of acrylic acid and a long chain alkyl methacrylate cross-linked with allyl ethers of pentaerythritol), glucose star polymer, silicone polymer, polydimethylsiloxane, polyethylene glycol, polyvinylpyrrolidone, carboxymethylcellulose, poly(glycolic acid), poly(lactic-co-glycolic acid), polylactic acid, dextran 40, or poloxamer.

The term "preparation" is intended to include the formulation of the active compound with encapsulating material as a carrier providing a capsule in which the active component with or without other carriers, is surrounded by a carrier, which is thus in association with it.

As used herein, the term "administering" means oral administration, administration as a suppository, topical contact, intravenous, intraperitoneal, intramuscular, intralesional, intrathecal, intranasal, intradermal, mucosal, intrarectal, intravaginal, topical, transcutaneous, or subcutaneous administration. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example infection therapies such as antiviral drugs or a vaccine (e.g different vaccine). The compositions (e.g. vaccines) of the invention can be administered alone or can be coadministered to the patient. Coadministration is meant to include simultaneous or sequential administration of the compounds individually or in combination (more than one composition) and includes vaccine administration in a prime-boost method. Thus, the preparations can also be combined, when desired, with other active substances (e.g. to reduce metabolic degradation, increase immune response (e.g. adjuvant)). The compositions of the present invention can be delivered by transdermally, by a topical route, transcutaneously, formulated as solutions, suspensions, emulsions, gels, creams, ointments, pastes, jellies, paints, powders, and aerosols.

The term "administer (or administering) a vaccine" means administering a composition that prevents or treats an infection in a subject. Administration may include, without being limited by mechanism, allowing sufficient time for the vaccine to induce an immune response in the subject or to reduce one or more symptoms of a disease.

The terms "peptide," "polypeptide," and "protein" are used interchangeably herein to refer to a polymer of amino acid residues. An "antigenic protein" is a protein that may be included in a vaccine as an antigen. In embodiments, an antigenic protein may be an antigenic protein conjugated to a sugar (i.e. saccharide) (e.g. monosaccharide, disaccharide, polysaccharide) "antigenic protein saccharide conjugate". In embodiments, an antigenic protein may be an antigenic protein that is not conjugated to a sugar (saccharide).

The term "peptidyl" and "peptidyl moiety" means a monovalent peptide.

The term "amino acid" refers to naturally occurring and synthetic amino acids, as well as amino acid analogs. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. An oligomer comprising amino acid mimetics is a peptidomimetic. A peptidomimetic moiety is a monovalent peptidomimetic.

The term "isolated" refers to a nucleic acid, polynucleotide, polypeptide, protein, or other component that is partially or completely separated from components with which it is normally associated (other proteins, nucleic acids, cells, etc.). In some embodiments, an isolated polypeptide or protein is a recombinant polypeptide or protein.

The terms "dose" and "dosage" are used interchangeably herein. A dose refers to the amount of active ingredient given to an individual at each administration. For the present methods and compositions provided herein, the dose may generally refer to the amount of disease treatment. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection.

The term "adjuvant" is used in accordance with its plain ordinary meaning within Immunology and refers to a substance that is commonly used as a component of a vaccine. Adjuvants may increase an antigen specific immune response in a subject when administered to the subject with one or more specific antigens as part of a vaccine. In some embodiments, an adjuvant accelerates an immune response to an antigen. In some embodiments, an adjuvant prolongs an immune response to an antigen. In some embodiments, an adjuvant enhances an immune response to an antigen. In some embodiments, an adjuvant is an aluminum adjuvant.

Vaccine compositions typically include an adjuvant, regardless of the nature of the agent. An adjuvant stimulates the immune system and increases the response of the immune system to the agent present in the vaccine. Most adjuvants used in vaccines in the United States are aluminum salts. Examples of aluminum salts include, but are not limited to: aluminum phosphate, aluminum hydroxide, aluminum sulfate, and aluminum potassium sulfate.

The term "aluminum adjuvant" refers to an adjuvant including aluminum. In some embodiments, an aluminum adjuvant includes aluminum hydroxide. In some embodiments, an aluminum adjuvant is aluminum hydroxide. In some embodiments, an aluminum adjuvant includes aluminum phosphate. In some embodiments, an aluminum adjuvant is aluminum phosphate. In some embodiments, an aluminum adjuvant includes potassium aluminum sulfate. In some embodiments, an aluminum adjuvant is potassium aluminum sulfate. In some embodiments, an aluminum adjuvant includes aluminum sulfate. In some embodiments, an aluminum adjuvant is aluminum sulfate. In some embodiments, an aluminum adjuvant is aluminum hydroxide adjuvant. In some embodiments, an aluminum adjuvant is aluminum phosphate adjuvant. In some embodiments, an aluminum adjuvant is potassium aluminum sulfate adjuvant. In some embodiments, an aluminum adjuvant is Alum. In some embodiments, an aluminum adjuvant is CAS no. 21645-51-2. In some embodiments, an aluminum adjuvant is aluminum hydroxide gel. In some embodiments, an aluminum adjuvant is aluminum hydroxide gel in the form of a white gelatinous precipitate. In some embodiments, an aluminum adjuvant is CAS no. 7784-30-7. In some embodiments, an aluminum adjuvant is aluminum phosphate gel. In some embodiments, an aluminum adjuvant is aluminum phosphate gel in the form of a white gelatinous precipitate. In some embodiments, an aluminum adjuvant is Imject Alum adjuvant™. In some embodiments, an aluminum adjuvant is aluminum hydroxide without magnesium hydroxide. In some embodiments, an aluminum adjuvant is Alhydrogel™. In some embodiments, an aluminum adjuvant is Adjuphos™. In some embodiments, an aluminum adjuvant is Adjuphos™. In some embodiments, an aluminum adjuvant is amorphous aluminum hydroxide and not crystalline aluminum hydroxide. In some embodiments, an aluminum adjuvant includes amorphous aluminum and not crystalline aluminum. In some embodiments, aluminum adjuvant is crystalline aluminum hydroxide and not amorphous aluminum hydroxide. In some embodiments, an aluminum adjuvant includes crystalline aluminum and not amorphous aluminum. In some embodiments, an aluminum adjuvant includes crystalline aluminum oxyhydroxide. In some embodiments, an aluminum adjuvant is crystalline aluminum oxyhydroxide. In some embodiments, an aluminum adjuvant includes amorphous aluminum hydroxyphosphate. In some embodiments, an aluminum adjuvant is amorphous aluminum hydroxyphosphate. In some embodiments, an aluminum adjuvant includes aluminum oxyhydroxide and not aluminum hydroxycarbonate. In some embodiments, an aluminum adjuvant is aluminum oxyhydroxide and not aluminum hydroxycarbonate. In some embodiments, an aluminum adjuvant includes aluminum oxyhydroxide and not magnesium hydroxide. In some embodiments, an aluminum adjuvant is aluminum oxyhydroxide and not magnesium hydroxide. In some embodiments, an aluminum adjuvant does not include amorphous aluminum hydroxide in which some hydroxyls are replaced by sulfate anions. In some embodiments, an aluminum adjuvant includes aluminum oxyhydroxide in a Boehmite-like pattern. In some embodiments, an aluminum adjuvant is aluminum oxyhydroxide in a Boehmite-like pattern. In some embodiments of an aluminum adjuvant described above, the description is of the aluminum adjuvant prior to inclusion in a vaccine. In some embodiments, an aluminum adjuvant is an aluminum containing adjuvant approved by the FDA for administration to humans. In some embodiments, an aluminum adjuvant is an aluminum hydroxide adjuvant approved for administration to humans by the FDA. In some embodiments, an aluminum adjuvant is an aluminum phosphate adjuvant approved for administration to humans by the FDA.

The term "aluminum hydroxide adjuvant" as used herein refers to the aluminum hydroxide adjuvant that includes aluminum hydroxide and is currently used in human vaccines (e.g. marketed and/or approved human vaccines, such as FDA approved human vaccines). In some embodiments, "aluminum hydroxide adjuvant" as used herein refers to the aluminum hydroxide adjuvant that is currently used in human vaccines (e.g. marketed and/or approved human vaccines, such as FDA approved human vaccines) and is used in accordance with the use of that term in Hem S. L., Vaccine 23(2007) 4985-4986. In some embodiments, an aluminum hydroxide adjuvant includes CAS no. 21645-51-2. In some embodiments, an aluminum hydroxide adjuvant is aluminum hydroxide gel. In some embodiments, an aluminum hydroxide adjuvant is aluminum hydroxide gel in the form of a white gelatinous precipitate. In some embodiments, an aluminum hydroxide adjuvant includes aluminum hydroxide and does not include magnesium hydroxide. In some embodiments, an aluminum hydroxide adjuvant is Alhydrogel™. In some embodiments, an aluminum hydroxide adjuvant includes crystalline aluminum hydroxide and not amorphous aluminum hydroxide. In some embodiments, an aluminum hydroxide adjuvant includes crystalline aluminum and not amorphous aluminum. In some embodiments, an aluminum hydroxide adjuvant includes crystalline aluminum oxyhydroxide. In some embodiments, an aluminum hydroxide is crystalline aluminum oxyhydroxide. In some embodiments, an aluminum hydroxide adjuvant includes aluminum oxyhydroxide and not aluminum hydroxycarbonate. In some embodiments, an aluminum hydroxide adjuvant is aluminum oxyhydroxide and not aluminum hydroxycarbonate. In some embodiments, an aluminum hydroxide adjuvant does not include amorphous aluminum hydroxide in which some hydroxyls are replaced by sulfate anions. In some embodiments, aluminum hydroxide adjuvant includes aluminum oxyhydroxide in a Boehmite-like pattern. In some embodiments of an aluminum hydroxide adjuvant described above, the description is of the aluminum hydroxide adjuvant prior to inclusion in a vaccine.

The term "aluminum phosphate adjuvant" as used herein refers to the aluminum phosphate adjuvant that includes aluminum phosphate and is currently used in human vaccines (e.g. marketed and/or approved human vaccines, such as FDA approved human vaccines). In some embodiments, "aluminum phosphate adjuvant" as used herein refers to the aluminum phosphate adjuvant that is currently used in human vaccines (e.g. marketed and/or approved human vaccines, such as FDA approved human vaccines) and is used in accordance with the use of that term in Hem S. L., Vaccine 23(2007) 4985-4986. In some embodiments, an aluminum phosphate adjuvant includes CAS no. 7784-30-7. In some embodiments, an aluminum phosphate adjuvant is aluminum phosphate gel. In some embodiments, an aluminum phosphate adjuvant is aluminum phosphate gel in the form of a white gelatinous precipitate. In some embodiments, an aluminum phosphate adjuvant is Adjuphos™. In some embodiments, an aluminum phosphate adjuvant is Adjuphos™. In some embodiments, an aluminum phosphate adjuvant includes amorphous aluminum hydroxyphosphate. In some embodiments of an aluminum phosphate adjuvant described above, the description is of the aluminum phosphate adjuvant prior to inclusion in a vaccine.

The terms "bind", "bound", "binding", and other verb forms thereof are used in accordance with their plain ordinary meaning within Enzymology and Biochemistry and refer to the formation of one or more interactions or contacts between two compositions that may optionally interact. Binding may be intermolecular or intramolecular.

The term "potassium aluminum sulfate adjuvant" refers to an adjuvant that includes potassium aluminum sulfate. The term "aluminum sulfate adjuvant" refers to an adjuvant that includes aluminum sulfate.

The term "vaccine" is used according to its plain ordinary meaning within medicine and Immunology and refers to a composition including an antigenic component (e.g. antigenic protein) for administration to a subject (e.g. human), which elicits an immune response to the antigenic component (e.g. antigenic protein). In some embodiments a vaccine is a therapeutic. In some embodiments, a vaccine is prophylactic. In some embodiments a vaccine includes one or more adjuvants (e.g. aluminum adjuvant). A liquid vaccine is a vaccine in liquid form, which may be for example a solution, suspension, emulsion, or dispersion or the antigenic component (e.g. antigenic protein) of the vaccine and may optionally include other components. A dry vaccine is a vaccine comprising 5% or less of water.

A vaccine is a preparation employed to improve immunity to a particular disease. Vaccines include an agent, which is used to induce a response from the immune system of the subject. Various agents that are typically used in a vaccine include, but are not limited to: killed, but previously virulent, micro-organisms; live, attenuated microorganisms; inactivated toxic compounds that are produced by microorganism that cause an illness; protein subunits of microorganisms; and conjugates. Examples of vaccines that may be converted into a powder vaccine according to the methods described herein include, but are not limited to: influenza vaccine, cholera vaccine, bubonic plague vaccine, polio vaccine, Hepatitis A vaccine, rabies vaccine, yellow fever vaccine, measles vaccine, rubella vaccine, mumps vaccine, typhoid vaccine, tuberculosis vaccine, tetanus vaccine, diphtheria vaccine, diphtheria-tetanus-pertussis vaccine, Hepatitis B vaccine, human papillomavirus (HPV) vaccine, Pneumococcal conjugate vaccines, influenza vaccine, botulism vaccine, polio vaccine, and anthrax vaccines.

The term "prime-boost" or "prime boost" as applied to a methodology of administering vaccines is used according to its plain ordinary meaning in Virology and Immunology and refers to a method of vaccine administration in which a first dose of a vaccine or vaccine component is administered to a subject or patient to begin the administration (prime) and at a later time (e.g. hours, days, weeks, months later) a second vaccine is administered to the same patient or subject (boost). The first and second vaccines may be the same or different but are intended to both elicit an immune response useful in treating or preventing the same disease or condition. In some embodiments the prime is one or more viral proteins or portions thereof and the boost is one or more viral proteins or portions thereof.

The term "associated" or "associated with" as used herein to describe a disease (e.g. a virus associated disease or bacteria associated disease) means that the disease is caused by, or a symptom of the disease is caused by, what is described as disease associated or what is described as associated with the disease. As used herein, what is described as being associated with a disease, if a causative agent, could be a target for treatment of the disease.

The term "vaccinate", or additional verb forms thereof, refers to administering a vaccine to a subject (e.g. human) and eliciting an antigen specific immune response, wherein the antigen (e.g. antigenic protein) is included in the vaccine. The term "vaccinate" may also refer to eliciting an antigen specific immune response against an administered antigen (e.g. antigenic protein). In some embodiments, vaccinate is to provide prophylaxis against a disease or infectious agent.

The term "portion" refers to a subset of a whole, which may also be the whole. In some embodiments, a portion is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%. In some embodoments, a portion is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%. Unless indicated otherwise, the term "about" in the context of a numeric value indicates the nominal value ±10% of the nominal value. In some embodiments, "about" may be the nominal value.

B. Compositions

In an aspect is provided a dry vaccine including an antigenic protein and an aluminum adjuvant, wherein at least 75% of the antigenic protein is adsorbed to the aluminum adjuvant.

In embodiments, at least 60% of the antigenic protein is not denatured. In embodiments, at least 70% of the antigenic protein is not denatured. In embodiments, at least 80% of the antigenic protein is not denatured. In embodiments, at least 90% of the antigenic protein is not denatured. In embodiments, at least 95% of the antigenic protein is not denatured. In embodiments, at least 60% of the antigenic protein is in a conformationally native state. In embodiments, at least 70% of the antigenic protein is in a conformationally native state. In embodiments, at least 80% of the antigenic protein is in a conformationally native state. In embodiments, at least 90% of the antigenic protein is in a conformationally native state. In embodiments, at least 95% of the antigenic protein is in a conformationally native state. A "conformationally native state" is a folded conformation corresponding to an operative or functional protein. A "denatured" protein is a protein having a conformation differing from the folded active or functional conformation of the protein, wherein the denatured protein has a reduced level of activity or function. In embodiments, the antigentic protein is an unconjugated antigenic protein. In embodiments, the antigenic protein is an antigenic protein sugar (saccharide) conjugate. In embodiments, the sugar (saccharide) is a monosaccharide. In embodiments, the sugar (saccharide) is a disaccharide. In embodiments, the sugar (saccharide) is a polysaccharide.

In embodiments, the aluminum adjuvant includes aluminum hydroxide. In embodiments, the aluminum adjuvant includes aluminum phosphate. In embodiments, the aluminum adjuvant includes potassium aluminum sulfate. In embodiments, the aluminum adjuvant is aluminum hydroxide. In embodiments, the aluminum adjuvant is aluminum phosphate. In embodiments, the aluminum adjuvant is potassium aluminum sulfate. In embodiments, the aluminum adjuvant is aluminum sulfate. In embodiments, the dry vaccine includes between 0.5 and 5% (wt/wt) of the aluminum adjuvant. In embodiments, the dry vaccine includes between 0.5 and 4% (wt/wt) of the aluminum adjuvant. In embodiments, the dry vaccine includes between 0.5 and 3% (wt/wt) of the aluminum adjuvant. In embodiments, the dry vaccine includes between 0.5 and 2% (wt/wt) of the aluminum adjuvant. In embodiments, the dry vaccine includes between 0.75 and 2% (wt/wt) of the aluminum adjuvant. In embodiments, the dry vaccine includes between 1 and 2% (wt/wt) of the aluminum adjuvant. In embodiments, the dry vaccine includes about 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes at least 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes less than 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes between 0.08 and 1% (wt/wt) of the aluminum adjuvant.

In embodiments, the dry vaccine includes less than 5% water. In embodiments, the dry vaccine includes less than 4% water. In embodiments, the dry vaccine includes less than 3% water. In embodiments, the dry vaccine includes less than 2% water. In embodiments, the dry vaccine includes less than 1% water. In embodiments, the dry vaccine includes less than 5% water (wt/wt). In embodiments, the dry vaccine includes less than 4% water (wt/wt). In embodiments, the dry vaccine includes less than 3% water (wt/wt). In embodiments, the dry vaccine includes less than 2% water (wt/wt). In embodiments, the dry vaccine includes less than 1% water (wt/wt). In embodiments, the dry vaccine includes about 5% water. In embodiments, the dry vaccine includes about 4% water. In embodiments, the dry vaccine includes about 3% water. In embodiments, the dry vaccine includes about 2% water. In embodiments, the dry vaccine includes about 1% water. In embodiments, the dry vaccine includes about 5% water (wt/wt). In embodiments, the dry vaccine includes about 4% water (wt/wt). In embodiments, the dry vaccine includes about 3% water (wt/wt). In embodiments, the dry vaccine includes about 2% water (wt/wt). In embodiments, the dry vaccine includes about 1% water (wt/wt). In embodiments, the dry vaccine includes less than 5% water (v/v). In embodiments, the dry vaccine includes less than 4% water (v/v). In embodiments, the dry vaccine includes less than 3% water (v/v). In embodiments, the dry vaccine includes less than 2% water (v/v). In embodiments, the dry vaccine includes less than 1% water (v/v). In embodiments, the dry vaccine includes about 5% water (v/v). In embodiments, the dry vaccine includes about 4% water (v/v). In embodiments, the dry vaccine includes about 3% water (v/v). In embodiments, the dry vaccine includes about 2% water (v/v). In embodiments, the dry vaccine includes about 1% water (v/v).

In embodiments, at least 75% of the antigenic protein is adsorbed to the aluminum adjuvant. In embodiments, at least 80% of the antigenic protein is adsorbed to the aluminum adjuvant. In embodiments, at least 85% of the antigenic protein is adsorbed to the aluminum adjuvant. In embodiments, at least 90% of the antigenic protein is adsorbed to the aluminum adjuvant. In embodiments, at least 92% of the antigenic protein is adsorbed to the aluminum adjuvant. In embodiments, at least 95% of the antigenic protein is adsorbed to the aluminum adjuvant. In embodiments, at least 98% of the antigenic protein is adsorbed to the aluminum adjuvant. In embodiments, at least 99% of the antigenic protein is adsorbed to the aluminum adjuvant. In embodiments, about 75% of the antigenic protein is adsorbed to the aluminum adjuvant. In embodiments, about 80% of the antigenic protein is adsorbed to the aluminum adjuvant. In embodiments, about 85% of the antigenic protein is adsorbed to the aluminum adjuvant. In embodiments, about 90% of the antigenic protein is adsorbed to the aluminum adjuvant. In embodiments, about 92% of the antigenic protein is adsorbed to the aluminum adjuvant. In embodiments, about 95% of the antigenic protein is adsorbed to the aluminum adjuvant. In embodiments, about 98% of the antigenic protein is adsorbed to the aluminum adjuvant. In embodiments, about 99% of the antigenic protein is adsorbed to the aluminum adjuvant.

In embodiments, the dry vaccine includes an excipient. In embodiments, the dry vaccine includes a plurality of different excipients. In embodiments, the excipient is a salt, sugar (saccharide), buffer, detergent, polymer, amino acid, or preservative. In embodiments, the excipient is disodium edetate, sodium chloride, sodium citrate, sodium succinate, sodium hydroxide, Sodium glucoheptonate, sodium acetyl-tryptophanate, sodium bicarbonate, sodium caprylate, sodium pertechnetate, sodium acetate, sodium dodecyl sulfate, ammonium citrate, calcium chloride, calcium, potassium chloride, potassium sodium tartarate, zinc oxide, zinc, stannous chloride, magnesium sulfate, magnesium stearate, titanium dioxide, DL-lactic/glycolic acids, asparagine, L-arginine, arginine hydrochloride, adenine, histidine, glycine, glutamine, glutathione, imidazole, protamine, protamine sulfate, phosphoric acid, Tri-n-butyl phosphate, ascorbic acid, cysteine hydrochloride, hydrochloric acid, hydrogen citrate, trisodium citrate, guanidine hydrochloride, mannitol, lactose, sucrose, agarose, sorbitol, maltose, trehalose, surfactants, polysorbate 80, polysorbate 20, poloxamer 188, sorbitan monooleate, triton n101, m-cresol, benyl alcohol, ethanolamine, glycerin, phosphorylethanolamine, tromethamine, 2-phenyloxyethanol, chlorobutanol, dimethylsulfoxide, N-methyl-2-pyrrolidone, propyleneglycol, polyoxyl 35 castor oil, methyl hydroxybenzoate, tromethamine, corn oil-mono-di-triglycerides, poloxyl 40 hydrogenated castor oil, tocopherol, n-acetyltryptophan, octa-fluoropropane, castor oil, polyoxyethylated oleic glycerides, polyoxytethylated castor oil, phenol, glyclyglycine, thimerosal, parabens, gelatin, Formaldehyde, Dulbecco's modified eagles medium, hydrocortisone, neomycin, Von Willebrand factor, gluteraldehyde, benzethonium chloride, white petroleum, p-aminopheyl-p-anisate, monosodium glutamate, beta-propiolactone, acetate, citrate, glutamate, glycinate, histidine, Lactate, Maleate, phosphate, succinate, tartrate, tris, carbomer 1342 (copolymer of acrylic acid and a long chain alkyl methacrylate cross-linked with allyl ethers of pentaerythritol), glucose star polymer, silicone polymer, polydimethylsiloxane, polyethylene glycol, polyvinylpyrrolidone, carboxymethylcellulose, poly(glycolic acid), poly(lactic-co-glycolic acid), polylactic acid, dextran 40, or poloxamer. In embodiments, the excipient is trehalose. In embodiments, the dry vaccine includes less than 5% wt/wt of the excipient. In embodiments, the dry vaccine includes less than 4% wt/wt of the excipient. In embodiments, the dry vaccine includes less than 3% wt/wt of the excipient. In embodiments, the dry vaccine includes less than 2% wt/wt of the excipient. In embodiments, the dry vaccine includes less than 1% wt/wt of the excipient. In embodiments, the dry vaccine includes less than 0.5% wt/wt of the excipient. In embodiments, the dry vaccine includes about 5% wt/wt of the excipient. In embodiments, the dry vaccine includes about 4% wt/wt of the excipient. In embodiments, the dry vaccine includes about 3% wt/wt of the excipient. In embodiments, the dry vaccine includes about 2% wt/wt of the excipient. In embodiments, the dry vaccine includes about 1% wt/wt of the excipient. In embodiments, the dry vaccine includes about 0.5% wt/wt of the excipient.

In embodiments, the dry vaccine includes particles, wherein the particles include the antigenic protein adsorbed to the aluminum adjuvant. In embodiments, the dry vaccine is prepared from a liquid vaccine.

In an embodiment, a powder (e.g. dry) vaccine, which retains its efficacy, may be made from a vaccine composition. The method includes obtaining a liquid (e.g. aqueous) vaccine composition. The vaccine composition includes an agent that resembles a disease-causing microorganism or a compound associated with the disease-causing microorganism (e.g. antigenic protein). The vaccine composition also includes an adjuvant (e.g. aluminum adjuvant). The vaccine composition is frozen to obtain a frozen vaccine composition (e.g. vaccine thin film). Water is removed from the frozen vaccine composition to form a powder (e.g. dry) vaccine that includes the agent or compound (e.g. antigenic protein) and the adjuvant (e.g. aluminum adjuvant).

A cryoprotectant may be added to the vaccine composition to protect the organisms or agents present in the composition (either live or dead) from damage during the freezing process. Examples of cryoprotectants include dimethyl sulfoxide, glycerol, monosaccharides, and polysaccharides (e.g., trehalose). A cryoprotectant may be present in amounts up to about 5% by weight.

Additionally, the solid form of the vaccine is expected to be advantageous over vaccine dispersion (i.e., suspension) for stockpiling vaccines that are critical to national security and public health. For example, botulism is a life-threatening disease caused by botulinum neurotoxins (BoNTs), which are produced by one of the seven structurally similar *Clostridium botulinum* serotypes, designated A to G. Each of the toxins is immunologically distinct, except that serotypes C and D share significant cross-homology. BoNTs are the most poisonous substances known in nature. A single gram of crystalline toxin, evenly dispersed and inhaled, would kill more than one million people. Previously, an investigational pentavalent botulism toxoid (PBT) vaccine aiming to protect against BoNT serotypes A-E had been available. However, as of November 2011, the PBT vaccine has been discontinued by the Centers for Disease Control and Prevention (CDC), based on "an assessment of the available data, which indicate a decline in immunogenicity of some of the toxin serotypes". Since the investigative PBT vaccine was the only botulism vaccine available in the U.S., discontinuation of it has significant national security implications.

In another embodiment, an aqueous vaccine composition may be composed of an agent and an aluminum adjuvant that form particles having a particle size of less than about 200 nm (e.g. less than 10, 20, 30, 40, 50, 60, 70, 80, 90, 100, 110, 120, 130, 140, 150, 160, 170, 180, 190, 200 nm). In some embodiments, aluminum hydroxide or aluminum phosphate particles having a diameter of less than 200 nm (e.g. less than 10, 20, 30, 40, 50, 60, 70, 80, 90, 100, 110, 120, 130, 140, 150, 160, 170, 180, 190, 200 nm) may be used as adjuvants in a vaccine composition. The vaccine composition may be formed by mixing the agent of the vaccine with the aluminum adjuvant particles in water. The aqueous vaccine composition may be used to vaccinate a subject against the disease related to the agent. In some embodiments, the aqueous vaccine composition can be converted to a vaccine powder, as described above, for storage, for use as an inhalant, or use in other delivery modes.

In embodiments, a dry vaccine is the dry vaccine described herein, including in embodiments, examples, tables, figures, and claims. In embodiments, a dry vaccine is a dry vaccine made by a method described herein, including in aspects, embodiments, examples, tables, figures, and claims. Provided herein is a reconstituted liquid vaccine comprising a dry vaccine as described herein (including in an aspect, embodiment, example, table, figure, or claim) or a dry vaccine prepared using a method as described herein (including in an aspect, embodiment, example, table, figure, or claim) and a solvent (e.g. water, buffer, solution, liquid including an excipient).

Provided in another aspect is a pharmaceutical composition including a pharmaceutically acceptable excipient and any of the compositions (e.g. vaccines) described herein (including embodiment).

The compositions described herein (including embodiments and examples) can be administered alone or can be coadministered to the patient. Coadministration is meant to include simultaneous or sequential administration of the compositions individually or in combination (more than one composition). Thus, the preparations can also be combined, when desired, with other active substances (e.g. to reduce metabolic degradation, increase immune response (e.g. adjuvants)). An example of coadministration of vaccine compositions is a prime-boost method of administration.

Pharmaceutical compositions provided by the present invention include compositions wherein the active ingredient (e.g. compositions described herein, including embodiments) is contained in a therapeutically or prophylactically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., prevent infection, and/or reducing, eliminating, or slowing the progression of disease symptoms. Determination of a therapeutically or prophylactically effective amount of a composition of the invention is well within the capabilities of those skilled in the art, especially in light of the detailed disclosure herein.

C. Methods

In an aspect is provided a method for preparing a vaccine thin film including: applying a liquid vaccine to a freezing surface; allowing the liquid vaccine to disperse and freeze on the freezing surface thereby forming a vaccine thin film. The liquid vaccine includes aluminum (e.g. aluminum adjuvant).

In embodiments, the aluminum adjuvant includes aluminum hydroxide. In embodiments, the aluminum adjuvant includes aluminum phosphate. In embodiments, the aluminum adjuvant includes potassium aluminum sulfate. In embodiments, the aluminum adjuvant is aluminum hydroxide. In embodiments, the aluminum adjuvant is aluminum phosphate. In embodiments, the aluminum adjuvant is potassium aluminum sulfate. In embodiments, the aluminum adjuvant includes aluminum sulfate. In embodiments, the aluminum adjuvant is aluminum sulfate. In embodiments, the liquid vaccine includes between 0.5 and 5% (wt/wt) of the aluminum adjuvant. In embodiments, the liquid vaccine includes between 0.5 and 4% (wt/wt) of the aluminum adjuvant. In embodiments, the liquid vaccine includes between 0.5 and 3% (wt/wt) of the aluminum adjuvant. In embodiments, the liquid vaccine includes between 0.5 and 2% (wt/wt) of the aluminum adjuvant. In embodiments, the liquid vaccine includes between 0.75 and 2% (wt/wt) of the aluminum adjuvant. In embodiments, the liquid vaccine includes between 1 and 2% (wt/wt) of the aluminum adjuvant. In embodiments, the liquid vaccine includes about 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the liquid vaccine includes at least 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the liquid vaccine includes less than 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the liquid vaccine includes 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the liquid vaccine includes between 0.5 and 5% (wt/vol) of the aluminum adjuvant/liquid vaccine. In embodiments, the liquid vaccine includes between 0.5 and 4% (wt/vol) of the aluminum adjuvant/liquid vaccine. In embodiments, the liquid vaccine includes between 0.5 and 3% (wt/vol) of the aluminum adjuvant/liquid vaccine. In embodiments, the liquid vaccine includes between 0.5 and 2% (wt/vol) of the aluminum adjuvant/liquid vaccine. In embodiments, the liquid vaccine includes between 0.75 and 2% (wt/vol) of the aluminum adjuvant/liquid vaccine. In embodiments, the liquid vaccine includes between 1 and 2% (wt/vol) of the aluminum adjuvant/liquid vaccine. In embodiments, the liquid vaccine includes about 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine. In embodiments, the liquid vaccine includes at least 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine. In embodiments, the liquid vaccine includes less than 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine. In embodiments, the liquid vaccine includes 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine. In embodiments, the liquid vaccine includes between 0.08 and 1% (wt/vol) of the aluminum adjuvant/liquid vaccine. In embodiments, the liquid vaccine includes between about 0.5 and about 5% (wt/wt) of the aluminum adjuvant. In embodiments, the liquid vaccine includes between about 0.5 and about 4% (wt/wt) of the aluminum adjuvant. In embodiments, the liquid vaccine includes between about 0.5 and about 3% (wt/wt) of the aluminum adjuvant. In embodiments, the liquid vaccine includes between about 0.5 and about 2% (wt/wt) of the aluminum adjuvant. In embodiments, the liquid vaccine includes between about 0.75 and about 2% (wt/wt) of the aluminum adjuvant. In embodiments, the liquid vaccine includes between about 1 and about 2% (wt/wt) of the aluminum adjuvant. In embodiments, the liquid vaccine includes about 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the liquid vaccine includes at least about 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the liquid vaccine includes less than about 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the liquid vaccine includes about 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the liquid vaccine includes between about 0.5 and about 5% (wt/vol) of the aluminum adjuvant/liquid vaccine. In embodiments, the liquid vaccine includes between about 0.5 and about 4% (wt/vol) of the aluminum adjuvant/liquid vaccine. In embodiments, the liquid vaccine includes between about 0.5 and about 3% (wt/vol) of the aluminum adjuvant/liquid vaccine. In embodiments, the liquid vaccine includes between about 0.5 and about 2% (wt/vol) of the aluminum adjuvant/liquid vaccine. In embodiments, the liquid vaccine includes between about 0.75 and about 2% (wt/vol) of the aluminum adjuvant/liquid vaccine. In embodiments, the liquid vaccine includes between about 1 and about 2% (wt/vol) of the aluminum adjuvant/liquid vaccine. In embodiments, the liquid vaccine includes about about 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine. In embodiments, the liquid vaccine includes at least about 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine. In embodiments, the liquid vaccine includes less than about 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine. In embodiments, the liquid vaccine includes about 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine. In embodiments, the liquid vaccine includes between about 0.08 and about 1% (wt/vol) of the aluminum adjuvant/liquid vaccine.

In embodiments, the liquid vaccine includes a ratio of antigenic protein to aluminum adjuvant (wt/wt) of about 1:10. In embodiments, the liquid vaccine includes a ratio of antigenic protein to aluminum adjuvant (wt/wt) of about 1:9. In embodiments, the liquid vaccine includes a ratio of antigenic protein to aluminum adjuvant (wt/wt) of about 1:8. In embodiments, the liquid vaccine includes a ratio of antigenic protein to aluminum adjuvant (wt/wt) of about 1:7. In embodiments, the liquid vaccine includes a ratio of antigenic protein to aluminum adjuvant (wt/wt) of about 1:6. In embodiments, the liquid vaccine includes a ratio of antigenic protein to aluminum adjuvant (wt/wt) of about 1:5. In embodiments, the liquid vaccine includes a ratio of antigenic protein to aluminum adjuvant (wt/wt) of about 1:4. In embodiments, the liquid vaccine includes a ratio of antigenic protein to aluminum adjuvant (wt/wt) of about 1:3. In embodiments, the liquid vaccine includes a ratio of antigenic protein to aluminum adjuvant (wt/wt) of about 1:2. In embodiments, the liquid vaccine includes a ratio of antigenic protein to aluminum adjuvant (wt/wt) of about 1:1. In embodiments, the liquid vaccine includes a ratio of antigenic protein to aluminum adjuvant (wt/wt) of less than 1:10. In embodiments, the liquid vaccine includes a ratio of antigenic protein to aluminum adjuvant (wt/wt) of 1:10. In embodiments, the liquid vaccine includes a ratio of antigenic protein to aluminum adjuvant (wt/wt) of 1:9. In embodiments, the liquid vaccine includes a ratio of antigenic protein to aluminum adjuvant (wt/wt) of 1:8. In embodiments, the liquid vaccine includes a ratio of antigenic protein to aluminum adjuvant (wt/wt) of 1:7. In embodiments, the liquid vaccine includes a ratio of antigenic protein to aluminum adjuvant (wt/wt) of 1:6. In embodiments, the liquid vaccine includes a ratio of antigenic protein to aluminum adjuvant (wt/wt) of 1:5. In embodiments, the liquid vaccine includes a ratio of antigenic protein to aluminum adjuvant (wt/wt) of 1:4. In embodiments, the liquid vaccine includes a ratio of antigenic protein to aluminum adjuvant (wt/wt) of 1:3. In embodiments, the liquid vaccine includes a ratio of antigenic protein to aluminum adjuvant (wt/wt) of 1:2. In embodiments, the liquid vaccine includes a ratio of antigenic protein to aluminum adjuvant (wt/wt) of 1:1.

In embodiments, the liquid vaccine includes an excipient. In embodiments, the liquid vaccine includes a plurality of different excipients. In embodiments, the excipient is a salt, sugar (saccharide), buffer, detergent, polymer, amino acid, or preservative. In embodiments, the excipient is disodium edetate, sodium chloride, sodium citrate, sodium succinate, sodium hydroxide, Sodium glucoheptonate, sodium acetyltryptophanate, sodium bicarbonate, sodium caprylate, sodium pertechnetate, sodium acetate, sodium dodecyl sulfate, ammonium citrate, calcium chloride, calcium, potassium chloride, potassium sodium tartarate, zinc oxide, zinc, stannous chloride, magnesium sulfate, magnesium stearate, titanium dioxide, DL-lactic/glycolic acids, asparagine, L-arginine, arginine hydrochloride, adenine, histidine, glycine, glutamine, glutathione, imidazole, protamine, protamine sulfate, phosphoric acid, Tri-n-butyl phosphate, ascorbic acid, cysteine hydrochloride, hydrochloric acid, hydrogen citrate, trisodium citrate, guanidine hydrochloride, mannitol, lactose, sucrose, agarose, sorbitol, maltose, trehalose, surfactants, polysorbate 80, polysorbate 20, poloxamer 188, sorbitan monooleate, triton n101, m-cresol, benyl alcohol, ethanolamine, glycerin, phosphorylethanolamine, tromethamine, 2-phenyloxyethanol, chlorobutanol, dimethylsulfoxide, N-methyl-2-pyrrolidone, propyleneglycol, polyoxyl 35 castor oil, methyl hydroxybenzoate, tromethamine, corn oil-mono-di-triglycerides, poloxyl 40 hydrogenated castor oil, tocopherol, n-acetyltryptophan, octa-fluoropropane, castor oil, polyoxyethylated oleic glycerides, polyoxytethylated castor oil, phenol, glyclyglycine, thimerosal, parabens, gelatin, Formaldehyde, Dulbecco's modified eagles medium, hydrocortisone, neomycin, Von Willebrand factor, gluteraldehyde, benzethonium chloride, white petroleum, p-aminopheyl-p-anisate, monosodium glutamate, beta-propiolactone, acetate, citrate, glutamate, glycinate, histidine, Lactate, Maleate, phosphate, succinate, tartrate, tris, carbomer 1342 (copolymer of acrylic acid and a long chain alkyl methacrylate cross-linked with allyl ethers of pentaerythritol), glucose star polymer, silicone polymer, polydimethylsiloxane, polyethylene glycol, polyvinylpyrrolidone, carboxymethylcellulose, poly(glycolic acid), poly(lactic-co-glycolic acid), polylactic acid, dextran 40, or poloxamer. In embodiments, the excipient is trehalose. In embodiments, the liquid vaccine includes less than 5% wt/vol of the excipient/liquid vaccine. In embodiments, the liquid vaccine includes less than 4% wt/vol of the excipient/liquid vaccine. In embodiments, the liquid vaccine includes less than 3% wt/vol of the excipient/liquid vaccine. In embodiments, the liquid vaccine includes less than 2% wt/vol of the excipient/liquid vaccine. In embodiments, the liquid vaccine includes less than 1% wt/vol of the excipient/liquid vaccine. In embodiments, the liquid vaccine includes less than 0.5% wt/vol of the excipient/liquid vaccine. In embodiments, the liquid vaccine includes about 5% wt/vol of the excipient/liquid vaccine. In embodiments, the liquid vaccine includes about 4% wt/vol of the excipient/liquid vaccine. In embodiments, the liquid vaccine includes about 3% wt/vol of the excipient/liquid vaccine. In embodiments, the liquid vaccine includes about 2% wt/vol of the excipient/liquid vaccine. In embodiments, the liquid vaccine includes about 1% wt/vol of the excipient/liquid vaccine. In embodiments, the liquid vaccine includes about 0.5% wt/vol of the excipient/liquid vaccine. In embodiments, the liquid vaccine includes about 0.1, 0.2, 0.3, 0.4, 0.5, 0.6, 0.7, 0.8, 0.9, 1, 2, 3, 4, 5, 6, 7, 8, 9, or 10% (wt/vol) of the excipient/liquid vaccine. In embodiments, the liquid vaccine includes 0.1, 0.2, 0.3, 0.4, 0.5, 0.6, 0.7, 0.8, 0.9, 1, 2, 3, 4, 5, 6, 7, 8, 9, or 10% (wt/vol) of the excipient/liquid vaccine. In embodiments, the liquid vaccine includes less than 5% of the excipient. In embodiments, the liquid vaccine includes less than 4% of the excipient. In embodiments, the liquid vaccine includes less than 3% of the excipient. In embodiments, the liquid vaccine includes less than 2% of the excipient. In embodiments, the liquid vaccine includes less than 1% of the excipient. In embodiments, the liquid vaccine includes less than 0.5% of the excipient. In embodiments, the liquid vaccine includes about 5% of the excipient. In embodiments, the liquid vaccine includes about 4% of the excipient. In embodiments, the liquid vaccine includes about 3% of the excipient. In embodiments, the liquid vaccine includes about 2% of the excipient. In embodiments, the liquid vaccine includes about 1% of the excipient. In embodiments, the liquid vaccine includes about 0.5% of the excipient. In embodiments, the liquid vaccine includes about 0.1, 0.2, 0.3, 0.4, 0.5, 0.6, 0.7, 0.8, 0.9, 1, 2, 3, 4, 5, 6, 7, 8, 9, or 10% of the excipient. In embodiments, the liquid vaccine includes 0.1, 0.2, 0.3, 0.4, 0.5, 0.6, 0.7, 0.8, 0.9, 1, 2, 3, 4, 5, 6, 7, 8, 9, or 10% of the excipient.

In embodiments, the applying includes spraying or dripping droplets of the liquid vaccine. In embodiments, the vapor-liquid interface of the droplets is less than 500 cm$^{-1}$ area/volume. In embodiments, the vapor-liquid interface of the droplets is less than 400 cm$^{-1}$ area/volume. In embodiments, the vapor-liquid interface of the droplets is less than 300 cm$^{-1}$ area/volume. In embodiments, the vapor-liquid interface of the droplets is less than 200 cm$^{-1}$ area/volume. In embodiments, the vapor-liquid interface of the droplets is less than 100 cm$^{-1}$ area/volume. In embodiments, the vapor-liquid interface of the droplets is less than 50 cm$^{-1}$ area/volume. In embodiments, the vapor-liquid interface of the droplets is less than 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 cm$^{-1}$ area/volume.

In embodiments, the method further includes contacting the droplets with a freezing surface having a temperature below the freezing temperature of the liquid vaccine (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 degrees Celsius below the freezing temperature). In embodiments, the method further includes contacting the droplets with a freezing surface having a temperature differential of at least 30° C. between the droplets and the surface. In embodiments, the temperature differential is at least 40° C. between the droplets and the surface. In embodiments, the temperature differential is at least 50° C. between the droplets and the surface. In embodiments, the temperature differential is at least 60° C. between the droplets and the surface. In embodiments, the temperature differential is at least 70° C. between the droplets and the surface. In embodiments, the temperature differential is at least 80° C. between the droplets and the surface. In embodiments, the temperature differential is at least 90° C. between the droplets and the surface. In embodiments, the temperature differential between the droplets and the surface is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 degrees Celsius.

In embodiments, the vaccine thin film has a thickness of less than 500 micrometers. In embodiments, the vaccine thin film has a thickness of less than 400 micrometers. In embodiments, the vaccine thin film has a thickness of less than 300 micrometers. In embodiments, the vaccine thin film has a thickness of less than 200 micrometers. In embodiments, the vaccine thin film has a thickness of less than 100 micrometers. In embodiments, the vaccine thin film has a thickness of less than 50 micrometers. In embodiments, the vaccine thin film has a thickness of less than 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 micrometers. In embodiments, the vaccine thin film has a thickness of about 500 micrometers. In embodiments, the vaccine thin film has a thickness of about 400 micrometers. In embodiments, the vaccine thin film has a thickness of about 300 micrometers. In embodiments, the vaccine thin film has a thickness of about 200 micrometers. In embodiments, the vaccine thin film has a thickness of about 100 micrometers. In embodiments, the vaccine thin film has a thickness of about 50 micrometers. In embodiments, the vaccine thin film has a thickness of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 micrometers.

In embodiments, the vaccine thin film has a surface area to volume ratio of between 25 and 500 cm$^{-1}$. In embodiments, the vaccine thin film has a surface area to volume ratio of between 25 and 400 cm$^{-1}$. In embodiments, the vaccine thin film has a surface area to volume ratio of between 25 and 300 cm$^{-1}$. In embodiments, the vaccine thin film has a surface area to volume ratio of between 25 and 200 cm$^{-1}$. In embodiments, the vaccine thin film has a surface area to volume ratio of between 25 and 100 cm$^{-1}$. In embodiments, the vaccine thin film has a surface area to volume ratio of between 100 and 500 cm$^{-1}$. In embodiments, the vaccine thin film has a surface area to volume ratio of between 200 and 500 cm$^{-1}$. In embodiments, the vaccine thin film has a surface area to volume ratio of between 300 and 500 cm$^{-1}$. In embodiments, the vaccine thin film has a surface area to volume ratio of between 400 and 500 cm$^{-1}$. In embodiments, the vaccine thin film has a surface area to volume ratio of between 100 and 400 cm$^{-1}$. In embodiments, the vaccine thin film has a surface area to volume ratio of between 200 and 300 cm$^{-1}$. In embodiments, the vaccine thin film has a surface area to volume ratio of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 cm$^{-1}$. In embodiments, the vaccine thin film has a surface area to volume ratio of between about 25 and about 500 cm$^{-1}$. In embodiments, the vaccine thin film has a surface area to volume ratio of between about 25 and about 400 cm$^{-1}$. In embodiments, the vaccine thin film has a surface area to volume ratio of between about 25 and about 300 cm$^{-1}$. In embodiments, the vaccine thin film has a surface area to volume ratio of between about 25 and about 200 cm$^{-1}$. In embodiments, the vaccine thin film has a surface area to volume ratio of between about 25 and about 100 cm$^{-1}$. In embodiments, the vaccine thin film has a surface area to volume ratio of between about 100 and about 500 cm$^{-1}$. In embodiments, the vaccine thin film has a surface area to volume ratio of between about 200 and about 500 cm$^{-1}$. In embodiments, the vaccine thin film has a surface area to volume ratio of between about 300 and about 500 cm$^{-1}$. In embodiments, the vaccine thin film has a surface area to volume ratio of between about 400 and about 500 cm$^{-1}$. In embodiments, the vaccine thin film has a surface area to volume ratio of between about 100 and about 400 cm$^{-1}$. In embodiments, the vaccine thin film has a surface area to volume ratio of between about 200 and about 300 cm$^{-1}$.

In embodiments, the freezing rate of the droplets is between about 10 K/second and about $10^5$ K/second. In embodiments, the freezing rate of the droplets is between about 10 K/second and about $10^4$ K/second. In embodiments, the freezing rate of the droplets is between about 10 K/second and about $10^3$ K/second. In embodiments, the freezing rate of the droplets is between about $10^2$ K/second and about $10^3$ K/second. In embodiments, the freezing rate of the droplets is between about 50 K/second and about $5\times10^2$ K/second. In embodiments, the freezing rate of the droplets is between 10 K/second and $10^5$ K/second. In embodiments, the freezing rate of the droplets is between 10 K/second and $10^4$ K/second. In embodiments, the freezing rate of the droplets is between 10 K/second and $10^3$ K/second. In embodiments, the freezing rate of the droplets is between $10^2$ K/second and $10^3$ K/second. In embodiments, the freezing rate of the droplets is between 50 K/second and $5\times10^2$ K/second. In embodiments, the freezing rate of the droplets is about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 K/second. In embodiments, the freezing rate of the droplets is 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 K/second. In embodiments, each of the droplets freezes upon contact with the freezing surface in less than about 50, 75, 100, 125, 150, 175, 200, 250, 500, 1,000, or 2,000 milliseconds. In embodiments, each of the droplets freezes upon contact with the freezing surface in less than 50, 75, 100, 125, 150, 175, 200, 250, 500, 1,000, or 2,000 milliseconds.

In embodiments, the droplets have an average diameter between about 0.1 and about 5 mm, between about 20 and about 24 degrees Celsius. In embodiments, the droplets have an average diameter between about 2 and about 4 mm, between about 20 and about 24 degrees Celsius. In embodiments, the droplets have an average diameter between about 1 and about 4 mm, between about 20 and about 24 degrees Celsius. In embodiments, the droplets have an average diameter between about 2 and about 3 mm, between about 20 and about 24 degrees Celsius. In embodiments, the droplets have an average diameter between about 1 and about 3 mm, between about 20 and about 24 degrees Celsius. In embodiments, the droplets have an average diameter between about 1 and about 2 mm, between about 20 and about 24 degrees Celsius. In embodiments, the droplets have an average diameter between about 3 and about 4 mm, between about 20 and about 24 degrees Celsius. In embodiments, the droplets have an average diameter between 0.1 and 5 mm, between 20 and 24 degrees Celsius. In embodiments, the droplets have an average diameter between 2 and 4 mm, between 20 and 24 degrees Celsius. In embodiments, the droplets have an average diameter between 1 and 4 mm, between 20 and 24 degrees Celsius. In embodiments, the droplets have an average diameter between 2 and 3 mm, between 20 and 24 degrees Celsius. In embodiments, the droplets have an average diameter between 1 and 3 mm, between 20 and 24 degrees Celsius. In embodiments, the droplets have an average diameter between 1 and 2 mm, between 20 and 24 degrees Celsius. In embodiments, the droplets have an average diameter between 3 and 4 mm, between 20 and 24 degrees Celsius.

In embodiments, the step of spraying or dripping droplets is repeated to overlay one or more additional vaccine thin films on top of the vaccine thin film. In embodiments, the step of spraying or dripping droplets is repeated to overlay 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 additional vaccine thin films on top of the first vaccine thin film.

In embodiments, the method further includes removing the solvent (e.g. water or liquid) from the vaccine thin film to form a dry vaccine.

In embodiments, is a method of making a dry vaccine from a vaccine thin film (e.g. including a vaccine thin film made using a method as described herein), including removing the solvent (e.g. water or liquid) from the vaccine thin film to form a dry vaccine. In embodiments of the methods described herein, the dry vaccine is a dry vaccine as described herein, including in an aspect, embodiment, example, table, figure, or claim. In embodiments, a method of making a vaccine thin film or a method of making dry vaccine is used to make a dry vaccine as described herein, including in an aspect, embodiment, example, table, figure, or claim.

In embodiments, the removing of the solvent includes lyophilization. In embodiments, the removing of the solvent includes lyophilization at temperatures of 20 degrees Celsius or less. In embodiments, the removing of the solvent includes lyophilization at temperatures of 25 degrees Celsius or less. In embodiments, the solvent includes lyophilization at temperatures of 40 degrees Celsius or less. In embodiments, the removing of the solvent includes lyophilization at temperatures of 50 degrees Celsius or less. In embodiments, the removing of the solvent includes lyophilization at temperatures of about 20 degrees Celsius or less. In embodiments, the removing of the solvent includes lyophilization at temperatures of about 25 degrees Celsius or less. In embodiments, the solvent includes lyophilization at temperatures of about 40 degrees Celsius or less. In embodiments, the removing of the solvent includes lyophilization at temperatures of about 50 degrees Celsius or less.

In embodiments, the dry vaccine includes between about 0.5 and about 5% (wt/wt) of the aluminum adjuvant. In embodiments, the dry vaccine includes between about 0.5 and about 4% (wt/wt) of the aluminum adjuvant. In embodiments, the dry vaccine includes between about 0.5 and about 3% (wt/wt) of the aluminum adjuvant. In embodiments, the dry vaccine includes between about 0.5 and about 2% (wt/wt) of the aluminum adjuvant. In embodiments, the dry vaccine includes between about 0.75 and about 2% (wt/wt) of the aluminum adjuvant. In embodiments, the dry vaccine includes between about 1 and about 2% (wt/wt) of the aluminum adjuvant. In embodiments, the dry vaccine includes between 0.5 and 5% (wt/wt) of the aluminum adjuvant. In embodiments, the dry vaccine includes between 0.5 and 4% (wt/wt) of the aluminum adjuvant. In embodiments, the dry vaccine includes between 0.5 and 3% (wt/wt) of the aluminum adjuvant. In embodiments, the dry vaccine includes between 0.5 and 2% (wt/wt) of the aluminum adjuvant. In embodiments, the dry vaccine includes between 0.75 and 2% (wt/wt) of the aluminum adjuvant. In embodiments, the dry vaccine includes between 1 and 2% (wt/wt) of the aluminum adjuvant. In embodiments, the dry vaccine includes about 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes at least 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes less than 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes at least about 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes less than about 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant.

In embodiments, the method further includes solvating the dry vaccine thereby forming a reconstituted liquid vaccine. A reconstituted liquid vaccine may also be called a solvated dry vaccine.

In embodiments, is a method of making a reconstituted liquid vaccine from a dry vaccine (e.g. including a dry vaccine made using a method as described herein), including solvating a dry vaccine and thereby forming a reconstituted liquid vaccine. In embodiments of the methods described herein, the dry vaccine is a dry vaccine as described herein, including in an aspect, embodiment, example, table, figure, or claim. In embodiments, a method of making a vaccine thin film, a method of making a dry vaccine, or a method of reconstituting a liquid vaccine is used to make a reconstituted liquid vaccine as described herein, including in an aspect, embodiment, example, table, figure, or claim.

In embodiments, the immunogenicity of the reconstituted liquid vaccine is at least 60% the immunogenicity of the liquid vaccine (prior to forming the dry vaccine from the liquid vaccine). In embodiments, the immunogenicity of the reconstituted liquid vaccine is at least 70% the immunogenicity of the liquid vaccine (prior to forming the dry vaccine from the liquid vaccine). In embodiments, the immunogenicity of the reconstituted liquid vaccine is at least 80% the immunogenicity of the liquid vaccine (prior to forming the dry vaccine from the liquid vaccine). In embodiments, the immunogenicity of the reconstituted liquid vaccine is at least 90% the immunogenicity of the liquid vaccine (prior to forming the dry vaccine from the liquid vaccine). In embodiments, the immunogenicity of the reconstituted liquid vaccine is at least 95% the immunogenicity of the liquid vaccine (prior to forming the dry vaccine from the liquid vaccine). In embodiments, the immunogenicity of the reconstituted liquid vaccine is at least about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% the immunogenicity of the liquid vaccine (prior to forming the dry vaccine from the liquid vaccine). In embodiments, the immunogenicity of the reconstituted liquid vaccine is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% the immunogenicity of the liquid vaccine (prior to forming the dry vaccine from the liquid vaccine).

In embodiments, the level of antigenic protein adsorbed to the aluminum adjuvant of the reconstituted liquid vaccine is at least 60% of the level of antigenic protein adsorbed to the aluminum adjuvant of the liquid vaccine (prior to forming the dry vaccine from the liquid vaccine). In embodiments, the level of antigenic protein adsorbed to the aluminum adjuvant of the reconstituted liquid vaccine is at least 70% of the level of antigenic protein adsorbed to the aluminum adjuvant of the liquid vaccine (prior to forming the dry vaccine from the liquid vaccine). In embodiments, the level of antigenic protein adsorbed to the aluminum adjuvant of the reconstituted liquid vaccine is at least 80% of the level of antigenic protein adsorbed to the aluminum adjuvant of the liquid vaccine (prior to forming the dry vaccine from the liquid vaccine). In embodiments, the level of antigenic protein adsorbed to the aluminum adjuvant of the reconstituted liquid vaccine is at least 90% of the level of antigenic protein adsorbed to the aluminum adjuvant of the liquid vaccine (prior to forming the dry vaccine from the liquid vaccine). In embodiments, the level of antigenic protein adsorbed to the aluminum adjuvant of the reconstituted liquid vaccine is at least 95% of the level of antigenic protein adsorbed to the aluminum adjuvant of the liquid vaccine (prior to forming the dry vaccine from the liquid vaccine). In embodiments, the level of antigenic protein adsorbed to the aluminum adjuvant of the reconstituted liquid vaccine is at least 99% of the level of antigenic protein adsorbed to the aluminum adjuvant of the liquid vaccine (prior to forming the dry vaccine from the liquid vaccine). In embodiments, the level of antigenic protein adsorbed to the aluminum adjuvant of the reconstituted liquid vaccine is at least about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the level of antigenic protein adsorbed to the aluminum adjuvant of the liquid vaccine (prior to forming the dry vaccine from the liquid vaccine). In embodiments, the level of antigenic protein adsorbed to the aluminum adjuvant of the reconstituted liquid vaccine is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the level of antigenic protein adsorbed to the aluminum adjuvant of the liquid vaccine (prior to forming the dry vaccine from the liquid vaccine).

In embodiments, the reconstituted liquid vaccine includes particles, wherein the particles include the antigenic protein adsorbed to the aluminum adjuvant. In embodiments, the particles have an average diameter of between about 10 nm and about 2 μm. In embodiments, the particles have an average diameter of between about 20 nm and about 2 μm.

In embodiments, the particles have an average diameter of between about 50 nm and about 2 μm. In embodiments, the particles have an average diameter of between about 100 nm and about 2 μm. In embodiments, the particles have an average diameter of between about 200 nm and about 2 μm. In embodiments, the particles have an average diameter of between about 500 nm and about 2 μm. In embodiments, the particles have an average diameter of between about 1 μm and about 2 μm. In embodiments, the particles have an average diameter of between about 10 nm and about 1 μm. In embodiments, the particles have an average diameter of between about 10 nm and about 500 nm. In embodiments, the particles have an average diameter of between about 10 nm and about 200 nm. In embodiments, the particles have an average diameter of between about 10 nm and about 100 nm. In embodiments, the particles have an average diameter of between about 10 nm and about 50 nm. In embodiments, the particles have an average diameter of between about 10 nm and about 20 nm. In embodiments, the particles have an average diameter of between about 20 nm and about 1 μm. In embodiments, the particles have an average diameter of between about 50 nm and about 500 nm. In embodiments, the particles have an average diameter of between about 100 nm and about 500 nm. In embodiments, the particles have an average diameter of between about 100 nm and about 200 nm. In embodiments, the reconstituted liquid vaccine includes particles, wherein the particles include the antigenic protein adsorbed to the aluminum adjuvant. In embodiments, the particles have an average diameter of between 10 nm and 2 μm. In embodiments, the particles have an average diameter of between 20 nm and 2 μm. In embodiments, the particles have an average diameter of between 50 nm and 2 μm. In embodiments, the particles have an average diameter of between 100 nm and 2 μm. In embodiments, the particles have an average diameter of between 200 nm and 2 μm. In embodiments, the particles have an average diameter of between 500 nm and 2 μum. In embodiments, the particles have an average diameter of between 1 μm and 2 μm. In embodiments, the particles have an average diameter of between 10 nm and 1 μm. In embodiments, the particles have an average diameter of between 10 nm and 500 nm. In embodiments, the particles have an average diameter of between 10 nm and 200 nm. In embodiments, the particles have an average diameter of between 10 nm and 200 nm. In embodiments, the particles have an average diameter of between 10 nm and 100 nm. In embodiments, the particles have an average diameter of between 10 nm and 50 nm. In embodiments, the particles have an average diameter of between 10 nm and 20 nm. In embodiments, the particles have an average diameter of between 20 nm and 1 μm. In embodiments, the particles have an average diameter of between 50 nm and 500 nm. In embodiments, the particles have an average diameter of between 100 nm and 500 nm. In embodiments, the particles have an average diameter of between 100 nm and 200 nm. In embodiments, the particles are non-crystalline. In embodiments, the particles are amorphous.

In embodiments, the particles have an average diameter of between about 1 μm and about 50 μm. In embodiments, the particles have an average diameter of between about 10 μm and about 50 μm. In embodiments, the particles have an average diameter of between about 20 μm and about 50 μm. In embodiments, the particles have an average diameter of between about 30 μm and about 50 μm. In embodiments, the particles have an average diameter of between about 40 μm and about 50 μm. In embodiments, the particles have an average diameter of between about 10 μm and about 40 μm. In embodiments, the particles have an average diameter of between about 10 μm and about 30 μm. In embodiments, the particles have an average diameter of between about 10 μm and about 20 μm. In embodiments, the particles have an average diameter of between about 1 μm and about 10 μm. In embodiments, the particles have an average diameter of between 1 μm and 50 μm. In embodiments, the particles have an average diameter of between 10 μm and 50 μm. In embodiments, the particles have an average diameter of between 20 μm and 50 μm. In embodiments, the particles have an average diameter of between 30 μm and 50 μm. In embodiments, the particles have an average diameter of between 40 μm and 50 μm. In embodiments, the particles have an average diameter of between 10 μm and 40 μm. In embodiments, the particles have an average diameter of between 10 μm and 30 μm. In embodiments, the particles have an average diameter of between 10 μm and 20 μm. In embodiments, the particles have an average diameter of between 1 μm and 10 μm. In embodiments, the particles have an average diameter of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 μm. In embodiments, the particles have an average diameter of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 μm.

In embodiments, the reconstituted liquid vaccine includes particles including antigenic protein adsorbed to the aluminum adjuvant of the same average diameter as the liquid vaccine (prior to forming the dry vaccine from the liquid vaccine) particles including antigenic protein adsorbed to the aluminum adjuvant. In embodiments, the reconstituted liquid vaccine includes particles including antigenic protein adsorbed to the aluminum adjuvant having an average diameter within 5% of the average diameter of particles including the antigenic protein adsorbed to the aluminum adjuvant in the liquid vaccine (prior to forming the dry vaccine from the liquid vaccine). In embodiments, the reconstituted liquid vaccine includes particles including antigenic protein adsorbed to the aluminum adjuvant having an average diameter within 10% of the average diameter of particles including the antigenic protein adsorbed to the aluminum adjuvant in the liquid vaccine (prior to forming the dry vaccine from the liquid vaccine). In embodiments, the reconstituted liquid vaccine includes particles including antigenic protein adsorbed to the aluminum adjuvant having an average diameter within 20% of the average diameter of particles including the antigenic protein adsorbed to the aluminum adjuvant in the liquid vaccine (prior to forming the dry vaccine from the liquid vaccine). In embodiments, the reconstituted liquid vaccine includes particles including antigenic protein adsorbed to the aluminum adjuvant having an average diameter within 30% of the average diameter of particles including the antigenic protein adsorbed to the aluminum adjuvant in the liquid vaccine (prior to forming the dry vaccine from the liquid vaccine). In embodiments, the reconstituted liquid vaccine includes particles including antigenic protein adsorbed to the aluminum adjuvant having an average diameter within about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% of the average diameter of particles including the antigenic protein adsorbed to the aluminum adjuvant in the liquid vaccine (prior to forming the dry vaccine from the liquid vaccine). In embodiments, the reconstituted liquid vaccine includes particles including antigenic protein adsorbed to the aluminum adjuvant having an average diameter within 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% of the average diameter of particles including the antigenic protein adsorbed to the aluminum adjuvant in the liquid vaccine (prior to forming the dry vaccine from the liquid vaccine).

In embodiments, the solvating of the dry vaccine is at least one day after preparing the dry vaccine from the liquid vaccine (e.g. the dry vaccine is stored for at least one day). In embodiments, the solvating of the dry vaccine is at least two days after preparing the dry vaccine from the liquid vaccine (e.g. the dry vaccine is stored for at least two days). In embodiments, the solvating of the dry vaccine is at least three days after preparing the dry vaccine from the liquid vaccine (e.g. the dry vaccine is stored for at least three days). In embodiments, the solvating of the dry vaccine is at least one week after preparing the dry vaccine from the liquid vaccine (e.g. the dry vaccine is stored for at least one week). In embodiments, the solvating of the dry vaccine is at least two weeks after preparing the dry vaccine from the liquid vaccine (e.g. the dry vaccine is stored for at least two weeks). In embodiments, the solvating of the dry vaccine is at least one month after preparing the dry vaccine from the liquid vaccine (e.g. the dry vaccine is stored for at least one month). In embodiments, the solvating of the dry vaccine is at least two months after preparing the dry vaccine from the liquid vaccine(e.g. the dry vaccine is stored for at least two months). In embodiments, the solvating of the dry vaccine is at least three months after preparing the dry vaccine from the liquid vaccine (e.g. the dry vaccine is stored for at least three months). In embodiments, the solvating of the dry vaccine is at least six months after preparing the dry vaccine from the liquid vaccine (e.g. the dry vaccine is stored for at least six months). In embodiments, the solvating of the dry vaccine is at least one year after preparing the dry vaccine from the liquid vaccine (e.g. the dry vaccine is stored for at least one year). In embodiments, the solvating of the dry vaccine is at least two years after preparing the dry vaccine from the liquid vaccine (e.g. the dry vaccine is stored for at least two years). In embodiments, the solvating of the dry vaccine is at least three years after preparing the dry vaccine from the liquid vaccine (e.g. the dry vaccine is stored for at least three years). In embodiments, the solvating of the dry vaccine is at least five years after preparing the dry vaccine from the liquid vaccine (e.g. the dry vaccine is stored for at least five years). In embodiments, the solvating of the dry vaccine is at least ten years after preparing the dry vaccine from the liquid vaccine (e.g. the dry vaccine is stored for at least ten years).

In embodiments, prior to the solvating of the dry vaccine, the dry vaccine is stored at about 4 degrees Celsius for at least 99% of the time. In embodiments, prior to the solvating of the dry vaccine, the dry vaccine is stored at less than 4 degrees Celsius for at least 99% of the time. In embodiments, prior to the solvating of the dry vaccine, the dry vaccine is stored at less than 0 degrees Celsius for at least 99% of the time. In embodiments, prior to the solvating of the dry vaccine, the dry vaccine is stored at less than −20 degrees Celsius for at least 99% of the time. In embodiments, prior to the solvating of the dry vaccine, the dry vaccine is stored at about −20 degrees Celsius for at least 99% of the time. In embodiments, prior to the solvating of the dry vaccine, the dry vaccine is stored at less than −80 degrees Celsius for at least 99% of the time. In embodiments, prior to the solvating of the dry vaccine, the dry vaccine is stored at about −80 degrees Celsius for at least 99% of the time. In embodiments, prior to the solvating of the dry vaccine, the dry vaccine is stored at ambient temperatures (e.g. room temperature). In embodiments, prior to the solvating of the dry vaccine, the dry vaccine is stored at between 20 and 24 degrees Celsius for at least 99% of the time. In embodiments, prior to the solvating of the dry vaccine, the dry vaccine is stored at between 4 and 24 degrees Celsius for at least 99% of the time. In embodiments, prior to the solvating of the dry vaccine, the dry vaccine is stored at between 0 and 24 degrees Celsius for at least 99% of the time. In embodiments, prior to the solvating of the dry vaccine, the dry vaccine is stored at between 4 and 40 degrees Celsius for at least 99% of the time. In embodiments, prior to the solvating of the dry vaccine, the dry vaccine is stored at between 0 and 40 degrees Celsius for at least 99% of the time. In embodiments, prior to the solvating of the dry vaccine, the dry vaccine is stored at about 4 degrees Celsius for at least 90% of the time. In embodiments, prior to the solvating of the dry vaccine, the dry vaccine is stored at less than 4 degrees Celsius for at least 90% of the time. In embodiments, prior to the solvating of the dry vaccine, the dry vaccine is stored at less than 0 degrees Celsius for at least 90% of the time. In embodiments, prior to the solvating of the dry vaccine, the dry vaccine is stored at less than −20 degrees Celsius for at least 90% of the time. In embodiments, prior to the solvating of the dry vaccine, the dry vaccine is stored at between 20 and 24 degrees Celsius for at least 90% of the time. In embodiments, prior to the solvating of the dry vaccine, the dry vaccine is stored at between 4 and 24 degrees Celsius for at least 90% of the time. In embodiments, prior to the solvating of the dry vaccine, the dry vaccine is stored at between 0 and 24 degrees Celsius for at least 90% of the time. In embodiments, prior to the solvating of the dry vaccine, the dry vaccine is stored at between 4 and 40 degrees Celsius for at least 90% of the time. In embodiments, prior to the solvating of the dry vaccine, the dry vaccine is stored at between 0 and 40 degrees Celsius for at least 90% of the time.

In embodiments, upon solvating the dry vaccine the resulting reconstituted liquid vaccine remains homogeneous. As used in reference to the status of a reconstituted liquid vaccine, the term "homogenous" refers to a lack of a significant amount of aggregation and/or precipitation forming, such that the reconstituted liquid vaccine does not include solid matter that is not evenly dispersed (e.g. solid matter visible to the naked eye, solid matter that settles in the liquid, solid matter that was not apparent in a liquid vaccine prior to formation of the dry vaccine and reconstitution, precipitate that was not present in the liquid vaccine prior to formation of the dry vaccine). A homogenous reconstituted liquid sample may include particles of antigenic protein adsorbed to aluminum adjuvant (e.g. that are suspended or dispersed in the reconstituted liquid vaccine). In embodiments, upon solvating the dry vaccine the resulting reconstituted liquid vaccine remains homogeneous for at least one day. In embodiments, upon solvating the dry vaccine the resulting reconstituted liquid vaccine remains homogeneous for at least two days. In embodiments, upon solvating the dry vaccine the resulting reconstituted liquid vaccine remains homogeneous for at least three days. In embodiments, upon solvating the dry vaccine the resulting reconstituted liquid vaccine remains homogeneous for at least one week. In embodiments, upon solvating the dry vaccine the resulting reconstituted liquid vaccine remains homogeneous for at least two weeks. In embodiments, upon solvating the dry vaccine the resulting reconstituted liquid vaccine remains homogeneous for at least one month. In embodiments, upon solvating the dry vaccine the resulting reconstituted liquid vaccine remains homogeneous for at least three months. In embodiments, upon solvating the dry vaccine the resulting reconstituted liquid vaccine remains homogeneous for at least six months. In embodiments, upon solvating the dry vaccine the resulting reconstituted liquid vaccine remains homogeneous for at least one year. In embodiments, upon solvating the dry vaccine the resulting reconstituted liquid vaccine does not form a precipitate (e.g. solid matter visible to the naked eye, solid matter that settles in the liquid, solid matter that was not apparent in a liquid vaccine prior to formation of the dry vaccine and reconstitution, precipitate that was not present in the liquid vaccine prior to formation of the dry vaccine). In embodiments, upon solvating the dry vaccine the resulting reconstituted liquid vaccine does not form a precipitate for at least one day. In embodiments, upon solvating the dry vaccine the resulting reconstituted liquid vaccine does not form a precipitate for at least two days. In embodiments, upon solvating the dry vaccine the resulting reconstituted liquid vaccine does not form a precipitate for at least three days. In embodiments, upon solvating the dry vaccine the resulting reconstituted liquid vaccine does not form a precipitate for at least one week. In embodiments, upon solvating the dry vaccine the resulting reconstituted liquid vaccine does not form a precipitate for at least two weeks. In embodiments, upon solvating the dry vaccine the resulting reconstituted liquid vaccine does not form a precipitate for at least one month. In embodiments, upon solvating the dry vaccine the resulting reconstituted liquid vaccine does not form a precipitate for at least three months. In embodiments, upon solvating the dry vaccine the resulting reconstituted liquid vaccine does not form a precipitate for at least six months. In embodiments, upon solvating the dry vaccine the resulting reconstituted liquid vaccine does not form a precipitate for at least one year. In embodiments, the precipitate includes particles having an average diameter greater than 50 µm. In embodiments, the precipitate includes particles having an average diameter greater than 100 µm. In embodiments, the precipitate includes particles having an average diameter greater than 200 µm. In embodiments, the precipitate includes particles having an average diameter greater than 300 µm. In embodiments, the precipitate includes particles having an average diameter greater than 400 µm. In embodiments, the precipitate includes particles having an average diameter greater than 500 µm. In embodiments, the precipitate includes particles having an average diameter greater than 600 µm. In embodiments, the precipitate includes particles having an average diameter greater than 700 µm. In embodiments, the precipitate includes particles having an average diameter greater than 800 µm. In embodiments, the precipitate includes particles having an average diameter greater than 900 µm. In embodiments, the precipitate includes particles having an average diameter greater than 1000 µm. In embodiments, the precipitate includes particles having an average diameter greater than about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µm. In embodiments, the precipitate includes particles having an average diameter of about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µm. In embodiments, the precipitate includes particles having an average diameter greater than 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µm. In embodiments, the precipitate (that is not formed) includes particles having an average diameter of 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µm. In embodiments, the precipitate (that is not formed) includes at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the total antigenic protein absorbed to an aluminum adjuvant in the reconstituted liquid vaccine. In embodiments, upon solvating the dry vaccine the resulting reconstituted liquid vaccine does not form a precipitate including more than about 1% of the total antigenic protein in the reconstituted liquid vaccine. In embodiments, upon solvating the dry vaccine the resulting reconstituted liquid vaccine does not form a precipitate including more than about 2% of the total antigenic protein in the reconstituted liquid vaccine. In embodiments, upon solvating the dry vaccine the resulting reconstituted liquid vaccine does not form a precipitate including more than about 3% of the total antigenic protein in the reconstituted liquid vaccine. In embodiments, upon solvating the dry vaccine the resulting reconstituted liquid vaccine does not form a precipitate including more than about 4% of the total antigenic protein in the reconstituted liquid vaccine. In embodiments, upon solvating the dry vaccine the resulting reconstituted liquid vaccine does not form a precipitate including more than about 5% of the total antigenic protein in the reconstituted liquid vaccine. In embodiments, upon solvating the dry vaccine the resulting reconstituted liquid vaccine does not form a precipitate including more than about 1, 2, 3, 4, 5, 6, 7, 8, 9, 10, 11, 12, 13, 14, 15, 16, 17, 18, 19, or 20% of the total antigenic protein in the reconstituted liquid vaccine. In embodiments the precipitate includes irreversible aggregates of antigenic protein and/or aluminum adjuvant.

In embodiments, the liquid vaccine includes a commercially available vaccine. In embodiments, the liquid vaccine is a commercially available vaccine. In embodiments, the liquid vaccine has received market approval from the US FDA or the corresponding authority in another country. In embodiments, the liquid vaccine is a vaccine for the treatment of diphtheria, tetanus, pertussis, influenza, pneumonia, otitis media, bacteremia, meningitis, hepatitis, cirrhosis, anthrax poisoning, botulism, rabies, warts, poliomyelitis, Japanese encephalitis, or cancer. In embodiments, the liquid vaccine is a vaccine for the treatment of infection by *Clostridium tetani, Clostridium botulinum, Streptococcus pneumonia*, Hepatitis A, Hepatitis B, *Haemophilus influenza, Corynebacterium diphtheria, Bordetella pertussis, Human papillomavirus, Bacillus anthracis*, Rabies virus, Japanese encephalitis virus, or Poliovirus. In embodiments, the liquid vaccine includes a commercially available vaccine and another component not included in the commercially available vaccine (e.g. an excipient (e.g. trehalose)).

In an aspect is provided a method of treating a disease in a patient in need of such treatment, the method including administering a therapeutically effective amount of a solvated dry vaccine as described herein (e.g. in an aspect, embodiment, example, table, figure, or claims) (e.g. a reconstituted liquid vaccine as described herein) to the patient.

In embodiments, the disease is diphtheria, tetanus, pertussis, influenza, pneumonia, otitis media, bacteremia, meningitis, hepatitis, cirrhosis, anthrax poisoning, rabies, warts, poliomyelitis, Japanese encephalitis, or cancer. In embodiments, the disease is caused by an infectious agent. In embodiments, the infectious agent is a bacterium. In embodiments, the infectious agent is a virus. In embodiments, the infectious agent is *Clostridium tetani, Clostridium botulinum, Streptococcus pneumonia*, Hepatitis A, Hepatitis B, *Haemophilus influenza, Corynebacterium diphtheria, Bordetella pertussis, Human papillomavirus, Bacillus anthracis*, Rabies virus, Japanese encephalitis virus, or Poliovirus.

In an aspect is provided a method of treating a disease in a patient in need of such treatment, the method including administering a therapeutically effective amount of dry vaccine as described herein (e.g. in an aspect, embodiment, example, table, figure, or claims) (e.g. a reconstituted liquid vaccine as described herein) to the patient.

In embodiments, the disease is diphtheria, tetanus, pertussis, influenza, pneumonia, otitis media, bacteremia, meningitis, hepatitis, cirrhosis, anthrax poisoning, botulism, rabies, warts, poliomyelitis, Japanese encephalitis, or cancer. In embodiments, the disease is caused by an infectious agent. In embodiments, the infectious agent is a bacterium. In embodiments, the infectious agent is a virus. In embodiments, the infectious agent is *Clostridium tetani, Clostridium botulinum, Streptococcus pneumonia*, Hepatitis A, Hepatitis B, *Haemophilus influenza, Corynebacterium diphtheria, Bordetella pertussis, Human papillomavirus, Bacillus anthracis*, Rabies virus, Japanese encephalitis virus, or Poliovirus.

In embodiments, the dry vaccine is administered by inhalation, intradermally, orally, or vaginally. In embodiments, the dry vaccine is administered through the nasal mucosa, bronchoalveolar mucosa, or gastrointestinal mucosa.

In embodiments, the method is a method described herein, including in an aspect, embodiment, example, table, figure, or claim. Provided herein is a method of preparing a dry vaccine including a method of preparing a vaccine thin film as described herein (including in an aspect, embodiment, example, table, figure, or claim) and a method of removing a solvent from a vaccine thin film as described herein (including in an aspect, embodiment, example, table, figure, or claim). Provided herein is a method of preparing a reconstituted dry vaccine including a method of preparing a dry vaccine as described herein (including in an aspect, embodiment, example, table, figure, or claim), a method of preparing a vaccine thin film as described herein (including in an aspect, embodiment, example, table, figure, or claim) and a method of removing a solvent from a vaccine thin film as described herein (including in an aspect, embodiment, example, table, figure, or claim).

In embodiments, to form a powder vaccine, an aqueous vaccine composition is first frozen to form a frozen vaccine composition, then the frozen water is removed to form the vaccine powder. A fast freezing process is used to form the frozen vaccine composition. A fast freezing process, as used herein, is a process that can freeze a thin film of liquid (less than about 500 microns) in a time of less than or equal to one second. Examples of fast freezing processes that may be used include thin film freezing (TFF), spray freeze-drying (SFD), or spray freezing into liquids (SFL). In the TFF process liquid droplets fall from a given height and impact, spread, and freeze on a cooled solid substrate. Typically, the substrate is a metal drum that is cooled to below 250° K, or below 200° K or below 150° K. On impact the droplets that are deformed into thin films freeze in a time of between about 70 ms and 1000 ms. The frozen thin films may be removed from the substrate by a stainless steel blade mounted along the rotating drum surface. The frozen thin films are collected in liquid nitrogen to maintain in the frozen state. Further details regarding thin film freezing processes may be found in the paper to Engstrom et al. "Formation of Stable Submicron Protein Particles by Thin Film Freezing" Pharmaceutical Research, Vol. 25, No. 6, June 2008, 1334-1346, which is incorporated herein by reference.

Water (e.g. frozen water) is removed from the frozen vaccine composition to produce a vaccine powder. Water (e.g. frozen water) may be removed by a lyophilization process or a freeze-drying process. Water may also be removed by an atmospheric freeze-drying process.

The resulting vaccine powder can be readily reconstituted to form a stable dispersion without significant loss of stability or activity. The vaccine powder may be transported and stored in a wide range of temperatures without concern of accidental exposure to freezing conditions. In addition, the vaccine powder may also be stored at room temperature, which will potentially decrease the costs of vaccines. In fact, it is generally less costly to transport dry solid powder than liquid.

Currently human vaccines (e.g. marketed and/or approved human vaccines, such as FDA approved human vaccines) that have aluminum-containing adjuvant are all administered by needle-syringe-based injections. It would be beneficial to patients and the healthcare system if the vaccines were administered non-invasively without hypodermic needles. Our dried aluminum-containing vaccine powder can potentially be administered by an alternative route such as, but not limited to, inhalation as a dried powder, intradermally using a solid jet injection device (e.g., powder jet injector), orally in tablets or capsules, buccally in buccal tablets or films, or vaginally using a special vaginal drug delivery device. The above-mentioned routes of administration are not only more convenient and friendly to patients, but more importantly they can enable the induction of mucosal immune responses. Functional antibodies in the mucosal secretion (e.g., nasal mucus, bronchoalveolar mucus, or the gastrointestinal mucus) of a host can effectively neutralize pathogens or toxins even before they enter the host.

Described herein are compositions and methods for preparing a vaccine thin film or a dry vaccine by spraying or dripping droplets of a liquid vaccine (e.g. aluminum adjuvant containing) such that the antigenic protein adsorbed to the aluminum adjuvant in the liquid vaccine (e.g. aluminum adjuvant containing) is exposed to an vapor-liquid interface of less than 500 cm$^{-1}$ area/volume (e.g. less than 50, 100, 150, 200, 250, 300, 400) and contacting the droplet with a freezing surface having a temperature lower than the freezing temperature of the liquid vaccine (e.g. aluminum adjuvant containing) (e.g. has a temperature differential of at least 30° C. between the droplet and the surface), wherein the surface freezes the droplet into a thin film with a thickness of less than 500 micrometers (e.g. less than 450, 400, 350, 300, 250, 200, 150, 100, or 50 micrometers) and a surface area to volume between 25 to 500 cm$^{-1}$. In embodiments, the method may further include the step of removing the liquid (e.g. solvent, water) from the frozen material to form a dry vaccine (e.g. particles). In embodiments, the droplets freeze upon contact with the surface in less than 50, 75, 100, 125, 150, 175, 200, 250, 500, 1,000 or 2,000 milliseconds. In embodiments, the droplets freeze upon contact with the surface in less than 50 or 150 milliseconds. In embodiments, the droplet has a diameter between 2 and 5 mm at room temperature. In embodiments, the droplet forms a thin film on the freezing surface of between 50 and 500 micrometers in thickness. In embodiments, the droplets have a cooling rate of between 50-250 K/s. In embodiments, the particles of the dry vaccine, after liquid (e.g. solvent or water) removal, have a surface area of at least 10, 15, 25, 50, 75, 100, 125, 150 or 200 m$^2$/gr (e.g. surface area of 10, 15, 25, 50, 75, 100, 125, 150 or 200 m$^2$/gr). Minimizing gas-liquid interface can improve protein stability by limiting the amount of protein that can adsorb to the interface.

In embodiments, the droplets may be delivered to the cold or freezing surface in a variety of manners and configurations. In embodiments, the droplets may be delivered in parallel, in series, at the center, middle or periphery or a platen, platter, plate, roller, conveyor surface. In embodiments, the freezing or cold surface may be a roller, a belt, a solid surface, circular, cylindrical, conical, oval and the like that permit for the droplet to freeze. For a continuous process a belt, platen, plate or roller may be particularly useful. In embodiments, the frozen droplets may form beads, strings, films or lines of frozen liquid vaccine. In embodiments, the effective ingredient is removed from the surface with a scraper, wire, ultrasound or other mechanical separator prior to the lyophilization process. Once the material is removed from the surface of the belt, platen, roller or plate the surface is free to receive additional material.

In embodiments, the surface is cooled by a cryogenic solid, a cryogenic gas, a cryogenic liquid or a heat transfer fluid capable of reaching cryogenic temperatures or temperatures below the freezing point of the liquid vaccine (e.g. at least 30° C. less than the temperature of the droplet). In embodiments, the liquid vaccine further includes one or more excipients selected from sugars, phospholipids, surfactants, polymeric surfactants, vesicles, polymers, including copolymers and homopolymers and biopolymers, dispersion aids, and serum albumin. In embodiments, aggregation of the antigenic protein is less than 3% of the total antigenic protein in the vaccine (e.g. irreversible aggregation). In embodiments, the temperature differential between the droplet and the surface is at least 50° C. In embodiments, the excipients or stabilizers that can be included in the liquid vaccines that are to be frozen as described herein include: cryoprotectants, lyoprotectants, surfactants, fillers, stabilizers, polymers, protease inhibitors, antioxidants and absorption enhancers. Specific nonlimiting examples of excipients that may be included in the vaccines described herein include: sucrose, trehaolose, Span 80, Tween 80, Brij 35, Brij 98, Pluronic, sucroester 7, sucroester 11, sucroester 15, sodium lauryl sulfate, oleic acid, laureth-9, laureth-8, lauric acid, vitamin E TPGS, Gelucire 50/13, Gelucire 53/10, Labrafil, dipalmitoyl phosphadityl choline, glycolic acid and salts, deoxycholic acid and salts, sodium fusidate, cyclodextrins, polyethylene glycols, labrasol, polyvinyl alcohols, polyvinyl pyrrolidones and tyloxapol.

In embodiments, the method may further include the step of removing the liquid (e.g. solvent or water) from the frozen liquid vaccine to form a dry vaccine. In embodiments, the solvent further includes at least one or more excipient or stabilizers selected from, e.g., sugars, phospholipids, surfactants, polymeric surfactants, vesicles, polymers, including copolymers and homopolymers and biopolymers, dispersion aids, and serum albumin. In embodiments, the temperature differential between the solvent and the surface is at least 50° C.

In embodiments, the resulting powder can be redispersed into a suitable aqueous medium such as saline, buffered saline, water, buffered aqueous media, solutions of amino acids, solutions of vitamins, solutions of carbohydrates, or the like, as well as combinations of any two or more thereof, to obtain a suspension that can be administered to mammals (e.g. humans).

In embodiments, is described a single-step, single-vial method for preparing a vaccine thin film or dry vaccine by reducing the temperature of a vial wherein the vial has a temperature below the freezing temperature of a liquid vaccine (e.g. a temperature differential of at least 30° C. between the liquid vaccine and the vial) and spraying or dripping droplets of a liquid vaccine directly into the vial such that the antigenic protein of the liquid vaccine is exposed to a vapor-liquid interface of less than 500 cm$^{-1}$ area/volume, wherein the surface freezes the droplet into a thin film with a thickness of less than 500 micrometers and a surface area to volume between 25 to 500 cm$^{-1}$. In embodiments, the droplets freeze upon contact with the surface in less than about 50, 75, 100, 125, 150, 175, 200, 250, 500, 1,000 or 2,000 milliseconds (e.g. in about 50, 75, 100, 125, 150, 175, 200, 250, 500, 1,000 or 2,000 milliseconds), and may freeze upon contact with the surface in about 50 or 150 to 500 milliseconds. In embodiments, a droplet has a diameter between 0.1 and 5 mm at room temperature (e.g. a diameter between 2 and 4 mm at room temperature). In embodiments, the droplet forms a thin film on the surface of between 50 and 500 micrometers in thickness. In embodiments, the droplets have a cooling rate of between 50-250 K/s. In embodiments, the vial may be cooled by a cryogenic solid, a cryogenic gas, a cryogenic liquid, a freezing fluid, a freezing gas, a freezing solid, a heat exchanger, or a heat transfer fluid capable of reaching cryogenic temperatures or temperatures below the freezing point of the liquid vaccine. In embodiments, the vial may be rotated as the spraying or droplets are delivered to permit the layering or one or more layers of the liquid vaccine. In embodiments, the vial and the liquid vaccine are pre-sterilized prior to spraying or dripping. In embodiments, the step of spraying or dripping is repeated to overlay one or more thin films on top of each other to fill the vial to any desired level up to totally full.

D. Additional Embodiments

1p. A method of making a powder vaccine comprising:
  obtaining an aqueous vaccine composition, the vaccine composition comprising an agent that resembles a disease-causing microorganism or a compound associated with the disease-causing microorganism and an adjuvant;

freezing the vaccine composition to obtain a frozen vaccine composition; and converting the frozen vaccine composition into a dry powder comprising the agent or compound and the adjuvant.

2p. The method of embodiment 1p, wherein the adjuvant is an aluminum-containing adjuvant.

3p. The method of embodiment 1p, wherein the vaccine composition comprises a killed microorganism.

4p. The method of embodiment 1p, wherein the vaccine composition comprises live, attenuated microorganisms.

5p. The method of embodiment 1p, wherein the vaccine composition comprises a bacterial toxin.

6p. The method of embodiment 1p, wherein the vaccine composition comprises a protein subunit.

7p The method of embodiment 1p, wherein the vaccine composition comprises a conjugate.

8p. The method of embodiment 1p, wherein the vaccine composition comprises a cryoprotectant.

9p. The method of embodiment 1p, wherein freezing the vaccine composition comprises: forming a droplet of the vaccine composition; applying the droplet to a cooled surface, wherein the surface is at a temperature sufficient to freeze the vaccine composition in a time of less than or equal to about 1 second; removing the frozen vaccine composition from the surface.

10p. The method of embodiment 9p, further comprising removing water from the frozen vaccine composition to create a vaccine powder.

11p. The method of embodiment 8p, wherein removing the water is done by a lyophilization process.

12p. The method of embodiment 8p, wherein removing the water is done by freeze-drying process.

13p. A powder vaccine made by the process of any one of embodiments 1p-12p, wherein the powder vaccine comprises an agent that resembles a disease-causing microorganism or a compound associated with the disease-causing microorganism and an adjuvant.

14p. A method of administering a vaccine to a subject comprising: obtaining a powder vaccine as described in embodiment 13p; and administering the powder vaccine to the subject.

15p. The method of embodiment 14p, wherein the vaccine is administered by inhalation of the powder vaccine.

16p. The method of embodiment 14p, wherein the vaccine is administered by: adding water to the powder vaccine to create an aqueous vaccine composition comprising the powder vaccine; and injecting the vaccine composition in the subject.

17p. A vaccine composition comprising an agent that resembles a disease-causing microorganism or a compound associated with the disease-causing microorganism and an aluminum adjuvant having an average particle size of less than 200 nm.

18p. A method of making a reconstituted vaccine composition comprising: obtaining an aqueous vaccine composition, the vaccine composition comprising an agent that resembles a disease-causing microorganism or a compound associated with the disease-causing microorganism and an adjuvant;

freezing the vaccine composition to obtain a frozen vaccine composition; converting the frozen vaccine composition into a dry powder comprising the agent or compound and the adjuvant; adding an aqueous reconstitution agent to the powder vaccine to create the reconstituted vaccine composition.

19p. The method of embodiment 18p, wherein the aqueous reconstitution agent is water.

20p. The method of embodiment 18p, wherein the aqueous reconstitution agent is a saline solution.

21p. The method of embodiment 18p, wherein the aqueous reconstitution agent is an aqueous buffer solution.

22p. The method of embodiment 18p, wherein the reconstituted vaccine composition has a stability and efficacy/activity that is substantially the same as the stability and efficacy/activity of the aqueous vaccine composition.

23p. The method of embodiment 18p, wherein the reconstituted vaccine composition is suitable for injection.

24p. The method of embodiment 18p, wherein the reconstituted vaccine composition is suitable for inhalation.

1. A dry vaccine comprising:
an antigenic protein and an aluminum adjuvant, wherein at least 75% of said antigenic protein is adsorbed to said aluminum adjuvant.

2. The dry vaccine of embodiment 1, wherein at least 60% of said antigenic protein is not denatured.

3. The dry vaccine of embodiment 1, wherein at least 70% of said antigenic protein is not denatured.

4. The dry vaccine of embodiment 1, wherein at least 80% of said antigenic protein is not denatured.

5. The dry vaccine of embodiment 1, wherein at least 90% of said antigenic protein is not denatured.

6. The dry vaccine of embodiment 1, wherein at least 95% of said antigenic protein is not denatured.

7. The dry vaccine of one of embodiments 1 to 6, wherein said aluminum adjuvant is aluminum hydroxide.

8. The dry vaccine of one of embodiments 1 to 6, wherein said aluminum adjuvant is aluminum phosphate.

9. The dry vaccine of one of embodiments 1 to 6, wherein said aluminum adjuvant is aluminum sulfate.

10. The dry vaccine of one of embodiments 1 to 6, wherein said aluminum adjuvant is potassium aluminum sulfate.

11. The dry vaccine of one of embodiments 1 to 10 comprising less than 4% water.

12. The dry vaccine of one of embodiments 1 to 10 comprising less than 3% water.

13. The dry vaccine of one of embodiments 1 to 10 comprising less than 2% water.

14. The dry vaccine of one of embodiments 1 to 10 comprising less than 1% water.

15. The dry vaccine of one of embodiments 1 to 14, wherein at least 80% of said antigenic protein is adsorbed to said aluminum adjuvant.

16. The dry vaccine of one of embodiments 1 to 14, wherein at least 85% of said antigenic protein is adsorbed to said aluminum adjuvant.

17. The dry vaccine of one of embodiments 1 to 14, wherein at least 90% of said antigenic protein is adsorbed to said aluminum adjuvant.

18. The dry vaccine of one of embodiments 1 to 14, wherein at least 92% of said antigenic protein is adsorbed to said aluminum adjuvant.

19. The dry vaccine of one of embodiments 1 to 14, wherein at least 95% of said antigenic protein is adsorbed to said aluminum adjuvant.

20. The dry vaccine of one of embodiments 1 to 14, wherein at least 98% of said antigenic protein is adsorbed to said aluminum adjuvant.

21. The dry vaccine of one of embodiments 1 to 14, wherein at least 99% of said antigenic protein is adsorbed to said aluminum adjuvant.

22. The dry vaccine of one of embodiments 1 to 21, further comprising an excipient.

23. The dry vaccine of embodiment 22, wherein said excipient is a salt, sugar, buffer, detergent, polymer, amino acid, or preservative.
24. The dry vaccine of embodiment 22, wherein said excipient is disodium edetate, sodium chloride, sodium citrate, sodium succinate, sodium hydroxide, Sodium glucoheptonate, sodium acetyltryptophanate, sodium bicarbonate, sodium caprylate, sodium pertechnetate, sodium acetate, sodium dodecyl sulfate, ammonium citrate, calcium chloride, calcium, potassium chloride, potassium sodium tartarate, zinc oxide, zinc, stannous chloride, magnesium sulfate, magnesium stearate, titanium dioxide, DL-lactic/glycolic acids, asparagine, L-arginine, arginine hydrochloride, adenine, histidine, glycine, glutamine, glutathione, imidazole, protamine, protamine sulfate, phosphoric acid, Tri-n-butyl phosphate, ascorbic acid, cysteine hydrochloride, hydrochloric acid, hydrogen citrate, trisodium citrate, guanidine hydrochloride, mannitol, lactose, sucrose, agarose, sorbitol, maltose, trehalose, surfactants, polysorbate 80, polysorbate 20, poloxamer 188, sorbitan monooleate, triton n101, m-cresol, benyl alcohol, ethanolamine, glycerin, phosphorylethanolamine, tromethamine, 2-phenyl oxyethanol, chlorobutanol, dimethylsulfoxide, N-methyl-2-pyrrolidone, propyleneglycol, polyoxyl 35 castor oil, methyl hydroxybenzoate, tromethamine, corn oil-mono-di-triglycerides, poloxyl 40 hydrogenated castor oil, tocopherol, n-acetyltryptophan, octa-fluoropropane, castor oil, polyoxyethylated oleic glycerides, polyoxyethylated castor oil, phenol, glyclyglycine, thimerosal, parab ens, gelatin, Formaldehyde, Dulbecco's modified eagles medium, hydrocortisone, neomycin, Von Willebrand factor, gluteraldehyde, benzethonium chloride, white petroleum, p-aminopheyl-p-anisate, monosodium glutamate, beta-propiolactone, acetate, citrate, glutamate, glycinate, histidine, Lactate, Maleate, phosphate, succinate, tartrate, tris, carbomer 1342 (copolymer of acrylic acid and a long chain alkyl methacrylate cross-linked with allyl ethers of pentaerythritol), glucose star polymer, silicone polymer, polydimethylsiloxane, polyethylene glycol, polyvinylpyrrolidone, carboxymethylcellulose, poly(glycolic acid), poly(lactic-co-glycolic acid), polylactic acid, dextran 40, or poloxamer.
25. The dry vaccine of embodiment 22, wherein said excipient is trehalose.
26. The dry vaccine of one of embodiments 22 to 25, comprising less than 5% wt/wt of said excipient.
27. The dry vaccine of one of embodiments 22 to 25, comprising less than 4% wt/wt of said excipient.
28. The dry vaccine of one of embodiments 22 to 25, comprising less than 3% wt/wt of said excipient.
29. The dry vaccine of one of embodiments 22 to 25, comprising less than 2% wt/wt of said excipient.
30. The dry vaccine of one of embodiments 22 to 25, comprising less than 1% wt/wt of said excipient.
31. The dry vaccine of one of embodiments 22 to 25, comprising less than 0.5% wt/wt of said excipient.
32. The dry vaccine of one of embodiments 1 to 31, comprising between 0.5 and 5% (wt/wt) of said aluminum adjuvant.
33. The dry vaccine of one of embodiments 1 to 31, comprising between 0.5 and 3% (wt/wt) of said aluminum adjuvant.
34. The dry vaccine of one of embodiments 1 to 31, comprising between 0.5 and 2% (wt/wt) of said aluminum adjuvant.
35. The dry vaccine of one of embodiments 1 to 31, comprising between 0.75 and 2% (wt/wt) of said aluminum adjuvant.
36. The dry vaccine of one of embodiments 1 to 31, comprising between 1 and 2% (wt/wt) of said aluminum adjuvant.
37. The dry vaccine of one of embodiments 1 to 36 comprising particles, wherein said particles comprise said antigenic protein adsorbed to said aluminum adjuvant.
38. The dry vaccine of one of embodiments 1 to 37, wherein said dry vaccine is prepared from a liquid vaccine.
39. A method for preparing a vaccine thin film comprising: applying a liquid vaccine to a freezing surface; allowing said liquid vaccine to disperse and freeze on said freezing surface thereby forming a vaccine thin film.
40. The method of embodiment 39, wherein said liquid vaccine comprises an aluminum adjuvant.
41. The method of embodiment 40, wherein said aluminum adjuvant in said liquid vaccine comprises aluminum hydroxide.
42. The method of embodiment 40, wherein said aluminum adjuvant in said liquid vaccine comprises aluminum phosphate.
43. The method of embodiment 40, wherein said aluminum adjuvant in said liquid vaccine comprises aluminum sulfate.
44. The method of embodiment 40, wherein said aluminum adjuvant in said liquid vaccine comprises aluminum potassium sulfate.
45. The method of one of embodiments 40 to 44, wherein said liquid vaccine comprises about 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine.
46. The method of one of embodiments 40 to 44, wherein said liquid vaccine comprises 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine.
47. The method of one of embodiments 40 to 44, wherein said liquid vaccine comprises at least 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine.
48. The method of one of embodiments 40 to 44, wherein said liquid vaccine comprises less than 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine.
49. The method of one of embodiments 40 to 44, wherein said liquid vaccine comprises between about 0.08 and about 1% (wt/vol) of the aluminum adjuvant/liquid vaccine.
50. The method of one of embodiments 40 to 44, wherein said liquid vaccine comprises between about 0.5 and about 5% (wt/vol) of the aluminum adjuvant/liquid vaccine.
51. The method of one of embodiments 40 to 44, wherein said liquid vaccine comprises between about 0.5 and about 4% (wt/vol) of the aluminum adjuvant/liquid vaccine.
52. The method of one of embodiments 40 to 44, wherein said liquid vaccine comprises between about 0.5 and about 3% (wt/vol) of the aluminum adjuvant/liquid vaccine.
53. The method of one of embodiments 40 to 44, wherein said liquid vaccine comprises between about 0.5 and about 2% (wt/vol) of the aluminum adjuvant/liquid vaccine.

54. The method of one of embodiments 40 to 44, wherein said liquid vaccine comprises between about 0.5 and about 1% (wt/vol) of the aluminum adjuvant/liquid vaccine.

55. The method of one of embodiments 40 to 44, wherein said liquid vaccine comprises between about 1 and about 2% (wt/vol) of the aluminum adjuvant/liquid vaccine.

56. The method of one of embodiments 40 to 44, wherein said liquid vaccine comprises between 0.08 and 1% (wt/vol) of the aluminum adjuvant/liquid vaccine.

57. The method of one of embodiments 40 to 44, wherein said liquid vaccine comprises between 0.5 and 5% (wt/vol) of the aluminum adjuvant/liquid vaccine.

58. The method of one of embodiments 40 to 44, wherein said liquid vaccine comprises between 0.5 and 4% (wt/vol) of the aluminum adjuvant/liquid vaccine.

59. The method of one of embodiments 40 to 44, wherein said liquid vaccine comprises between 0.5 and 3% (wt/vol) of the aluminum adjuvant/liquid vaccine.

60. The method of one of embodiments 40 to 44, wherein said liquid vaccine comprises between 0.5 and 2% (wt/vol) of the aluminum adjuvant/liquid vaccine.

61. The method of one of embodiments 40 to 44, wherein said liquid vaccine comprises between 0.5 and 1% (wt/vol) of the aluminum adjuvant/liquid vaccine.

62. The method of one of embodiments 40 to 44, wherein said liquid vaccine comprises between 1 and 2% (wt/vol) of the aluminum adjuvant/liquid vaccine.

63. The method of one of embodiments 39 to 62, wherein said liquid vaccine comprises an excipient.

64. The method of embodiment 63, wherein said excipient in said liquid vaccine is a salt, sugar (saccharide), buffer, detergent, polymer, amino acid, or preservative.

65. The method of embodiment 63, wherein said excipient in said liquid vaccine is disodium edetate, sodium chloride, sodium citrate, sodium succinate, sodium hydroxide, Sodium glucoheptonate, sodium acetyltryptophanate, sodium bicarbonate, sodium caprylate, sodium pertechnetate, sodium acetate, sodium dodecyl sulfate, ammonium citrate, calcium chloride, calcium, potassium chloride, potassium sodium tartarate, zinc oxide, zinc, stannous chloride, magnesium sulfate, magnesium stearate, titanium dioxide, DL-lactic/glycolic acids, asparagine, L-arginine, arginine hydrochloride, adenine, histidine, glycine, glutamine, glutathione, imidazole, protamine, protamine sulfate, phosphoric acid, Tri-n-butyl phosphate, ascorbic acid, cysteine hydrochloride, hydrochloric acid, hydrogen citrate, trisodium citrate, guanidine hydrochloride, mannitol, lactose, sucrose, agarose, sorbitol, maltose, trehalose, surfactants, polysorbate 80, polysorbate 20, poloxamer 188, sorbitan monooleate, triton n101, m-cresol, benyl alcohol, ethanolamine, glycerin, phosphorylethanolamine, tromethamine, 2-phenyloxyethanol, chlorobutanol, dimethylsulfoxide, N-methyl-2-pyrrolidone, propyleneglycol, polyoxyl 35 castor oil, methyl hydroxybenzoate, tromethamine, corn oil-mono-di-triglycerides, poloxyl 40 hydrogenated castor oil, tocopherol, n-acetyltryptophan, octa-fluoropropane, castor oil, polyoxyethylated oleic glycerides, polyoxytethylated castor oil, phenol, glyclyglycine, thimerosal, parabens, gelatin, Formaldehyde, Dulbecco's modified eagles medium, hydrocortisone, neomycin, Von Willebrand factor, gluteraldehyde, benzethonium chloride, white petroleum, p-aminopheyl-p-anisate, monosodium glutamate, beta-propiolactone, acetate, citrate, glutamate, glycinate, histidine, Lactate, Maleate, phosphate, succinate, tartrate, tris, carbomer 1342 (copolymer of acrylic acid and a long chain alkyl methacrylate cross-linked with allyl ethers of pentaerythritol), glucose star polymer, silicone polymer, polydimethylsiloxane, polyethylene glycol, polyvinylpyrrolidone, carboxymethylcellulose, poly(glycolic acid), poly(lactic-co-glycolic acid), polylactic acid, dextran 40, or poloxamer.

66. The method of embodiment 63, wherein said excipient in said liquid vaccine is trehalose.

67. The method of one of embodiments 63 to 66, wherein said liquid vaccine comprises less than 5% wt/vol of said excipient/liquid vaccine.

68. The method of one of embodiments 63 to 66, wherein said liquid vaccine comprises less than 4% wt/vol of said excipient/liquid vaccine.

69. The method of one of embodiments 63 to 66, wherein said liquid vaccine comprises less than 3% wt/vol of said excipient/liquid vaccine.

70. The method of one of embodiments 63 to 66, wherein said liquid vaccine comprises less than 2% wt/vol of said excipient/liquid vaccine.

71. The method of one of embodiments 63 to 66, wherein said liquid vaccine comprises less than 1% wt/vol of said excipient/liquid vaccine.

72. The method of one of embodiments 63 to 66, wherein said liquid vaccine comprises less than 0.5% wt/vol of said excipient/liquid vaccine.

73. The method of one of embodiments 63 to 66, wherein said liquid vaccine comprises about 5% wt/vol of said excipient/liquid vaccine.

74. The method of one of embodiments 63 to 66, wherein said liquid vaccine comprises about 4% wt/vol of said excipient/liquid vaccine.

75. The method of one of embodiments 63 to 66, wherein said liquid vaccine comprises about 3% wt/vol of said excipient/liquid vaccine.

76. The method of one of embodiments 63 to 66, wherein said liquid vaccine comprises about 2% wt/vol of said excipient/liquid vaccine.

77. The method of one of embodiments 63 to 66, wherein said liquid vaccine comprises about 1% wt/vol of said excipient/liquid vaccine.

78. The method of one of embodiments 63 to 66, wherein said liquid vaccine comprises about 0.5% wt/vol of said excipient/liquid vaccine.

79. The method of one of embodiments 63 to 66, wherein said liquid vaccine comprises about 0.1, 0.2, 0.3, 0.4, 0.5, 0.6, 0.7, 0.8, 0.9, 1, 2, 3, 4, 5, 6, 7, 8, 9, or 10% (wt/vol) of said excipient/liquid vaccine.

80. The method of one of embodiments 63 to 66, wherein said liquid vaccine comprises 0.1, 0.2, 0.3, 0.4, 0.5, 0.6, 0.7, 0.8, 0.9, 1, 2, 3, 4, 5, 6, 7, 8, 9, or 10% (wt/vol) of said excipient/liquid vaccine.

81. The method of one of embodiments 39 to 80, wherein said applying comprises spraying or dripping droplets of said liquid vaccine.

82. The method of embodiment 81, wherein the vapor-liquid interfaces of said droplets are less than 500 $cm^{-1}$ area/volume 83. The method of one of embodiments 81 to 82, further comprising contacting the droplets with a freezing surface having a temperature differential of at least 30° C. between the droplets and the surface.
84. The method of one of embodiments 39 to 83, wherein the vaccine thin film has a thickness of less than 500 micrometers.

85. The method of one of embodiments 39 to 84, wherein the vaccine thin film has a surface area to volume ratio of between 25 and 500 cm$^{-1}$.
86. The method of one of embodiments 81 to 85, wherein the freezing rate of said droplets is between 10 K/second and $10^5$ K/second.
87. The method of one of embodiments 81 to 85, wherein the freezing rate of said droplets is between 10 K/second and $10^4$ K/second.
88. The method of one of embodiments 81 to 85, wherein the freezing rate of said droplets is between 10 K/second and $10^3$ K/second.
89. The method of one of embodiments 81 to 85, wherein the freezing rate of said droplets is between $10^2$ K/second and $10^3$ K/second.
90. The method of one of embodiments 81 to 85, wherein the freezing rate of said droplets is between 50 K/second and $5 \times 10^2$ K/second.
91. The method of one of embodiments 81 to 90, wherein each of said droplets freezes upon contact with the freezing surface in less than 50, 75, 100, 125, 150, 175, 200, 250, 500, 1,000, or 2,000 milliseconds.
92. The method of one of embodiments 81 to 91, wherein said droplets have an average diameter between 0.1 and 5 mm, between 20 and 24 degrees Celsius.
93. The method of one of embodiments 81 to 91, wherein said droplets have an average diameter between 2 and 4 mm, between 20 and 24 degrees Celsius.
94. The method of one of embodiments 39 to 93, wherein said vaccine thin film has a thickness of less than 250 micrometers.
95. The method of one of embodiments 39 to 93, wherein said vaccine thin film has a thickness of less than 100 micrometers.
96. The method of one of embodiments 39 to 93, wherein said vaccine thin film has a thickness of less than 50 micrometers.
97. The method of one of embodiments 81 to 96, wherein said droplet vapor-liquid interface is less than 250 cm$^{-1}$ area/volume.
98. The method of one of embodiments 81 to 96, wherein said droplet vapor-liquid interface is less than 100 cm$^{-1}$ area/volume.
99. The method of one of embodiments 81 to 98, wherein the step of spraying or dripping droplets is repeated to overlay one or more additional vaccine thin films on top of the vaccine thin film.
100. The method of one of embodiments 39 to 99, further comprising removing the solvent from the vaccine thin film to form a dry vaccine.
101. The method of embodiment 100, wherein said dry vaccine comprises an antigenic protein and an aluminum adjuvant, wherein at least 75% of said antigenic protein is adsorbed to said aluminum adjuvant.
102. The method of embodiment 101, wherein at least 60% of said antigenic protein is not denatured.
103. The method of embodiment 101, wherein at least 70% of said antigenic protein is not denatured.
104. The method of embodiment 101, wherein at least 80% of said antigenic protein is not denatured.
105. The method of embodiment 101, wherein at least 90% of said antigenic protein is not denatured.
106. The method of embodiment 101, wherein at least 95% of said antigenic protein is not denatured.
107. The method of one of embodiments 101 to 106, wherein said dry vaccine comprises between 0.5 and 5% (wt/wt) of said aluminum adjuvant.
108. The method of one of embodiments 101 to 106, wherein said dry vaccine comprises between 0.5 and 4% (wt/wt) of said aluminum adjuvant.
109. The method of one of embodiments 101 to 106, wherein said dry vaccine comprises between 0.5 and 3% (wt/wt) of said aluminum adjuvant.
110. The method of one of embodiments 101 to 106, wherein said dry vaccine comprises between 0.5 and 2% (wt/wt) of said aluminum adjuvant.
111. The method of one of embodiments 101 to 106, wherein said dry vaccine comprises between 0.75 and 2% (wt/wt) of said aluminum adjuvant.
112. The method of one of embodiments 101 to 106, wherein said dry vaccine comprises between 1 and 2% (wt/wt) of said aluminum adjuvant.
113. The method of one of embodiments 101 to 112, wherein said aluminum adjuvant is aluminum hydroxide.
114. The method of one of embodiments 101 to 112, wherein said aluminum adjuvant is aluminum phosphate.
115. The method of one of embodiments 101 to 112, wherein said aluminum adjuvant is aluminum sulfate.
116. The method of one of embodiments 101 to 112, wherein said aluminum adjuvant is potassium aluminum sulfate.
117. The method of one of embodiments 100 to 116 wherein said dry vaccine comprises less than 4% water.
118. The method of one of embodiments 100 to 116 wherein said dry vaccine comprises less than 3% water.
119. The method of one of embodiments 100 to 116 wherein said dry vaccine comprises less than 2% water.
120. The method of one of embodiments 100 to 116 wherein said dry vaccine comprises less than 1% water.
121. The method of one of embodiments 101 to 120, wherein at least 80% of said antigenic protein is adsorbed to said aluminum adjuvant.
122. The method of one of embodiments 101 to 120, wherein at least 85% of said antigenic protein is adsorbed to said aluminum adjuvant.
123. The method of one of embodiments 101 to 120, wherein at least 90% of said antigenic protein is adsorbed to said aluminum adjuvant.
124. The method of one of embodiments 101 to 120, wherein at least 92% of said antigenic protein is adsorbed to said aluminum adjuvant.
125. The method of one of embodiments 101 to 120, wherein at least 95% of said antigenic protein is adsorbed to said aluminum adjuvant.
126. The method of one of embodiments 101 to 120, wherein at least 98% of said antigenic protein is adsorbed to said aluminum adjuvant.
127. The method of one of embodiments 101 to 120, wherein at least 99% of said antigenic protein is adsorbed to said aluminum adjuvant.
128. The method of one of embodiments 101 to 127, wherein said dry vaccine comprises an excipient.
129. The method of embodiment 128, wherein said excipient is a salt, sugar, buffer, detergent, polymer, amino acid, or preservative.
130. The method of embodiment 128, wherein said excipient is disodium edetate, sodium chloride, sodium citrate, sodium succinate, sodium hydroxide, Sodium glucoheptonate, sodium acetyltryptophanate, sodium bicarbonate, sodium caprylate, sodium pertechnetate, sodium acetate, sodium dodecyl sulfate, ammonium citrate, calcium chloride, calcium, potassium chloride, potassium sodium tartarate, zinc oxide, zinc, stannous chloride, magnesium sulfate, magnesium stearate, titanium dioxide, DL-lactic/glycolic acids, asparagine, L-arginine, arginine hydrochloride, adenine, histidine, glycine, glutamine, gluta-thione, imidazole, protamine, protamine sulfate, phosphoric acid, Tri-n-butyl phosphate, ascorbic acid, cysteine hydrochloride, hydrochloric acid, hydrogen citrate, trisodium citrate, guanidine hydrochloride, mannitol, lactose, sucrose, agarose, sorbitol, maltose, trehalose, surfactants, polysorbate 80, polysorbate 20, poloxamer 188, sorbitan monooleate, triton n101, m-cresol, benyl alcohol, ethanolamine, glycerin, phosphoryletha-nolamine, tromethamine, 2-phenyl oxyethanol, chlorobu-tanol, dimethylsulfoxide, N-methyl-2-pyrrolidone, propyleneglycol, polyoxyl 35 castor oil, methyl hydroxybenzoate, tromethamine, corn oil-mono-di-tri-glycerides, poloxyl 40 hydrogenated castor oil, tocoph-erol, n-acetyltryptophan, octa-fluoropropane, castor oil, polyoxyethylated oleic glycerides, polyoxyethylated castor oil, phenol, glyclyglycine, thimerosal, parab ens, gelatin, Formaldehyde, Dulbecco's modified eagles medium, hydrocortisone, neomycin, Von Willebrand factor, gluter-aldehyde, benzethonium chloride, white petroleum, p-aminopheyl-p-anisate, monosodium glutamate, beta-propiolactone, acetate, citrate, glutamate, glycinate, histidine, Lactate, Maleate, phosphate, succinate, tartrate, tris, carbomer 1342 (copolymer of acrylic acid and a long chain alkyl methacrylate cross-linked with allyl ethers of pentaerythritol), glucose star polymer, silicone polymer, polydimethylsiloxane, polyethylene glycol, polyvinylpyrrolidone, carboxymethylcellulose, poly(glycolic acid), poly(lactic-co-glycolic acid), polylactic acid, dextran 40, or poloxamer.
131. The method of embodiment 128, wherein said excipient is trehalose.
132. The method of one of embodiments 128 to 131, wherein said dry vaccine comprises less than 5% wt/wt of said excipient.
133. The method of one of embodiments 128 to 131, wherein said dry vaccine comprises less than 4% wt/wt of said excipient.
134. The method of one of embodiments 128 to 131, wherein said dry vaccine comprises less than 3% wt/wt of said excipient.
135. The method of one of embodiments 128 to 131, wherein said dry vaccine comprises less than 2% wt/wt of said excipient.
136. The method of one of embodiments 128 to 131, wherein said dry vaccine comprises less than 1% wt/wt of said excipient.
137. The method of one of embodiments 128 to 131, wherein said dry vaccine comprises less than 0.5% wt/wt of said excipient.
138. The method of one of embodiments 101 to 138 wherein said dry vaccine comprises particles, wherein said particles comprise said antigenic protein adsorbed to said aluminum adjuvant.
139. The method of one of embodiments 100 to 138, wherein said removing of the solvent comprises lyophilization.
140. The method of one of embodiments 100 to 139, wherein said removing of the solvent comprises lyophilization at temperatures of 20 degrees Celsius or less.
141. The method of one of embodiments 100 to 139, wherein said removing of the solvent comprises lyophilization at temperatures of 25 degrees Celsius or less.
142. The method of one of embodiments 100 to 139, wherein said removing of the solvent comprises lyophilization at temperatures of 40 degrees Celsius or less.
143. The method of one of embodiments 100 to 139, wherein said removing of the solvent comprises lyophilization at temperatures of 50 degrees Celsius or less.
144. The method of one of embodiments 100 to 143, further comprising solvating said dry vaccine thereby forming a reconstituted liquid vaccine.
145. The method of embodiment 144, wherein the immunogenicity of said reconstituted liquid vaccine is at least 60% the immunogenicity of said liquid vaccine.
146. The method of embodiment 144, wherein the immunogenicity of said reconstituted liquid vaccine is at least 70% the immunogenicity of said liquid vaccine.
147. The method of embodiment 144, wherein the immunogenicity of said reconstituted liquid vaccine is at least 80% the immunogenicity of said liquid vaccine.
148. The method of embodiment 144, wherein the immunogenicity of said reconstituted liquid vaccine is at least 90% the immunogenicity of said liquid vaccine.
149. The method of embodiment 144, wherein the immunogenicity of said reconstituted liquid vaccine is at least 95% the immunogenicity of said liquid vaccine.
150. The method of one of embodiments 144 to 149, wherein the level of antigenic protein adsorbed to said aluminum adjuvant of said reconstituted liquid vaccine is at least 60% of the level of antigenic protein adsorbed to said aluminum adjuvant of said liquid vaccine.
151. The method of one of embodiments 144 to 149, wherein the level of antigenic protein adsorbed to said aluminum adjuvant of said reconstituted liquid vaccine is at least 70% of the level of antigenic protein adsorbed to said aluminum adjuvant of said liquid vaccine.
152. The method of one of embodiments 144 to 149, wherein the level of antigenic protein adsorbed to said aluminum adjuvant of said reconstituted liquid vaccine is at least 80% of the level of antigenic protein adsorbed to said aluminum adjuvant of said liquid vaccine.
153. The method of one of embodiments 144 to 149, wherein the level of antigenic protein adsorbed to said aluminum adjuvant of said reconstituted liquid vaccine is at least 90% of the level of antigenic protein adsorbed to said aluminum adjuvant of said liquid vaccine.
154. The method of one of embodiments 144 to 149, wherein the level of antigenic protein adsorbed to said aluminum adjuvant of said reconstituted liquid vaccine is at least 95% of the level of antigenic protein adsorbed to said aluminum adjuvant of said liquid vaccine.
155. The method of one of embodiments 144 to 149, wherein the level of antigenic protein adsorbed to said aluminum adjuvant of said reconstituted liquid vaccine is at least 99% of the level of antigenic protein adsorbed to said aluminum adjuvant of said liquid vaccine.
156. The method of one of embodiments 144 to 155, wherein said reconstituted liquid vaccine comprises particles, wherein said particles comprise said antigenic protein adsorbed to said aluminum adjuvant.
157. The method of embodiment 156 wherein said particles have an average diameter of between 10 nm and 5 µm.
158. The method of embodiment 156 wherein said particles have an average diameter of between 1 µm and 5 µm.
159. The method of embodiment 156 wherein said particles have an average diameter of between 2 µm and 4 µm.
160. The method of embodiment 156 wherein said particles have an average diameter of between 1 µm and 3 µm.
161. The method of embodiment 156 wherein said particles have an average diameter of between 10 nm and 2 µm.
162. The method of embodiment 156 wherein said particles have an average diameter of between 20 nm and 2 µm.

163. The method of embodiment 156 wherein said particles have an average diameter of between 50 nm and 2 µm.
164. The method of embodiment 156 wherein said particles have an average diameter of between 100 nm and 2 µm.
165. The method of embodiment 156 wherein said particles have an average diameter of between 200 nm and 2 µm.
166. The method of embodiment 156 wherein said particles have an average diameter of between 500 nm and 2 µm.
167. The method of embodiment 156 wherein said particles have an average diameter of between 1 µm and 2 µm.
168. The method of embodiment 156 wherein said particles have an average diameter of between 10 nm and 1 µm.
169. The method of embodiment 156 wherein said particles have an average diameter of between 10 nm and 500 nm.
170. The method of embodiment 156 wherein said particles have an average diameter of between 10 nm and 200 nm.
171. The method of embodiment 156 wherein said particles have an average diameter of between 10 nm and 200 nm.
172. The method of embodiment 156 wherein said particles have an average diameter of between 10 nm and 100 nm.
173. The method of embodiment 156 wherein said particles have an average diameter of between 10 nm and 50 nm.
174. The method of embodiment 156 wherein said particles have an average diameter of between 10 nm and 20 nm.
175. The method of embodiment 156 wherein said particles have an average diameter of between 20 nm and 1 µm.
176. The method of embodiment 156 wherein said particles have an average diameter of between 50 nm and 500 nm.
177. The method of embodiment 156 wherein said particles have an average diameter of between 100 nm and 500 nm.
178. The method of embodiment 156 wherein said particles have an average diameter of between 100 nm and 200 nm.
179. The method of one of embodiments 144 to 178, wherein said reconstituted liquid vaccine comprises particles comprising antigenic protein adsorbed to said aluminum adjuvant of the same average diameter as the liquid vaccine particles comprising antigenic protein adsorbed to said aluminum adjuvant.
180. The method of one of embodiments 144 to 178, wherein said reconstituted liquid vaccine comprises particles comprising antigenic protein adsorbed to said aluminum adjuvant having an average diameter within 5% of the average diameter of particles comprising said antigenic protein adsorbed to said aluminum adjuvant in said liquid vaccine.
181. The method of one of embodiments 144 to 178, wherein said reconstituted liquid vaccine comprises particles comprising antigenic protein adsorbed to said aluminum adjuvant having an average diameter within 10% of the average diameter of particles comprising said antigenic protein adsorbed to said aluminum adjuvant in said liquid vaccine.
182. The method of one of embodiments 144 to 178, wherein said reconstituted liquid vaccine comprises particles comprising antigenic protein adsorbed to said aluminum adjuvant having an average diameter within 20% of the average diameter of particles comprising said antigenic protein adsorbed to said aluminum adjuvant in said liquid vaccine.
183. The method of one of embodiments 144 to 178, wherein said reconstituted liquid vaccine comprises particles comprising antigenic protein adsorbed to said aluminum adjuvant having an average diameter within 30% of the average diameter of particles comprising said antigenic protein adsorbed to said aluminum adjuvant in said liquid vaccine.
184. The method of one of embodiments 144 to 183, wherein said solvating of said dry vaccine is at least one day after preparing said dry vaccine from said liquid vaccine.
185. The method of one of embodiments 144 to 183, wherein said solvating of said dry vaccine is at least two days after preparing said dry vaccine from said liquid vaccine.
186. The method of one of embodiments 144 to 183, wherein said solvating of said dry vaccine is at least three days after preparing said dry vaccine from said liquid vaccine.
187. The method of one of embodiments 144 to 183, wherein said solvating of said dry vaccine is at least one week after preparing said dry vaccine from said liquid vaccine.
188. The method of one of embodiments 144 to 183, wherein said solvating of said dry vaccine is at least two weeks after preparing said dry vaccine from said liquid vaccine.
189. The method of one of embodiments 144 to 183, wherein said solvating of said dry vaccine is at least one month after preparing said dry vaccine from said liquid vaccine.
190. The method of one of embodiments 144 to 183, wherein said solvating of said dry vaccine is at least two months after preparing said dry vaccine from said liquid vaccine.
191. The method of one of embodiments 144 to 183, wherein said solvating of said dry vaccine is at least three months after preparing said dry vaccine from said liquid vaccine.
192. The method of one of embodiments 144 to 183, wherein said solvating of said dry vaccine is at least six months after preparing said dry vaccine from said liquid vaccine.
193. The method of one of embodiments 144 to 183, wherein said solvating of said dry vaccine is at least six months after preparing said dry vaccine from said liquid vaccine.
194. The method of one of embodiments 144 to 183, wherein said solvating of said dry vaccine is at least six months after preparing said dry vaccine from said liquid vaccine.
195. The method of one of embodiments 144 to 183, wherein said solvating of said dry vaccine is at least one year after preparing said dry vaccine from said liquid vaccine.
196. The method of one of embodiments 144 to 183, wherein said solvating of said dry vaccine is at least two years after preparing said dry vaccine from said liquid vaccine.
197. The method of one of embodiments 144 to 183, wherein said solvating of said dry vaccine is at least three years after preparing said dry vaccine from said liquid vaccine.
198. The method of one of embodiments 144 to 183, wherein said solvating of said dry vaccine is at least five years after preparing said dry vaccine from said liquid vaccine.
199. The method of one of embodiments 144 to 183, wherein said solvating of said dry vaccine is at least ten years after preparing said dry vaccine from said liquid vaccine.

200. The method of one of embodiments 144 to 199, wherein prior to said solvating of said dry vaccine, said dry vaccine is stored at about 4 degrees Celsius for at least 99% of the time.
201. The method of one of embodiments 144 to 199, wherein prior to said solvating of said dry vaccine, said dry vaccine is stored at less than 4 degrees Celsius for at least 99% of the time.
202. The method of one of embodiments 144 to 199, wherein prior to said solvating of said dry vaccine, said dry vaccine is stored at less than 0 degrees Celsius for at least 99% of the time.
203. The method of one of embodiments 144 to 199, wherein prior to said solvating of said dry vaccine, said dry vaccine is stored at less than −20 degrees Celsius for at least 99% of the time.
204. The method of one of embodiments 144 to 199, wherein prior to said solvating of said dry vaccine, said dry vaccine is stored at between 20 and 24 degrees Celsius for at least 99% of the time.
205. The method of one of embodiments 144 to 199, wherein prior to said solvating of said dry vaccine, said dry vaccine is stored at between 4 and 24 degrees Celsius for at least 99% of the time.
206. The method of one of embodiments 144 to 199, wherein prior to said solvating of said dry vaccine, said dry vaccine is stored at between 0 and 24 degrees Celsius for at least 99% of the time.
207. The method of one of embodiments 144 to 199, wherein prior to said solvating of said dry vaccine, said dry vaccine is stored at between 4 and 40 degrees Celsius for at least 99% of the time.
208. The method of one of embodiments 144 to 199, wherein prior to said solvating of said dry vaccine, said dry vaccine is stored at between 0 and 40 degrees Celsius for at least 99% of the time.
209. The method of one of embodiments 144 to 208, wherein upon solvating said dry vaccine the resulting reconstituted liquid vaccine remains homogeneous.
210. The method of one of embodiments 144 to 208, wherein upon solvating said dry vaccine the resulting reconstituted liquid vaccine remains homogeneous for at least one day.
211. The method of one of embodiments 144 to 208, wherein upon solvating said dry vaccine the resulting reconstituted liquid vaccine remains homogeneous for at least two days.
212. The method of one of embodiments 144 to 208, wherein upon solvating said dry vaccine the resulting reconstituted liquid vaccine remains homogeneous for at least three days.
213. The method of one of embodiments 144 to 208, wherein upon solvating said dry vaccine the resulting reconstituted liquid vaccine remains homogeneous for at least one week.
214. The method of one of embodiments 144 to 208, wherein upon solvating said dry vaccine the resulting reconstituted liquid vaccine remains homogeneous for at least two weeks.
215. The method of one of embodiments 144 to 208, wherein upon solvating said dry vaccine the resulting reconstituted liquid vaccine remains homogeneous for at least one month.
216. The method of one of embodiments 144 to 208, wherein upon solvating said dry vaccine the resulting reconstituted liquid vaccine remains homogeneous for at least three months.
217. The method of one of embodiments 144 to 208, wherein upon solvating said dry vaccine the resulting reconstituted liquid vaccine remains homogeneous for at least six months.
218. The method of one of embodiments 144 to 208, wherein upon solvating said dry vaccine the resulting reconstituted liquid vaccine remains homogeneous for at least one year.
219. The method of one of embodiments 144 to 218, wherein upon solvating said dry vaccine the resulting reconstituted liquid vaccine does not form a precipitate.
220. The method of one of embodiments 144 to 218, wherein upon solvating said dry vaccine the resulting reconstituted liquid vaccine does not form a precipitate for at least one day.
221. The method of one of embodiments 144 to 218, wherein upon solvating said dry vaccine the resulting reconstituted liquid vaccine does not form a precipitate for at least two days.
222. The method of one of embodiments 144 to 218, wherein upon solvating said dry vaccine the resulting reconstituted liquid vaccine does not form a precipitate for at least three days.
223. The method of one of embodiments 144 to 218, wherein upon solvating said dry vaccine the resulting reconstituted liquid vaccine does not form a precipitate for at least one week.
224. The method of one of embodiments 144 to 218, wherein upon solvating said dry vaccine the resulting reconstituted liquid vaccine does not form a precipitate for at least two weeks.
225. The method of one of embodiments 144 to 218, wherein upon solvating said dry vaccine the resulting reconstituted liquid vaccine does not form a precipitate for at least one month.
226. The method of one of embodiments 144 to 218, wherein upon solvating said dry vaccine the resulting reconstituted liquid vaccine does not form a precipitate for at least three months.
227. The method of one of embodiments 144 to 218, wherein upon solvating said dry vaccine the resulting reconstituted liquid vaccine does not form a precipitate for at least six months.
228. The method of one of embodiments 144 to 218, wherein upon solvating said dry vaccine the resulting reconstituted liquid vaccine does not form a precipitate for at least one year.
229. A method of treating a disease in a patient in need of such treatment, said method comprising administering a therapeutically effective amount of a solvated dry vaccine of one of embodiments 1 to 38 to said patient, wherein said disease is diphtheria, botulism, tetanus, pertussis, influenza, pneumonia, otitis media, bacteremia, meningitis, hepatitis, cirrhosis, anthrax poisoning, rabies, warts, poliomyelitis, Japanese encephalitis, or cancer.
230. A method of treating a disease caused by an infectious agent in a patient in need of such treatment, said method comprising administering a therapeutically effective amount of a solvated dry vaccine of one of embodiments 1 to 38 to said patient, wherein said infectious agent is *Clostridium tetani, Clostridium botulinum, Streptococcus pneumonia*, Hepatitis A, Hepatitis B, *Haemophilus influenza, Corynebacterium diphtheria, Bordetella pertussis, Human papillomavirus, Bacillus anthracis*, Rabies virus, Japanese encephalitis virus, or Poliovirus.

E. EXAMPLES

In the present study, using ovalbumin as a model antigen adsorbed onto aluminum hydroxide or aluminum phosphate, a commercially available vaccine (e.g. tetanus toxoid vaccine adjuvanted with aluminum potassium sulfate, a human hepatitis B vaccine adjuvanted with aluminum hydroxide) it was shown that vaccines containing a relatively high concentration of aluminum salts (~1%, w/v) can be converted into a dry powder by thin-film freezing followed by removal of the frozen solvent by lyophilization while using low levels of trehalose (i.e., as low as 2% w/v) as an excipient. Importantly, the thin-film freeze-drying process did not cause vaccine coagulation or aggregation and preserved the immunological potency of the vaccines. Moreover, repeated freezing-and-thawing of the dry vaccine powder did not cause aggregation or coagulation. Thin-film freeze drying is a viable platform technology to produce dry powder of vaccines that contain aluminum salts.

1. Lyophilization of Ovalbumin (OVA)-Adsorbed Aluminum Hydroxide Particles with 2% Trehalose (w/v) Under Different Freezing Rates.

OVA solution was initially mixed with aluminum hydroxide particles in suspension. Trehalose as a cryoprotectant was added in all samples at a final concentration of 2% (w/v). One sample of the suspension was treated to a high-speed thin-film freezing process. Briefly, the OVA-adsorbed aluminum hydroxide suspension was dropped onto a pre-cooled cryogenic substrate. The frozen film-like solids were collected in liquid nitrogen and dried using a VirTis Advantage bench top tray lyophilizer. Samples were also treated by using a slow freezing method. The OVA-adsorbed aluminum hydroxide suspension was frozen on a shelf at −20° C. or −80° C. overnight and then lyophilized in FreeZone plus 4.5 liter cascade console freeze dry system (Labconco corporation, Kansas city, Mo.). Particle size for all samples was determined using a Sympatec Helos laser diffraction instrument (Sympatec GmbH, Germany) equipped with a R3 lens. Images were taken using an Olympus BX60 microscope (Olympus America, Inc., Center Valley, Pa.).

Results are depicted in FIG. 1. Microscopic images of OVA-adsorbed aluminum hydroxide particles before freeze-drying (FIG. 1A) and after high speed thin-film freeze-drying and reconstitution (FIG. 1B), slow freezing at −20° C., drying and reconstitution (FIG. 1C), and slow freezing at −80° C., drying and reconstitution (FIG. 1D). As shown in FIG. 1A-B, the high-speed thin-film freezing method did not cause significant aggregation of the OVA-adsorbed aluminum hydroxide particles. The lyophilized powder was easily reconstituted in water, normal saline, or phosphate buffered saline (PBS). The size of freshly prepared OVA-adsorbed aluminum hydroxide particles was 9.4±1.7 µm, which is not different from the size of the lyophilized OVA-adsorbed aluminum hydroxide particles after reconstitution (9.7±2.5 µm). However, when the OVA-adsorbed aluminum hydroxide particles were lyophilized using lower freezing rates, significant aggregations occurred (FIG. 1C-1D).

2. The Binding Efficiency of OVA to the Aluminum Hydroxide Particles after Lyophilization.

SDS-PAGE was used to determine the binding efficiency of the OVA to aluminum hydroxide particles after lyophilization. Initially, OVA was mixed with aluminum hydroxide particles at 1 to 10 ratio (OVA vs. $Al^{3+}$, w/w) in a suspension with 2% (w/v) of trehalose. The OVA-adsorbed aluminum hydroxide particles were lyophilized using the thin-film freezing method, reconstituted in water, and applied on SDS-PAGE gel. As a control, OVA alone (OVA) or freshly prepared OVA-adsorbed aluminum hydroxide particles without lyophilization (NON TFF) were also included. Samples were mixed with Laemmli sample buffer (62.5 mM Tris-HCl, pH 6.8, 25% glycerol, 2% SDS, and 0.01% Bromophenol Blue) before applying to 7.5% Mini-PROTEAN® TGX™ precast polyacrylamide gels (Bio-Rad). Precision plus protein standards were also run along with the samples at 130 V for 1 h. The gel was then stained in a Bio-Safe Coomassie blue staining solution and scanned using a Kodak Image Station 440CF (Rochester, N.Y.).

Figure 2:
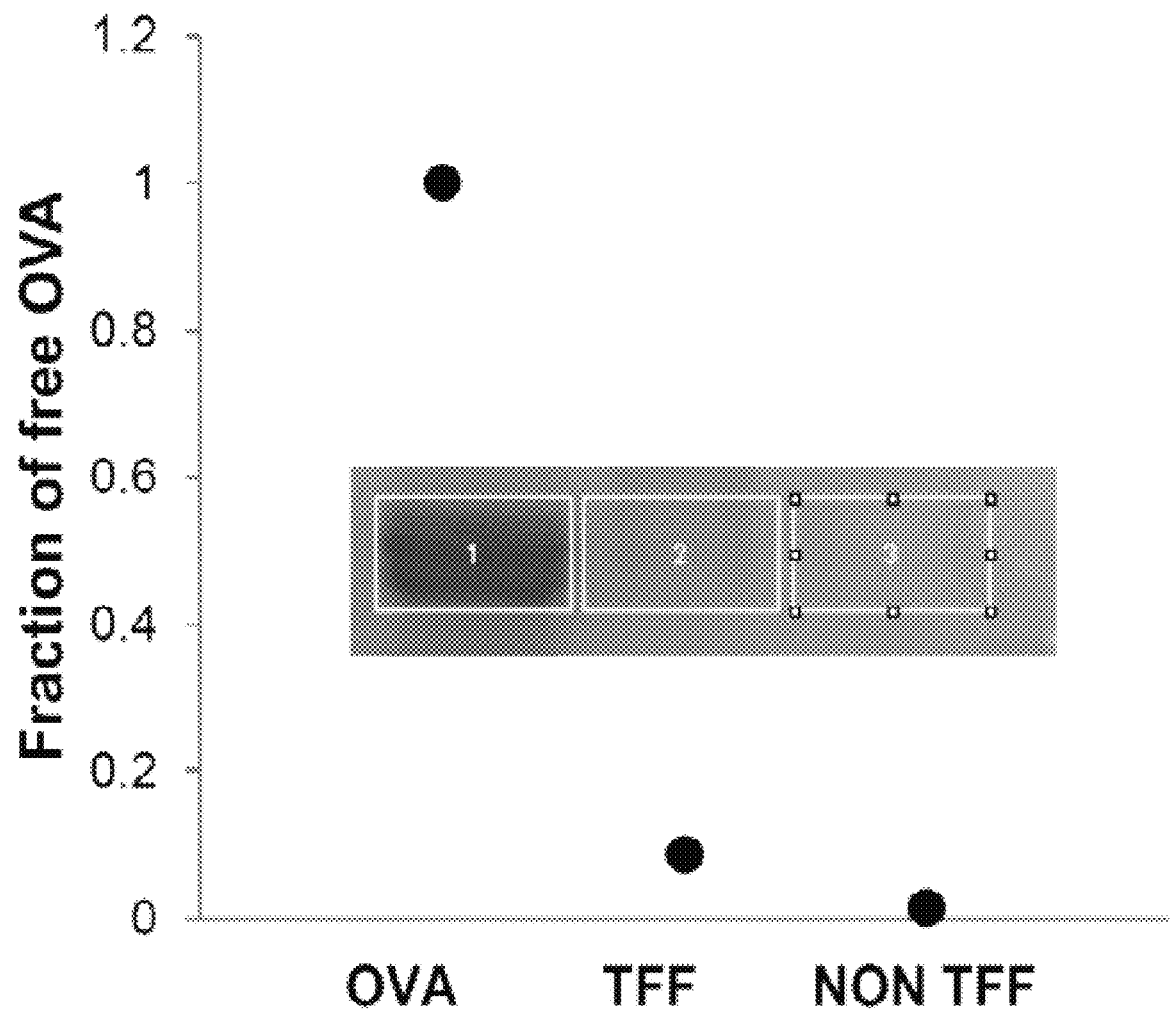
FIG. 2. The fraction of free (unbound) OVA as determined from the intensity of the protein bands on the SDS-PAGE gel.

FIG. 2 shows the fraction of free (unbound) OVA as determined from the intensity of the protein bands on the SDS-PAGE gel. As shown in FIG. 2, the percent of OVA remaining adsorbed to the aluminum hydroxide particles after the lyophilization is estimated to be 92%, indicating only 8% of protein was desorbed from aluminum hydroxide particles after the thin-film freezing and lyophilization. This 92% binding efficiency still meets the United States Food and Drug Administration (FDA) requirement for aluminum-containing vaccines. For example, 75% adsorption is the minimum requirement for diphtheria toxoid and tetanus toxoid antigens.

3. Thermal Analysis of OVA-Adsorbed Aluminum Hydroxide Particles Dried after Thin-Film Freezing.

Thermal analyses of lyophilized OVA-adsorbed aluminum hydroxide powder and its three individual ingredients, OVA protein, aluminum hydroxide and trehalose, were conducted using modulated temperature DSC (Model 2920, TA Instruments, New Castle, Del.). Four to seven mg of each sample was weighed into the aluminum pans and crimped subsequently. An empty aluminum pan was used as a reference. Samples were then heated at a ramp rate of 3° C./min from −30 to 300° C. Data were analyzed using the TA Universal Analysis 2000 software (TA Instruments, New Castle, Del.).

Figure 3:
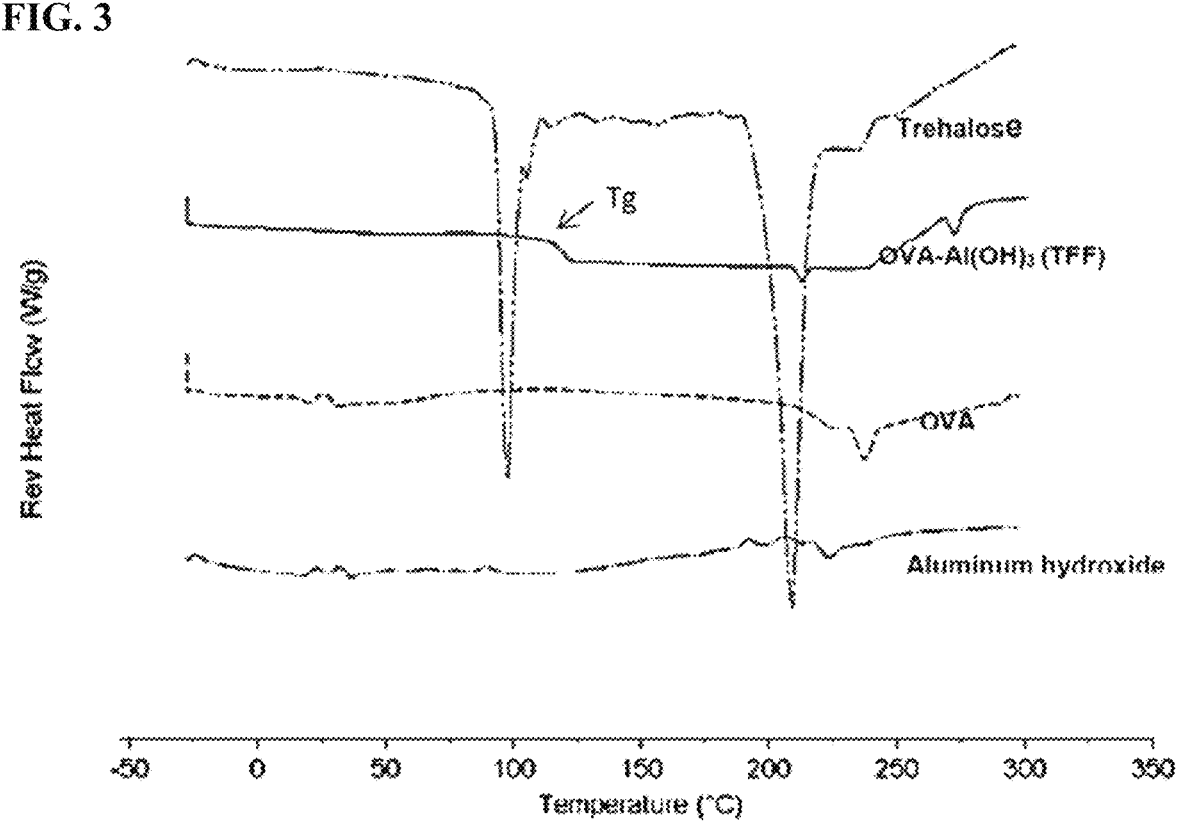
FIG. 3. In the thermogram of the lyophilized OVA-adsorbed aluminum hydroxide powder, a glass transition temperature (Tg) of about 120° C. was observed.

Modulated DSC was carried out to study the thermal properties of lyophilized OVA-adsorbed aluminum hydroxide particles (OVA-Al(OH)$_3$ (TFF)). In the thermogram of the lyophilized OVA-adsorbed aluminum hydroxide powder (FIG. 3), a glass transition temperature (Tg) of about 120° C. was observed.

4. Thin-Film Freeze-Drying of OVA-Adsorbed Aluminum Hydroxide Particles did not Affect the Immunogenicity of the OVA.

Figure 4A:
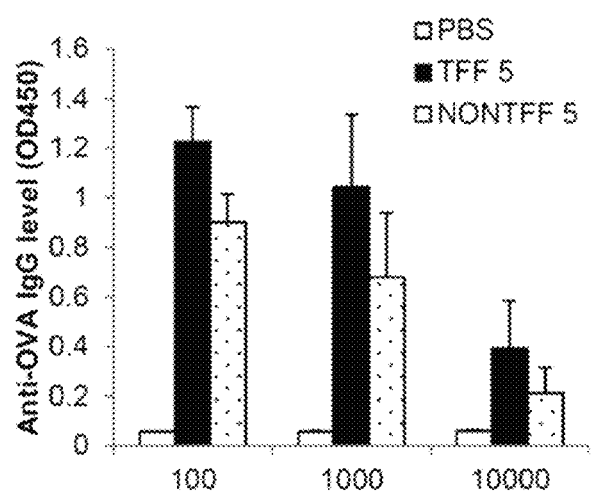
FIG. 4A-C. Anti-OVA IgG levels in mice that were immunized with the lyophilized and reconstituted OVA-adsorbed aluminum hydroxide were not different from that in mice that were immunized the freshly prepared OVA-adsorbed aluminum hydroxide particles; female BALB/c mice (18-20 g, n=5) were subcutaneously injected with OVA-adsorbed aluminum hydroxide particles, before or after lyophilization and reconstitution, on days 0, 14 and 28 with 5 µg (FIG. 4A), 10 µg (FIG. 4B), or 20 µg (FIG. 4C) of OVA per mouse.
Figure 4B:
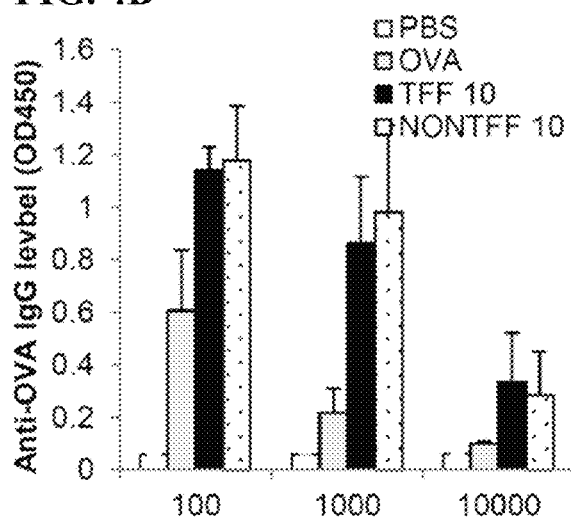
Figure 4C:
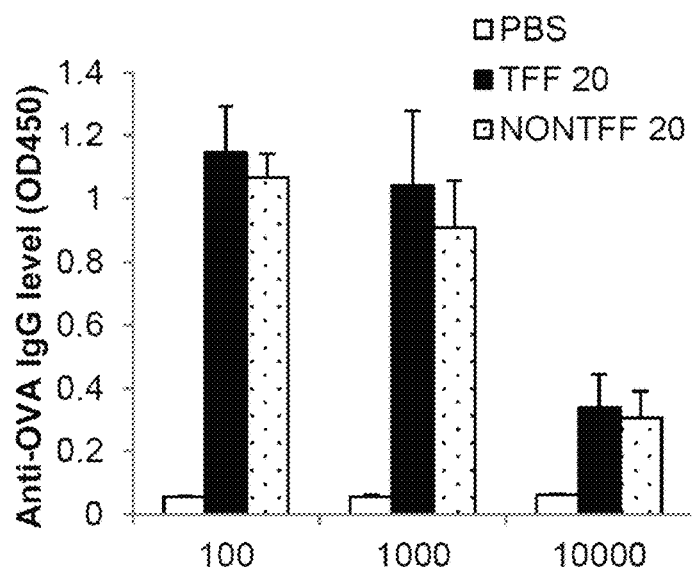

Female BALB/c mice (18-20 g, n=5) were subcutaneously injected with OVA-adsorbed aluminum hydroxide particles, before or after lyophilization and reconstitution, on days 0, 14 and 28 with 5 µg (FIG. 4A), 10 µg (FIG. 4B), or 20 µg (FIG. 4C) of OVA per mouse. The ratio of OVA to aluminum was 1 to 10. Sterile PBS or OVA (10 µg) dissolved in PBS was used as controls. Total anti-OVA IgG level in serum samples was measured 16 days after the third dose using ELISA.

A major limitation of aluminum-containing vaccines is that they cannot be frozen, because freezing of them causes irreversible coagulation that may damage the vaccines and therefore decrease their potency. We hypothesized that using the high speed thin-film freezing method will prevent aggregation during the freeze-drying process, and the resultant lyophilized vaccine powder will retain its potency. Data in FIG. 4A-C clearly show that the anti-OVA IgG levels in mice that were immunized with the lyophilized and reconstituted OVA-adsorbed aluminum hydroxide were not different from that in mice that were immunized the freshly prepared OVA-adsorbed aluminum hydroxide particles.

5. Typical SEM Pictures of the Lyophilized OVA-Adsorbed Aluminum Hydroxide Powder.

The morphology of lyophilized OVA-adsorbed aluminum hydroxide powder was examined using a Zeiss Supra 40 VP Scanning Electron Microscope. One thin layer of lyophilized OVA-aluminum hydroxide powder was deposited on the specimen stub using a double stick carbon tape. The specimen stubs with samples were then placed in the sputter coater chamber and coated with a very thin film of lead (Pb) before SEM examination.

Figure 5:
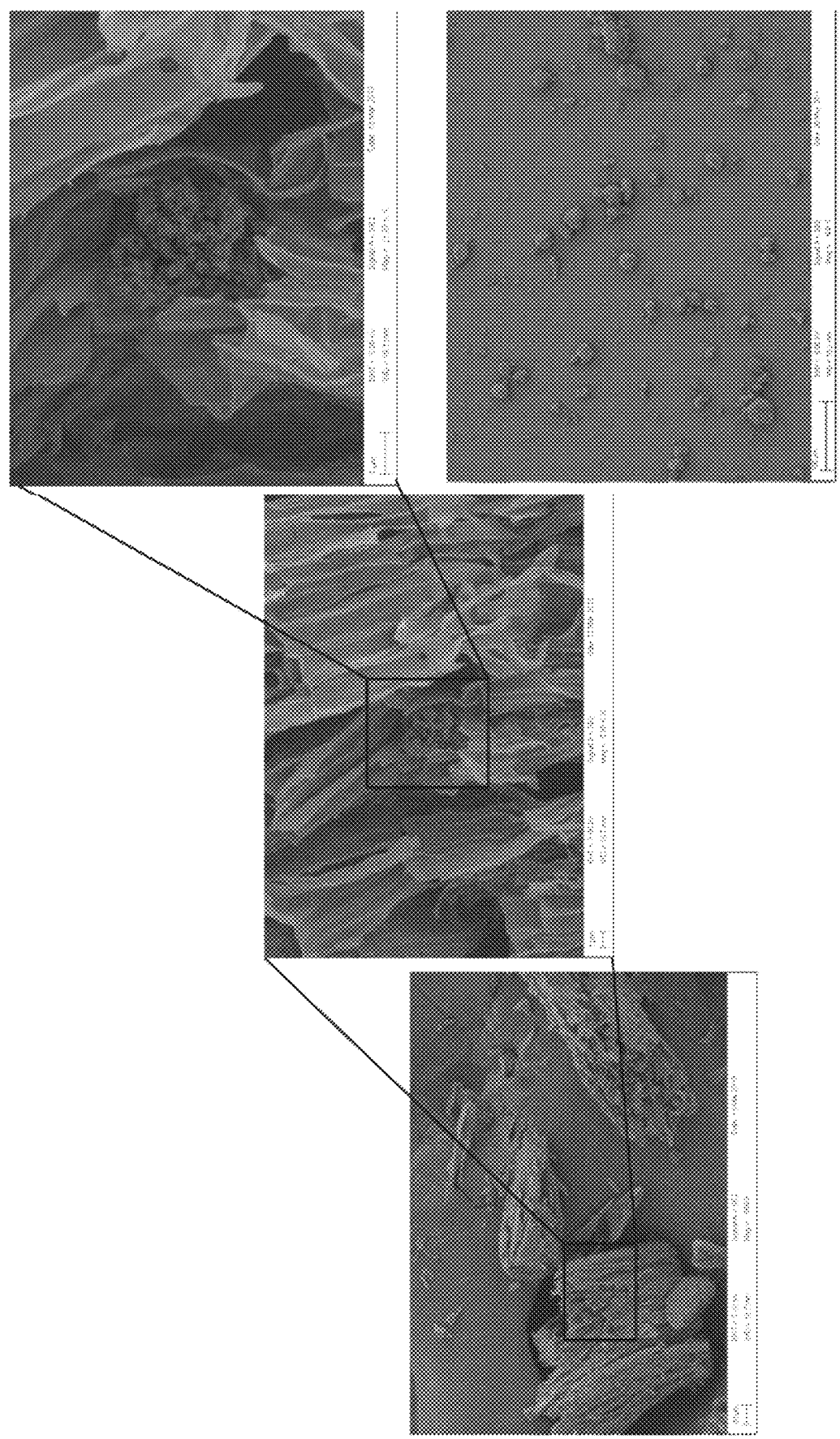
FIG. 5. Lyophilized OVA-adsorbed aluminum hydroxide particles have a rough surface and are in irregular shapes.

As shown in FIG. 5, the lyophilized OVA-adsorbed aluminum hydroxide particles have a rough surface and are in irregular shapes. After lyophilization, trehalose became a leaf-like shape. The OVA-aluminum hydroxide particles are entrapped in the bulk structure of the trehalose, preventing the coagulation of OVA-adsorbed aluminum hydroxide particles. The rough surface, irregular shape particles embedded in the trehalose bulk structure are similar to the morphology of the freshly prepared OVA-adsorbed aluminum hydroxide particles observed using SEM (shown in lower right).

6. Lyophilization of OVA-Adsorbed Aluminum Hydroxide Particles using Thin-Film Freezing with Various Concentrations of Trehalose.

Lyophilization of OVA-adsorbed aluminum hydroxide particles using thin-film freezing were carried out as described in Experiment 1. Trehalose was used as a cryoprotectant during freeze-drying process. Freshly prepared OVA-adsorbed aluminum hydroxide particles were used as a negative control. The particles sizes of physical mixture and TFF powder reconstitutions were determined using a Sympatec Helos laser diffraction instrument (Sympatec GmbH, Germany) equipped with a R3 lens.

Figure 6A:
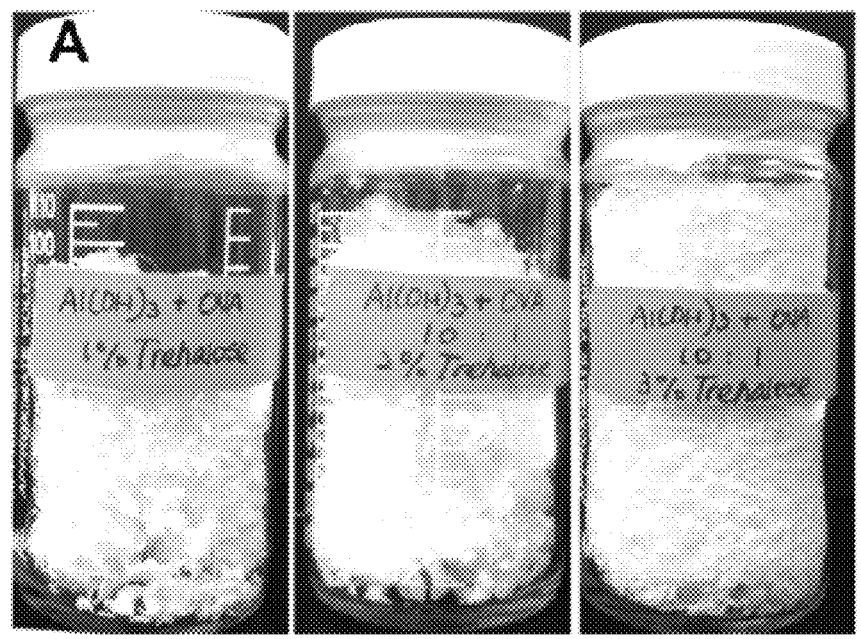
FIG. 6A-B.
Figure 6B:
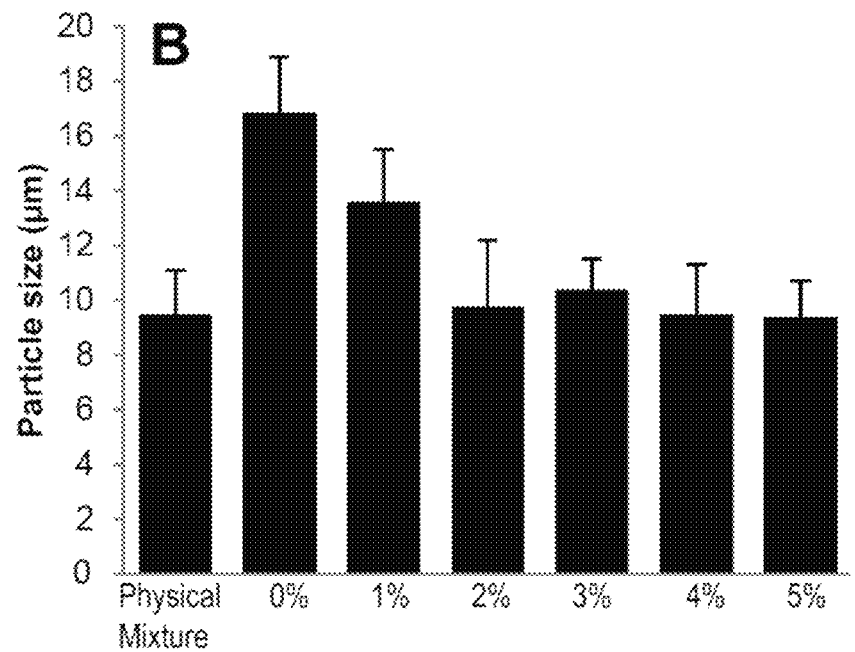

FIG. 6A shows the images of OVA-adsorbed aluminum hydroxide particles lyophilized with different concentrations of trehalose. Shown in FIG. 6B are the sizes of the reconstituted OVA-adsorbed aluminum hydroxide powders lyophilized with various concentrations of trehalose. It appears that when the concentration of the trehalose is increased, the extent of aggregation slightly decreased.

7. The Lyophilization of OVA-Adsorbed Aluminum Phosphate.

Aluminum hydroxide or aluminum phosphate particles in suspension were added into a 50 ml tube, followed by the addition of ovalbumin (OVA) protein solution at a weight ratio of 10:1 ($Al^{3+}$ vs. OVA). Trehalose as a cryoprotectant was also added to a final concentration 2%. The particles were dried after thin-film freezing as mentioned in Experiment 1. The obtained dry powders were stored in a desiccator at room temperature before use. The morphology and size of the lyophilized OVA-adsorbed aluminum hydroxide or OVA-adsorbed aluminum phosphate were examined after reconstitution in water using an Olympus BX60 microscope (Olympus America, Inc., Center Valley, Pa.) and an Sympatec Helos laser diffraction instrument (Sympatec GmbH, Germany) equipped with a R3 lens.

Figure 7A:
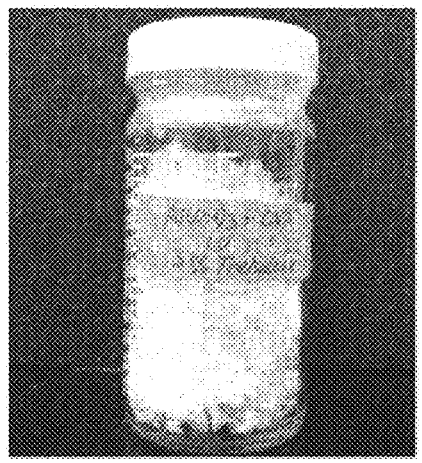
FIG. 7A-D.
Figure 7C:
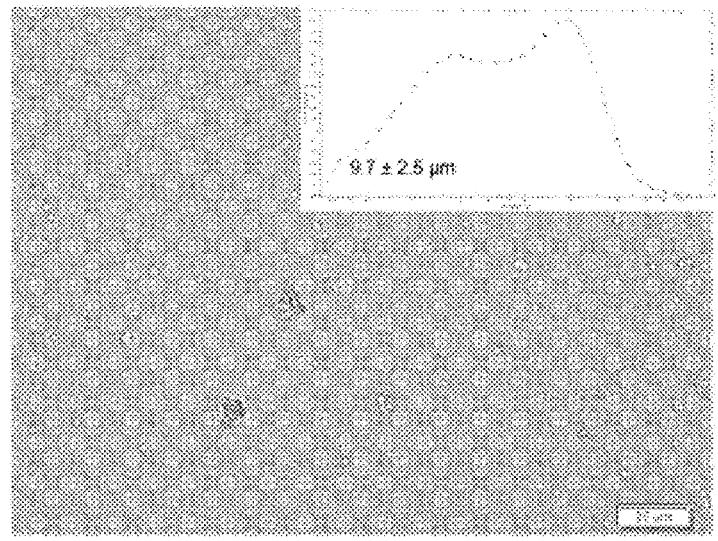
Figure 7B:
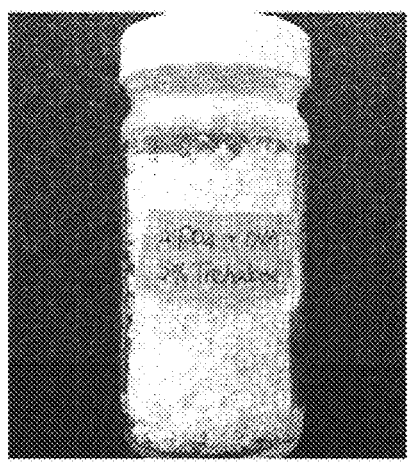
Figure 7D:
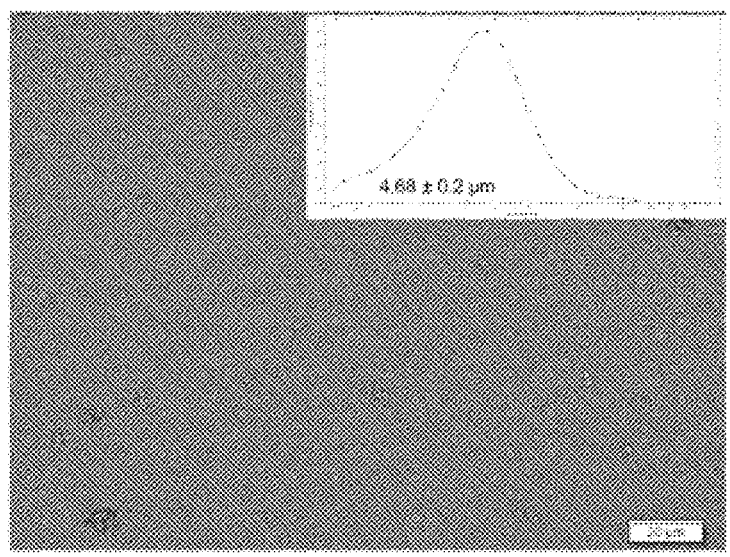
Figure 8A:
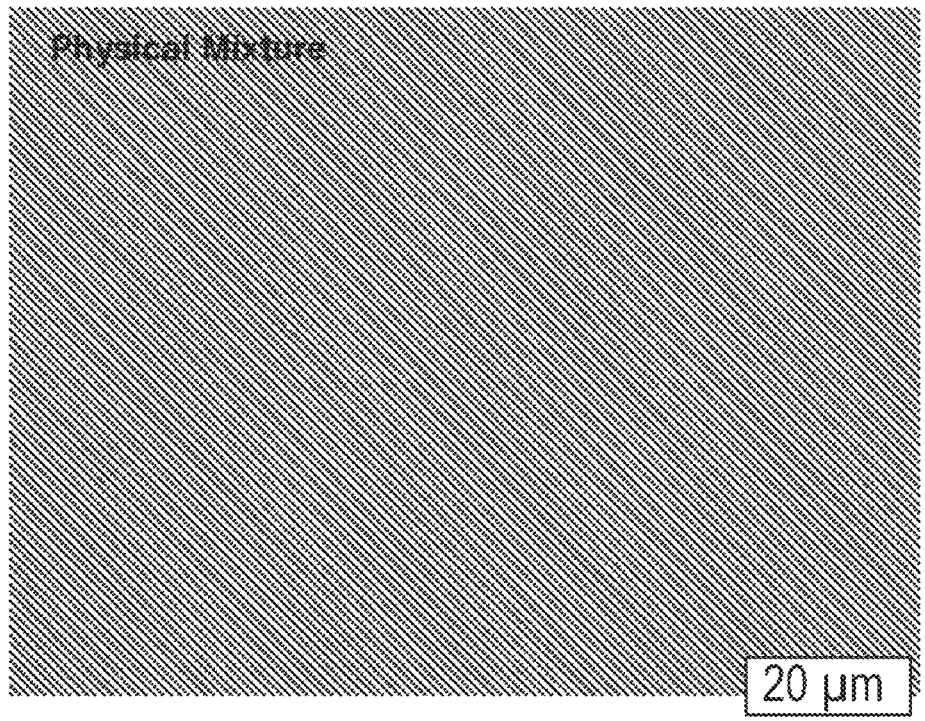
FIG. 8A-B.
Figure 8B:
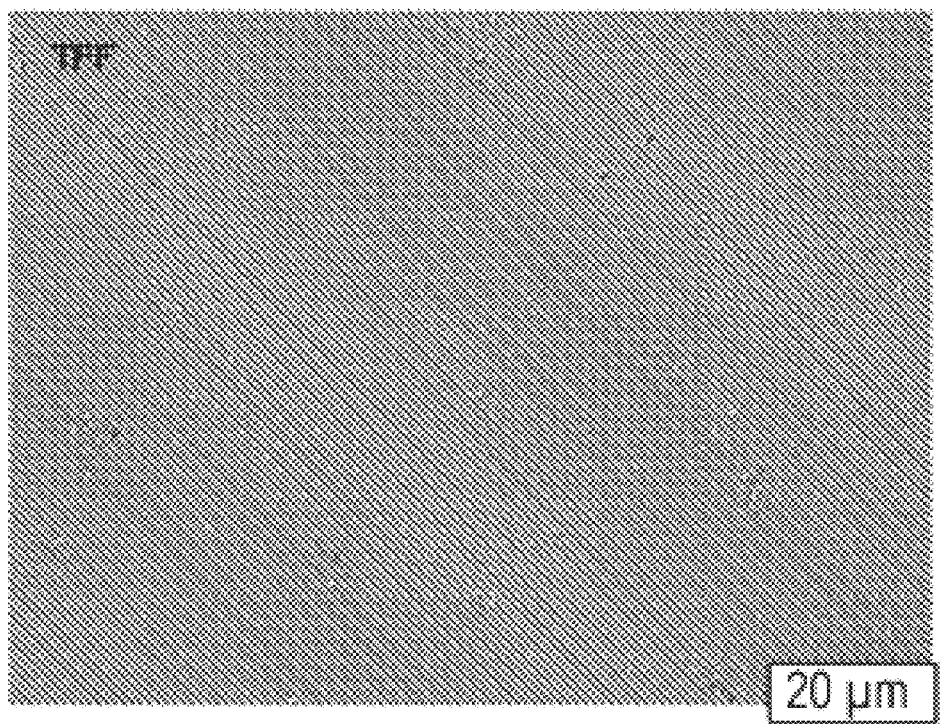

FIGS. 7A and 7B show photos of lyophilized OVA-adsorbed aluminum hydroxide and OVA-adsorbed aluminum phosphate using thin-film freezing, respectively. FIGS. 7C and 7D show microscopic images of lyophilized OVA-adsorbed aluminum hydroxide and OVA-adsorbed aluminum phosphate after reconstitution in water. The OVA-adsorbed aluminum phosphate particles can also be successfully lyophilized using the thin-film freezing method. A light white-colored amorphous lyophilized powder was obtained after drying. The powder can be easily reconstituted in water, normal saline or PBS. Shown in insets in FIG. 7C and FIG. 7D are the particle sizing results from the laser diffraction instrument.

8. The Preparation of a Dry Powder of Ovalbumin Adsorbed on a Commercial Alhydrogel.

In the previous experiments, we prepared the aluminum hydroxide suspension by dispersing the Dried Aluminum Hydroxide Gel (Powder, U.S.P) from Spectrum Chemicals & Laboratory Products in water. To test whether our method of preparing vaccines having aluminum-containing adjuvants in the dry solid form that are suitable for reconstitution is applicable when commercially available aluminum hydroxide wet gel suspension is used, we used the Alhydrogel 2%, a ready-to-use, sterile aluminum hydroxide wet gel (colloidal) suspension from InvivoGen (San Diego, Calif.). Initially, twenty-five milliliters of the Alhydrogel 2% were added into a 50 ml tube, followed by the addition of 25 ml of ovalbumin (OVA) protein solution to a final $Al^{3+}$ to OVA weight ratio of 10:1. Trehalose was also added to a final concentration of 2% (w/v). The particles were processed by thin-film freezing as described herein, and the frozen liquid was removed using a VirTis Advantage bench top tray lyophilizer. The morphology and size of the physical mixture of OVA-adsorbed Alhydrogel with 2% trehalose and the reconstituted dried OVA-adsorbed Alhydrogel with 2% trehalose (in phosphate buffer) were examined using an Olympus BX60 microscope (Olympus America, Inc., Center Valley, Pa.).

FIGS. 8A-B show the microscopic images of the physical mixture of OVA-adsorbed Alhydrogel and the OVA-adsorbed Alhydrogel dry powder after reconstitution, respectively. Clearly, our method can be used to prepare a dry powder of the OVA-adsorbed Alhydrogel.

9. Materials

Dried aluminum hydroxide gel was from Spectrum (Gardena, Calif.). Aluminum chloride hexahydrate, sodium hydroxide, OVA, horse serum, Laemmli sample buffer, fluorescein-5(6)-isothiocyanate (FITC), sodium bicarbonate, sodium carbonate, phosphate-buffered saline (PBS), 5-(and-6-)-carboxylfluorescein diacetate succinimidyl ester (CFSE), and incomplete Freund's adjuvant (IFA) were from Sigma-Aldrich (St. Louis, Mo.). Goat anti-mouse immunoglobulins (IgG) were from Southern Biotechnology Associates, Inc. (Birmingham, Ala.). Carbon-coated 400-mesh grids were from Electron Microscopy Sciences (Hatfield, Pa.). Vectashield mounting medium with 4', 6-diamidino-2-phenylindole (DAPI) was from Vector Laboratories, Inc. (Burlingame, Calif.). *Bacillus anthracis* rPA protein was from List Biological Laboratories, Inc. (Campbell, Calif.). Bio-safe™ Coomassie blue staining solution and Bio-Rad DC™ protein assay reagents were from Bio-Rad Laboratories (Hercules, Calif.). GM-CSF was from R&D Systems, Inc. (Minneapolis, Minn.). Tissue-Tek® O.C.T. compound medium was from Sakura Finetek USA, Inc. (Torrance, Calif.). Cell culture medium and fetal bovine serum (FBS) were from Invitrogen (Carlsbad, Calif.). Alhydrogel® (2%, w/v) was from InvivoGen (San Diego, Calif.). Tetanus antitoxin concentrated/purified (TT vaccine) was from Colorado Serum Company. The TT vaccine contains aluminum potassium sulfate. Mouse Anti-Tetanus Toxoid Ig's ELISA kit was from Alpha Diagnostic International (San Antonio, Tex.). Human hepatitis B vaccine Engerix-B from GlaxoSmithKline was purchased from the University of Texas at Austin University Health Services. Engerix-B contains aluminum hydroxide.

10. Mice and cell lines

Female BALB/c and C57BL/6 mice, 6-8 weeks of age, were from Charles River Laboratories, Inc. (Wilmington, Mass.). The OVA-expressing B16-OVA cell line was generously provided by Dr. Edith M. Lord and Dr. John Frelinger (University of Rochester Medical Center, Rochester, N.Y.) and cultured in RPMI1640 medium supplemented with 5% FBS and 400 μg/ml of G418 (Sigma). Mouse J774A.1 macrophage cells (#TIB-67TM) were from the American Type and Culture Collection (Manassas, Va.) and grown in DMEM medium supplemented with 10% FBS, 100 U/ml of penicillin and 100 µg/ml of streptomycin, all from Invitrogen (Carlsbad, Calif.). DC2.4 cells (a mouse dendritic cell line) (University of Massachusetts Medical School, Worcester, Mass.) grown in RPMI1640 medium supplemented with 10% FBS, 100 U/ml of penicillin and 100 µg/ml of streptomycin.

11. Preparation of Aluminum Hydroxide Nanoparticles and Microparticles

Aluminum hydroxide nanoparticles of less than 200 nm were synthesized by reacting aluminum chloride with sodium hydroxide in a solution. An equal volume of a 3.6 mg/ml $AlCl_3 \cdot 6H_2O$ solution and a 0.04 M NaOH solution were added into a glass vial, and a small volume of 0.01 M NaOH was added to adjust the pH to 7.0. After 20 min of stirring at room temperature, the particle suspension was sonicated for 15 min to break down the particle size. A PD 10 desalting column (Amersham Biosciences, Piscataway, N.J.) was then used to remove the sodium chloride in the suspension, and the eluted fractions were analyzed for nanoparticles by measuring the particle size using a Malvern Zetasizer Nano ZS (Westborough, Mass.), and for aluminum content using a Varian 710-ES ICP Optical Emission Spectrometer (OES) in the Civil Architectural and Environmental Engineering Department at the University of Texas at Austin. The fourth fraction with the highest concentration of aluminum was used for further studies. The endotoxin level in the nanoparticle preparation was not detectable with a ToxinSensor™ chromogenic limulus amebocyte lysate endotoxin assay kit from GenScript (Piscataway, N.J.). Aluminum hydroxide microparticles were prepared by dispersing dried aluminum hydroxide gel into sterile water, followed by vigorous vortexing and 5 min of water bath sonication, if needed. The sizes of the microparticles were determined using a Sympatec Helos laser diffraction instrument (Sympatec GmbH, Germany) equipped with a R3 lens.

12. Adsorption of Protein Antigens on Aluminum Hydroxide Particles

The adsorption of proteins (OVA or PA) on aluminum hydroxide particles of different sizes was carried out by mixing particles in suspension with proteins in solution. Briefly, a certain volume of the protein solution was added into a tube (10 µg OVA or 4 µg PA), followed by the addition of particles in suspension at a weight ratio of 1:2 to 1:1 (OVA vs. particles) or 1:5 (PA vs. particles). After 20 min of gentle stirring, the protein-particle mixtures were stored at 4° C. before use and, if needed, freeze-dried before further use.

SDS-PAGE was used to determine the binding efficiency of the OVA to aluminum hydroxide before and after TFFD. The OVA-adsorbed aluminum hydroxide dry powder (OVA to $Al^{3+}$ ratio (w/w), 1 to 10) was reconstituted in a phosphate buffer and applied on SDS-PAGE gel. As a control, OVA alone and freshly prepared OVA-adsorbed aluminum hydroxide suspension (with 2% trehalose, w/v) were also included. Samples were mixed with a Laemmli sample buffer (62.5 mM Tris-HCl, pH 6.8, 25% glycerol, 2% SDS, and 0.01% Bromophenol Blue) before applied to 7.5% Mini-PROTEAN® TGX™ precast polyacrylamide gels (Bio-Rad). Precision plus protein standards were also run along with the samples at 130 V for 1 h. The gel was then stained in a Bio-Safe™ Coomassie blue staining solution and scanned using a Kodak Image Station 440CF (Rochester, N.Y.). The intensity of the protein bands in the gel was quantified using the NIH ImageJ software, and the binding efficiency was calculated by subtracting the percentage of unbound protein (band intensity from vaccine dry powder or freshly prepared vaccine suspension) from the total protein (band intensity of OVA alone).

13. Thin-Film Freeze Drying (TFFD)

Three types of aluminum-containing compounds, dried aluminum hydroxide gel (USP grade), 2% Alhydrogel®, and aluminum phosphate, were used to adsorb OVA as a model antigen. The OVA-adsorbed aluminum hydroxide vaccine was prepared by mixing an OVA solution with an aluminum hydroxide suspension in PBS (pH 7.4, 10 mM) to reach an OVA to $Al^{3+}$ weight ratio of 1:10. The vaccine contained 31.4 µg/ml of OVA, 0.09% of aluminum hydroxide, and 0-5% (w/v) of trehalose. The OVA-adsorbed aluminum phosphate vaccine (31.4 µg/ml of OVA, 0.142% (w/v) of aluminum phosphate, and 2% (w/v) of trehalose) was prepared similarly. When the 2% Alhydrogel® was used, Alhydrogel® (25 ml) was added into a 50 ml tube, followed by the addition of 25 ml of an OVA solution (1 mg/ml) at an OVA to $Al^{3+}$ weight ratio of 1:10, and 1 g of trehalose to obtain a final formulation with 2% (w/v) of trehalose, ~1% (w/v) of Alhydrogel®, and 0.5 mg/ml of OVA. The samples were subjected to TFF and lyophilized as described previously [J. D. Engstrom et al., *Pharmaceutical Research*, 25 (2008) 1334-1346; M. Zhang et al., *European journal of pharmaceutics and biopharmaceutics*, 82 (2012) 534-544]. Briefly, the aluminum-containing vaccine suspensions/dispersions were dropped onto a pre-cooled rotating cryogenic steel surface to formed thin films. The thin films were removed by a steel blade. In order to avoid the overlap of two droplets, the speed at which the vaccine suspension was dropped on the cryogenic substance was controlled at 7 rpm. The frozen film-like solids were collected in liquid nitrogen and dried using a VirTis Advantage bench top tray lyophilizer (The VirTis Company, Inc. Gardiner, N.Y.). Lyophilization was performed over 72 h at pressures less than 200 mTorr, while the shelf temperature was gradually ramped from −40° C. to 26° C. After lyophilization, the solid vaccine powder was quickly transferred to a sealed container and stored in a desiccator at room temperature before further use [A. B. Watts et al., *Pharmaceutical research*, 30 (2013) 813-825]. To preliminarily evaluate the stability of the TFFD powder, the vaccine powder (OVA adjuvanted with Alhydrogel®) was reconstituted after 10-month of storage (at room temperature) and examined under a microscope (Olympus BX60 microscope, Olympus America, Inc., Center Valley, Pa.).

To dry the TT vaccine, trehalose was added directly into the TT vaccine, or after the TT vaccine was diluted 50-fold in a phosphate buffered saline (PBS, pH 6.3, 10 mM) to adjust the final concentration of trehalose to 2% (w/v). The vaccine was then subjected to TFFD as mentioned above. To dry Engerix-B, trehalose was added directly into the vaccine to obtain a formulation with 2% (w/v) of trehalose, ~20 mg/ml of HBsAg, and 0.144% (w/v) of aluminum hydroxide, and the vaccine was then subjected to TFFD.

The morphology of the vaccines in suspension was examined under an Olympus BX60 microscope. The sizes of particles in all samples were determined using a Sympatec Helos laser diffraction instrument (Sympatec GmbH, Germany) equipped with a R3 lens.

14. Shelf Freeze-Drying

An OVA-adsorbed aluminum hydroxide vaccine that contained 2% of trehalose (w/v), 0.09% of aluminum hydroxide, and 31.4 µg/ml of OVA in PBS (pH 7.4, 10 mM) was frozen on the shelf of a −20° C. or −80° C. freezer overnight and then lyophilized using a VirTis Advantage bench top tray lyophilizer as mentioned above. The dry powder was stored in a desiccator at room temperature before use.

15. The Effect of the Concentration of Trehalose in Vaccine on Thin-Film Freeze Drying In order to investigate the effect of the concentration of trehalose on TFFD of vaccines, various amounts of trehalose were added into the OVA-adsorbed aluminum hydroxide in suspension (1:10, OVA vs. $Al^{3+}$, w/w) to prepare vaccine formulations that contained 0%, 1%, 2%, 3%, 4%, and 5% of trehalose (w/v). The suspensions were then subjected to TFFD as mentioned above.

16. Residual Moisture Content

Aliquots of methanol are dispensed through the septum of scintillation vials to form a suspension concentration of 10-100 mg/mL. Vials are then placed in a bath sonicator (Mettler Electronics) for 5 minutes at maximum power to insure complete suspension of the dry vaccine. Moisture content is measured for a 200 µL aliquot with an Aquatest 8 Karl-Fischer Titrator (Photovolt Instruments). The moisture values are corrected with a 200 µL methanol blank control.

17. Transmission Electron Microscopy (TEM)

The morphology and size of the OVA-adsorbed aluminum hydroxide nanoparticles were examined using an FEI Tecnai Transmission Electron Microscope in the Institute for Cellular and Molecular Biology (ICMB) Microscopy and Imaging Facility at The University of Texas at Austin. Carbon-coated 400-mesh grids were activated for 1-2 min. One drop of the OVA-nanoparticle suspension was deposited on the grids and incubated for 2 min at room temperature. The grids were washed with water and dried for 1 min. Extra water was removed using filter paper. The grids were then stained with uranyl acetate for 2 min, washed with water, and allowed to dry for 15 min before observation.

18. Scanning Electron Microscope (SEM)

The size and morphology of OVA-adsorbed aluminum hydroxide nanoparticles and microparticles were also examined using a Zeiss Supra 40 VP Scanning Electron Microscope in the ICMB Microscopy and Imaging facility. One drop of aluminum hydroxide particle suspension was deposited on the specimen stub using a double stick carbon tape and allowed to dry overnight. The specimen stubs with samples were then placed in the sputter coater chamber and coated with a very thin film of iridium before SEM examination.

The morphology of the OVA-adsorbed aluminum hydroxide dry powder and freshly prepared OVA-adsorbed aluminum hydroxide suspension was examined using a Zeiss Supra 40 VP scanning electron microscope in the ICMB Microscopy and Imaging Facility at The University of Texas at Austin [W. T. Leach et al., *Journal of pharmaceutical sciences*, 94 (2005) 56-69]. When preparing the TFFD samples for SEM, one thin layer of the dried powder was deposited on the specimen stub using a double stick carbon tape. For the freshly prepared OVA-adsorbed aluminum hydroxide suspension, the suspension was placed on the specimen stub and allowed to dry overnight. The specimen stubs with samples were then placed in the sputter coater chamber and coated with a very thin film of lead (Pb) before examination.

19. Differential Scanning Calorimetry (DSC)

Thermal analysis of the OVA-adsorbed aluminum hydroxide dry powder and its individual components, OVA, aluminum hydroxide, and trehalose, were conducted using a modulated temperature DSC (Model 2920, TA Instruments, New Castle, Del.) [M. Zhang et al., *European journal of pharmaceutics and biopharmaceutics*, 82 (2012) 534-544]. Four to seven milligrams of each sample was weighed into the aluminum pans (PerkinElmer Instruments, Norwalk, Conn.), which were crimped subsequently. An empty aluminum pan was used as a reference. Samples were then heated at a ramp rate of 3° C./min from −30° C. to 300° C. Data were analyzed using the TA Universal Analysis 2000 software (TA Instruments, New Castle, Del.).

20. X-Ray Diffraction

The X-ray diffractograms of aluminum hydroxide particles were obtained with a Scintag X1 theta-theta powder diffractometer using Cu K-alpha radiation and a solid state Si(Li) detector in the Texas Materials Institute X-Ray Facility in the Chemical Engineering Department at the University of Texas at Austin.

21. Stability of Aluminum Hydroxide Particles

The stability of aluminum hydroxide particles in suspension was initially examined before adsorption with proteins. The particles in suspension were kept at 4° C. for 30 days and the sizes were measured on days 0 and 30. A short-term stability of the OVA-adsorbed aluminum hydroxide particles was then carried out. After the adsorption of OVA, the aluminum hydroxide particles of different sizes were kept at 4° C. for 48 h, and their sizes were measured every 24 h. To evaluate whether the OVA-adsorbed aluminum hydroxide nanoparticles can be lyophilized, the nanoparticles adsorbed with OVA, or nanoparticles adsorbed with OVA but suspended in 2% (w/v) of trehalose, were lyophilized using a FreeZone plus 4.5 liter cascade console freeze dry system (Labconco corporation, Kansas city, Mo.). The lyophilized powder was reconstituted with de-ionized and filtered (0.2 µm) water. In order to evaluate the stability of the lyophilized particles, the lyophilized powder was stored at 4° C. and reconstituted in de-ionized and filtered water on days 0, 14 and 28 to measure the particle size.

22. Repeated Freeze-Thawing of Thin-Film Freeze Dried Vaccine Powder

The dried powder of TT vaccine was subjected to three cycles of freezing (−20° C. for 8 h) and thawing (4° C. for 16 h), reconstituted, and examined under a microscope to detect aggregation. As a control, fresh TT vaccine was also subjected to the same three cycles of freezing and thawing and examined under a microscope.

23. SDS-PAGE

SDS-PAGE assay was used to determine the extent to which the protein antigen was bound onto the aluminum hydroxide particles. Briefly, OVA (10 µg) was mixed with various amount of aluminum hydroxide particles in suspension (0, 1, 2, 5, 10, 20, 50, and 100 µg). The OVA-particle mixtures were then lyophilized. The resultant powders were reconstituted in de-ionized water and mixed with Laemmli sample buffer (62.5 mM Tris-HCl, pH 6.8, 25% glycerol, 2% SDS, and 0.01% Bromophenol Blue). Electrophoresis was performed with 7.5% Mini-PROTEAN® TGX™ precast polyacrylamide gels (Bio-Rad). Precision plus protein standards were also run along with the samples at 130 V for 1 h. The gels were then stained in a Bio-Safe Coomassie blue staining solution and scanned using a Kodak Image Station 440CF (Rochester, N.Y.).

24. Preparation of Bone Marrow Dendritic Cells

Bone marrow dendritic cells (BMDCs) were generated from bone marrow precursors from C57BL/6 mice. Briefly, femur bones were removed from C57BL/6 mice and purified from surrounding tissues. The bones were left in 70% ethanol for 2 min for disinfection and washed with sterile PBS. After both ends of femur bones were removed, bone marrow was flushed out with PBS using a hypodermic needle attached to syringe. After 3 washes with PBS, all leukocytes obtained were transferred into a bacteriological petri dishes and cultured with 10 ml of RPMI1640 medium supplemented with 10% FBS, 100 U/ml of penicillin, 100 μg/ml of streptomycin, 2-mercaptomethanol (50 μM) and granulocyte-macrophage-colony stimulating factor (GM-CSF) (100 ng/ml). Cells were allowed to grow at 37° C. under 5% $CO_2$ for 3 days, and another 10 ml of culture medium was added into the original dish. On day 6, half of the supernatant was collected and centrifuged at 800 rpm for 4 min. Cell pellet was re-suspended in culture medium and added back into the original dish. Cells on days 7 or 8 were used for further studies. In order to examine the purity, the cells were stained with antibodies against CD11c (BD Pharmingen, San Diego, Calif.) [22], and analyzed using a Guava EasyCyte 8HT microcapillary flow cytometer (Millipore Corporation, Hayward, Calif.). A high purity of 86.5% bone marrow dendritic cells was obtained after 8 days in culture medium.

25. Uptake of the OVA-Adsorbed Particles by BMDCs, DC2.4 Cells and J77A4.1 Cells in Culture In vitro uptake studies were carried out using OVA that was pre-labeled with FITC. BMDCs, DC2.4 or J77A4.1 cells (50,000 cells/well) were seeded into 24-well plates and allowed to grow overnight at 37° C., 5% $CO_2$. FITC-labeled OVA-particles were added into the cell culture and incubated at 37° C. under 5% $CO_2$ or at 4° C. After 3 or 6 h of incubation, cells were washed with PBS (10 mM, pH 7.4) three times, lyzed with Triton X-100 (0.17%, v/v) and then applied to a BioTek Synergy HT microplate reader to measure the fluorescence intensity. Endocytosis is inhibited at 4° C. Therefore, a subtraction of the fluorescence intensity of the cells incubated at 4° C. from the fluorescence intensity of the cells incubated at 37° C., 5% $CO_2$, allows us to estimate the amount of FITC-OVA that was internalized.

26. Fluorescence Microscopy

DC2.4 cells (1.5×104) were plated on poly-D-lysine-coated glass coverslips overnight. FITC-labeled OVA-adsorbed particles were added and incubated with the cells for 30 to 60 min at 37° C., 5% $CO_2$. Cells were then washed with PBS, fixed in 3% paraformaldehyde for 20 min at room temperature, followed by three times of wash with PBS. Coverslips were mounted on the slides using Vectashield mounting medium with DAPI. Fluorescent images were acquired using an Olympus BX60 Biological Microscope (Center Valley, Pa.).

The TT vaccine was used in this study. The vaccine was dried using TFFD and reconstituted in a phosphate buffer before examination. Freshly diluted TT vaccine (in a phosphate buffer) was used as a negative control. The final trehalose concentration in both the samples was 2% (w/v). Fluorescence emission spectrum was recorded using a PTI Quanmaster spectrofluorimeter (Photon Technology International, Santa Clara, Calif.). An excitation wavelength of 290 nm was employed, and the emission spectrum was collected from 280 nm to 530 nm [G. Jiang et al., Journal of pharmaceutical sciences, 95 (2006) 80-96].

27. Animal Studies

All animal studies were carried out following National Institutes of Health guidelines for animal care and use. The animal protocol was approved by the Institutional Animal Care and Use Committee at The University of Texas at Austin. When OVA was used as the antigen, female BALB/c mice (18-20 g) were immunized with OVA-adsorbed aluminum hydroxide particles once a week for three consecutive weeks by subcutaneous injection. The dose of the OVA was 10 μg per mouse per injection; 20 μg per mouse per injection for the particles. Sterile PBS or OVA (10 μg) dissolved in PBS was used as controls. Twenty seven days after the first dose, mice were bled for antibody assay.

When the PA was used as the antigen, female BALB/c mice (18-20 g) were immunized subcutaneously with PA-adsorbed aluminum hydroxide particles on days 0 and 14. As negative controls, mice were injected with sterile PBS or PA alone. The dose of PA was 4 μg per mouse per injection, and the dose of the particles was 20 μg per mouse per injection. Mice were bled 1 week and 1 month after the second immunization for antibody assay.

All animal studies were carried out following the National Research Council guide for the care and use of laboratory animals. The animal protocol was approved by the Institutional Animal Care and Use Committee at The University of Texas at Austin. Female BALB/c mice, 6-8 weeks of age, were from Charles River Laboratories, Inc. (Wilmington, Mass.). Mice (n=5) were subcutaneously (s.c.) injected with OVA-adsorbed aluminum hydroxide or the TT vaccine, freshly prepared or reconstituted from TFFD powder. For the OVA-adsorbed aluminum hydroxide, mice were immunized on days 0, 14 and 28 with 5 μg, 10 μg, or 20 μg of OVA per mouse. As controls, mice were injected with sterile PBS or OVA alone (10 μg) dissolved in PBS. For the TT vaccine, mice were immunized on days 0, 14, and 28, and the dose of TT was 3.75 Lf (flocculation units) of tetanus toxoid per mouse per injection. Sterile PBS and TT vaccine freshly diluted with 2% trehalose were used as controls. Sixteen days after the third dose, mice were bled for antibody assay. Total anti-OVA IgG or anti-TT IgG levels in serum samples were measured using ELISA.

28. Enzyme-Linked Immunosorbent Assay (ELISA)

ELISA was completed as previously described [B. R. Sloat et al., Journal of controlled release, 141 (2010) 93-100]. EIA/RIA flat bottom, medium-binding, polystyrene 96-well plates (Corning Costar, Corning, N.Y.) were coated with 100 ng of OVA in 0.1 ml of carbonate buffer (0.1 M, pH 9.6) overnight at 4° C. After washed with PBS/Tween 20 (10 mM, pH 7.4, 0.05% Tween 20), the plates were blocked with 5% (v/v) horse serum in PBS/Tween 20 (for mice immunized with OVA as an antigen) for 1 h at 37° C. Serum samples were diluted in 5% horse serum/PBS/Tween 20 (or 4% BSA/PBS/Tween 20) and added to the plates after the removal of the blocking solution. The plates were incubated for an additional 2 h at 37° C. The samples were removed, and the plates were washed with PBS/Tween 20 five times. Horseradish peroxidase-labeled goat-anti-mouse immunoglobulins (IgG, 5000-fold dilution) were added as the secondary antibody into the plates, followed by 1 h of incubation at 37° C. The plates were washed five times with PBS/Tween 20 again. After 30 min incubation with a 3,3', 5,5'-Tetramethylbenzidine (TMB) solution at room temperature, the reaction was stopped with sulfuric acid (0.2 M), and the absorbance was read at 450 nm using a BioTek Synergy HT microplate reader (Winooski, Vt.). Anti-TT IgG levels were determined using a mouse Anti-Tetanus Toxoid Ig's ELISA Kit following the manufacturer's instructions.

29. Tumor Prevention Assays

Female C57BL/6 mice (18-20 g) were immunized with OVA-adsorbed particles, PBS, or OVA alone on days 0, 7, and 14 by subcutaneous injection. The dose of OVA was 10 μg per mouse per injection, and the particles were 20 μg. On day 21, B16-OVA cells (50,000/mouse) were subcutaneously injected in the right flank of the mice. Tumor growth was monitored daily, and tumor size was measured using a caliper and calculated using the following equation: tumor diameter=(L+W)/2.

30. Histological Examination

BALB/c mice were immunized with PA adsorbed aluminum hydroxide particles on day 0 and 19. As negative controls, mice were injected with sterile PBS or PA alone. On day 40, mice were euthanized for histological examination. The hair on the injection site was initially removed using Nair® lotion (Church and Dwight Co, Princeton, N.J.). The skin at the injection sites, including skin and muscle tissues, were removed and spread out on a piece of index paper. The tissue and paper together were cut into a 1 cm×1 cm square and transferred to tissue cryomolds (25 mm×20 mm×5 mm, Sakura Finetek USA, Inc. Torrance, Calif.). Any residual spaces in the cryomolds were filled with Tissue-Tek® O.C.T. compound medium and fixed in the vapor of liquid nitrogen for 10 min. After the O.C.T. compound medium was frozen into a solid white color, the whole cryomoles were removed and wrapped with aluminum foil. The prepared samples were stored at −80° C. for cryostate sectioning and staining with Hematoxylin and eosin (H&E, Sigma, St. Louis, Mo.) in the Histology and Tissue Analysis Core in the Dell Pediatric Research Institute, University of Texas at Austin.

31. Statistics

Statistical analyses were conducted using analysis of variance followed by Fischer's protected least significant difference procedure. A p-value of ≤0.05 (two-tail) was considered statistically significant.

32. Studies of the Effect of Aluminum Adjuvant Particle Size on Efficacy of Vaccines.

Synthesis and Characterization of Aluminum Hydroxide Particles

Figure 10A:
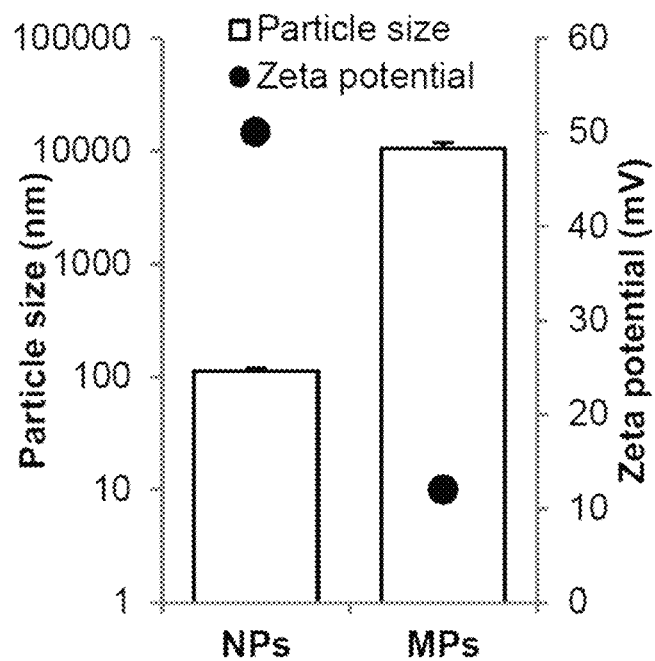
FIG. 10A-D.
Figure 10B:
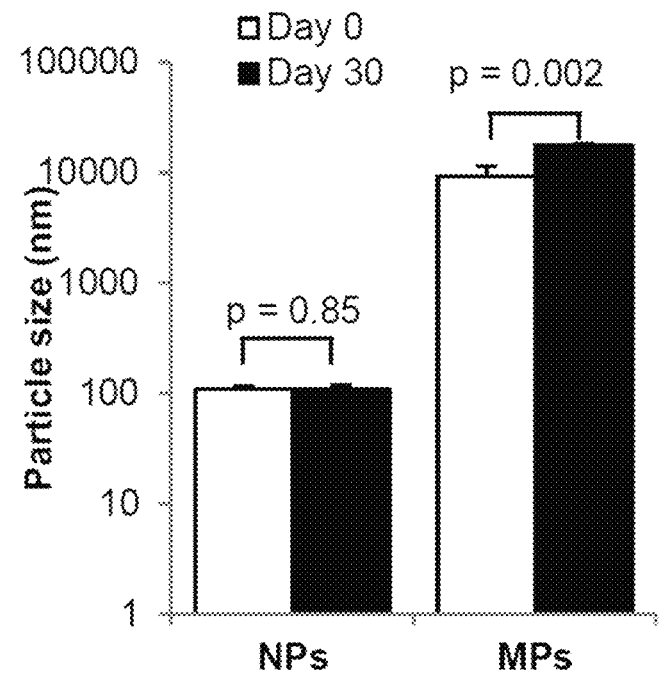
Figure 10C:
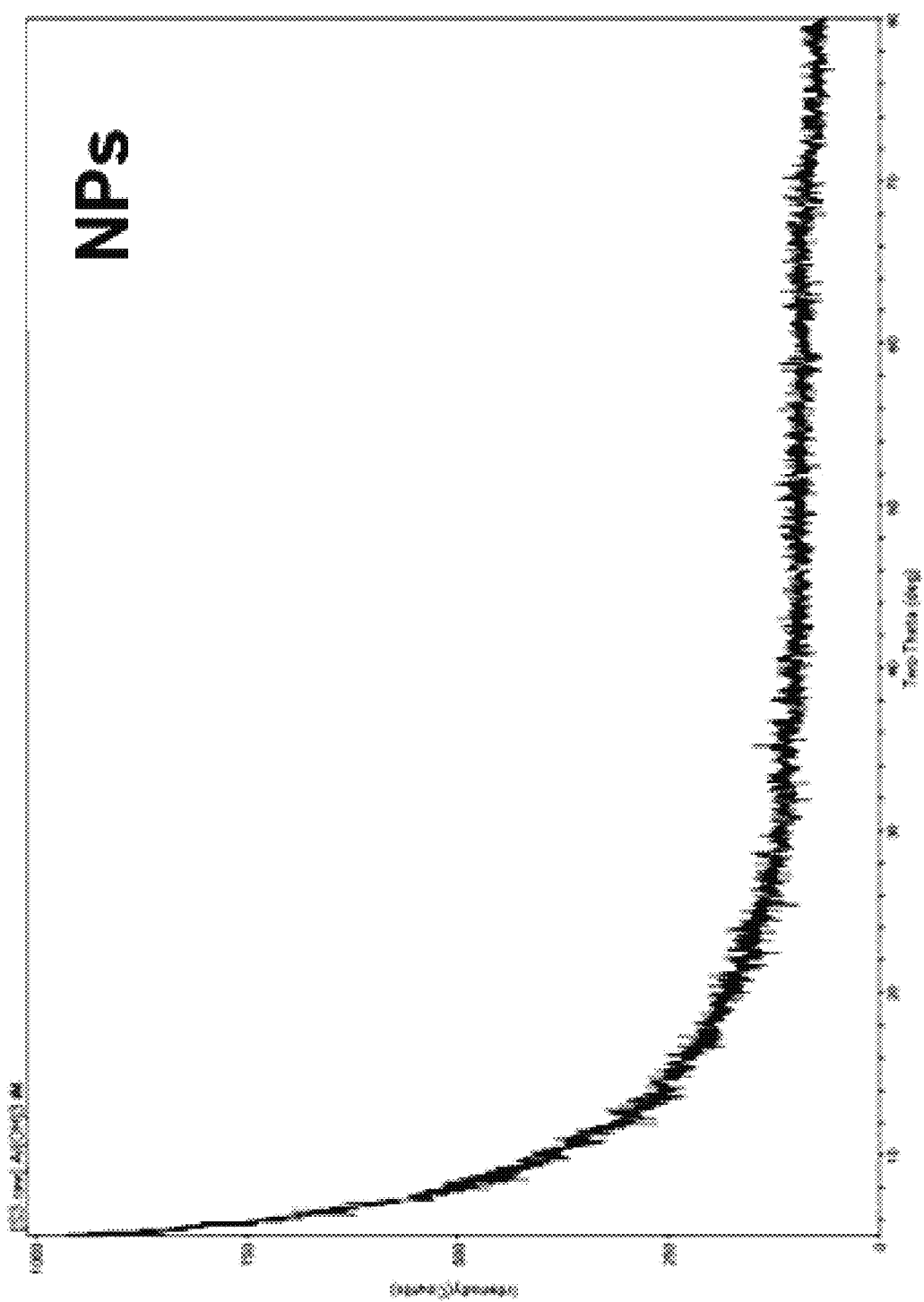
Figure 10D:
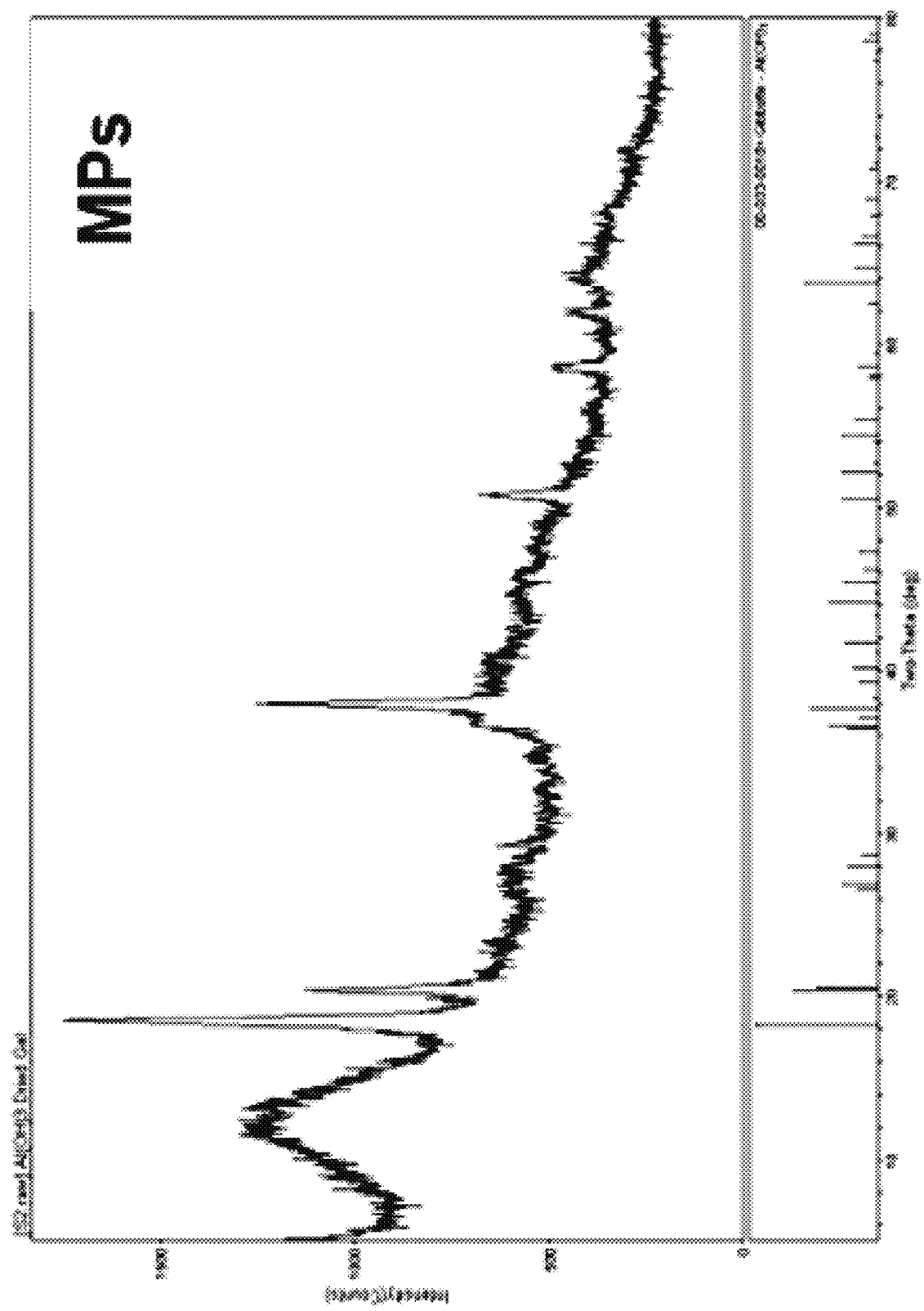

In order to evaluate the effect of the size of aluminum hydroxide particles on their adjuvant activity, aluminum hydroxide nanoparticles and microparticles with mean diameters of 112±6.2 nm and 9.3±2.2 µm, respectively, were prepared. FIG. 10A depicts the particle sizes (open bar) and zeta potentials (●) of aluminum hydroxide nanoparticles (NPs) and microparticles (MPs). At neutral pH, the zeta potentials of both particles were positive (FIG. 10A), but inversely correlated to their particle sizes. In other words, the zeta potential of the aluminum hydroxide microparticles was less positive than that of the aluminum hydroxide nanoparticles (FIG. 10A). The positive charge of aluminum hydroxide particles was likely due to the metallic hydroxyls on their surface, which could accept protons and show a positive zeta potential. Since the reduction of particle size increases the total surface area of the particles, the aluminum hydroxide nanoparticles are expected to have a relatively larger surface area than the microparticles, and thus more metallic hydroxyl groups on their surface, resulting in a more positive zeta potential. The aluminum hydroxide nanoparticles were stable when stored at 4° C. for a month, whereas the microparticles were slightly less stable (FIG. 10B), likely because the zeta potential of the nanoparticles was >30 mV, whereas the zeta potential of the microparticles was <30 mV, at which the electrostatic repulsion is not strong enough to prevent aggregation. The X-ray powder patterns of aluminum hydroxide particles are presented in FIGS. 10C and 10D. The nanoparticles were completely amorphous (FIG. 10C). The microparticles were mostly crystalline $Al(OH)_3$ (FIG. 10D), although the large peak in the left showed that some amorphous AlO(OH) materials existed as well (FIG. 10D).

Characterization of OVA-Adsorbed Aluminum Hydroxide Particles

Figure 11B:
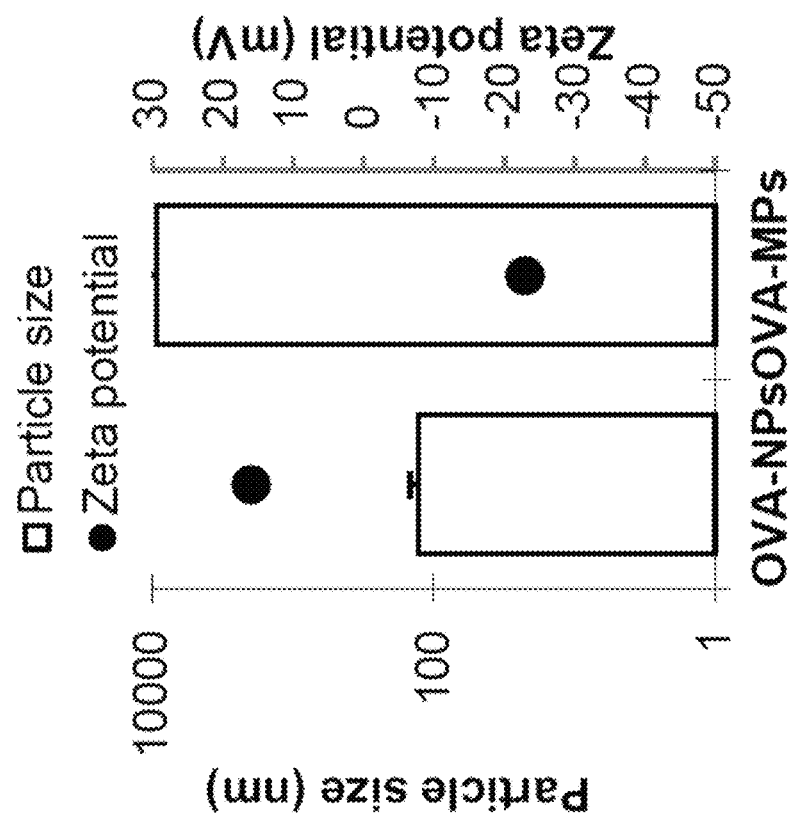
Figure 11A:
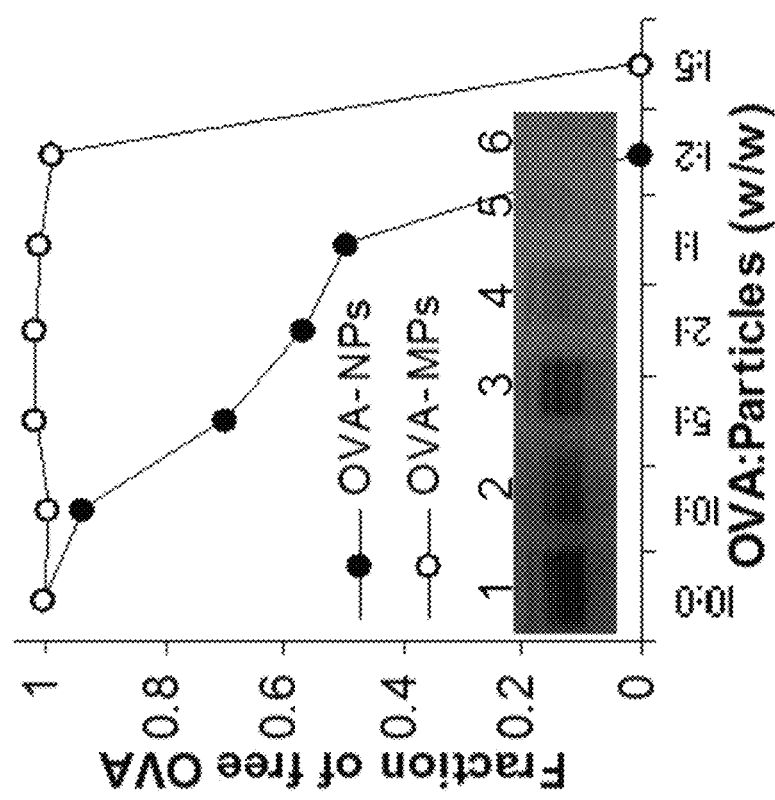

Shown in FIG. 11A are the sizes (open bar) and zeta potentials (●) of the aluminum hydroxide nanoparticles and microparticles after the adsorption of OVA protein at a 1:2 ratio (OVA vs. particle, w/w). The mean diameters of the OVA-adsorbed nanoparticles and microparticles were 129±20 nm and 9428±1734 nm, respectively; and their zeta potentials were 16±1.8 and −23±1.9, respectively. The sizes of both particles increased after the adsorption of OVA. Since OVA is net negatively charged at neutral pH (isoelectric point (pI), 4.7), after the adsorption of OVA, the zeta potentials of the resultant nanoparticles became less positive, and the zeta potential of microparticles even changed from positive to negative (FIG. 11A).

Shown in FIG. 11B are the fractions of free OVA when a fixed amount of OVA was mixed with an increasing amount of the aluminum hydroxide nanoparticles or microparticles. As expected, the fraction of unbound OVA decreased when the amount of aluminum hydroxide particles added was increased. When the ratio of OVA to nanoparticles was decreased to 1:2 and 1:5, the OVA protein bands can no longer be detected on the SDS-PAGE, indicating that all OVA protein were bound on the particles when OVA and particles were mixed at 1:2 ratio or lower. The adsorption of the OVA to the aluminum hydroxide microparticles was not as extensive as to the nanoparticles. Only when the OVA and microparticles weight ratio reached 1:5, the OVA protein bands were no longer detectable using SDS-PAGE (FIG. 11B). The mechanisms of the adsorption of OVA to aluminum hydroxide particles are likely two folds: (i) the electrostatic interaction between OVA and aluminum hydroxide particles because they have opposite net charges at neutral pH; and (ii) ligand exchange as OVA protein contains up to two phosphate groups, which could strongly bind to aluminum instead of a hydroxyl group. The higher protein adsorption capacity of the aluminum hydroxide nanoparticles is consistent with the larger total surface area of the nanoparticles, which contain more binding sites for protein adsorption. The smaller total surface area for the aluminum hydroxide microparticles limited the amount of proteins that can be adsorbed on them. Besides the effect of the surface area, the zeta potential of the aluminum hydroxide particles may have also contributed to the adsorption capacity. The zeta potential of the aluminum hydroxide nanoparticles was more positively than that of the microparticles (FIG. 10A). Therefore, the aluminum hydroxide nanoparticles may have attracted more OVA proteins to their surface.

FIGS. 11C and 11D depict SEM pictures of OVA-adsorbed aluminum hydroxide nanoparticles (OVA-NPs) and OVA-adsorbed aluminum hydroxide microparticles (OVA-MPs). FIG. 11E depicts a TEM picture of OVA-NPs.

Stability of OVA-Adsorbed Aluminum Hydroxide Nanoparticles

The OVA-adsorbed aluminum hydroxide nanoparticles cannot be stored as a suspension at 4° C. for more than 24 h, because the size of OVA-adsorbed nanoparticles was found increased by 7.2% after 24 h storage and 22.3% after 48 h storage as compared to their original size, respectively. As shown in FIG. 11A, after adsorption of OVA, the zeta potential of the aluminum hydroxide particles dropped into the range of −30 mV to +30 mV, in which the electrostatic repulsion is too weak to prevent aggregation. In addition, the small size of the nanoparticles favors aggregation to minimize the free energy on the nanoparticle surface. Therefore, we decided to lyophilize the OVA-adsorbed aluminum hydroxide nanoparticles and to evaluate the nanoparticle stability when stored as a lyophilized powder. The OVA-adsorbed aluminum hydroxide nanoparticles were successfully lyophilized with trehalose (2%) as a lyoprotectant (FIG. 12A). In a short-term 28-day study, the size of the lyophilized, OVA-adsorbed aluminum hydroxide nanoparticles did not change when stored as a lyophilized powder at 4° C. (FIG. 12B), indicating that storing the antigen-adsorbed aluminum hydroxide nanoparticles as a lyophilized powder is a potentially viable method to avoid aggregation during storage.

OVA-Adsorbed Small Aluminum Hydroxide Nanoparticles Induced a Stronger OVA-Specific Antibody Immune Response than OVA-Adsorbed Large Aluminum Hydroxide Microparticles.

Figure 13A:
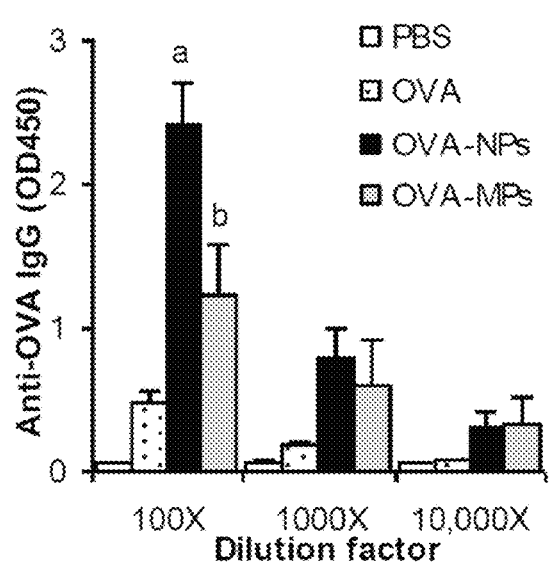
FIG. 13A-B.

Aluminum hydroxide particles with diameters in the range of 1-20 μm have been widely used in human vaccines. Previous data showed that nanoparticles with a mean diameter of around 200 nm have a more potent adjuvant activity than larger particles. To test whether small aluminum hydroxide nanoparticles of less than 200 nm can help an antigen to induce a stronger immune response than larger aluminum hydroxide microparticles, we compared the anti-OVA immune responses induced by OVA-adsorbed on aluminum hydroxide nanoparticles or microparticles. Data in FIG. 13A showed that the anti-OVA IgG level in mice that were immunized with the OVA-absorbed aluminum hydroxide nanoparticles was significantly higher than that in mice that were immunized the OVA alone or OVA-adsorbed microparticles at 100-fold dilution (p<0.001, OVA-NPs vs. OVA; p=0.018, OVA-NPs vs. OVA-MPs; p=0.05, OVA alone vs. large OVA-MPs).

Figure 13B:
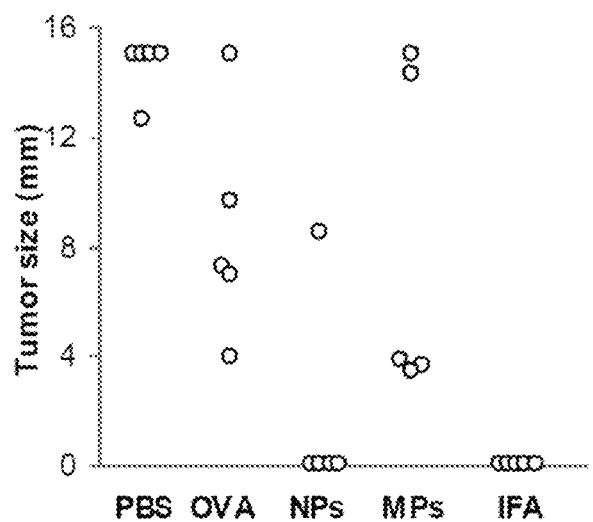

A tumor prevention study was carried out to evaluate the capability of OVA-adsorbed aluminum hydroxide nanoparticles against tumor growth. Twenty-one days after immunization with OVA-adsorbed aluminum hydroxide nanoparticles or microparticles, mice were challenged with the OVA-expressing B16-OVA tumor cells, and the tumor growth was monitored. As shown in FIG. 13B, 31 days after tumor cell injection, tumors were detected only in one of the 5 mice that were immunized with the OVA-adsorbed aluminum hydroxide nanoparticles. In contrast, all mice immunized with the OVA-adsorbed microparticles or with OVA alone developed tumors, suggesting that the immune responses induced by OVA-adsorbed aluminum hydroxide nanoparticles can inhibit tumor growth. The antitumor activity was likely antibody-mediated.

PA-Adsorbed Aluminum Hydroxide Nanoparticles Induced a Stronger PA-Specific Antibody Response than PA-Adsorbed Aluminum Hydroxide Microparticles The anthrax PA protein was used as a functional antigen in this experiment. Anthrax is a toxin-mediated disease, and anthrax toxin is consisted of three proteins, PA, lethal factor, and edema factor. PA proteins form a heptamer on the surface of cells, from which the edema factor and the lethal factor enter cells. Therefore, the induction of anti-PA antibody responses is critical and sufficient for a vaccine to prevent against anthrax. To further evaluate the adjuvant activity of the aluminum hydroxide particles, PA was absorbed on them at a particle to PA ratio of 5:1.

Figure 14A:
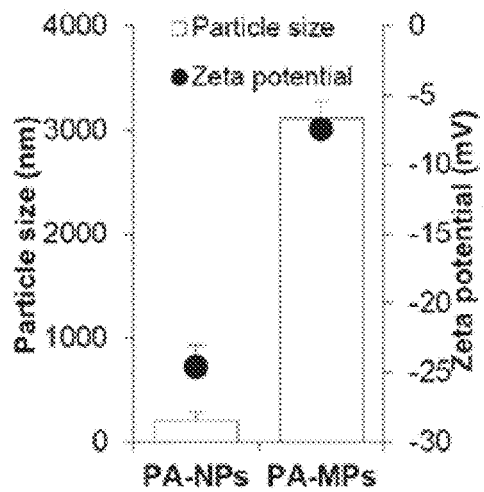
FIG. 14A-E.
Figure 14B:
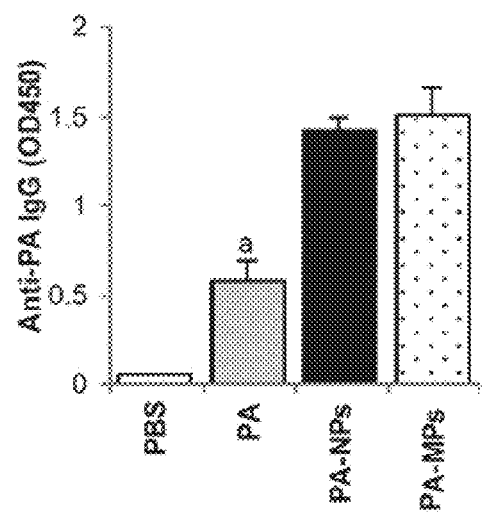
Figure 14C:
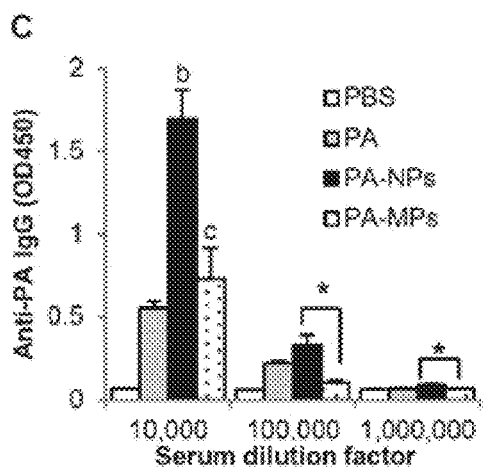
Figure 14D:
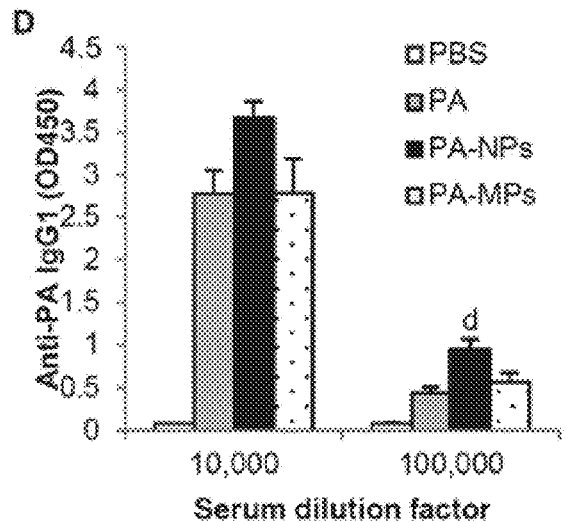
Figure 14E:
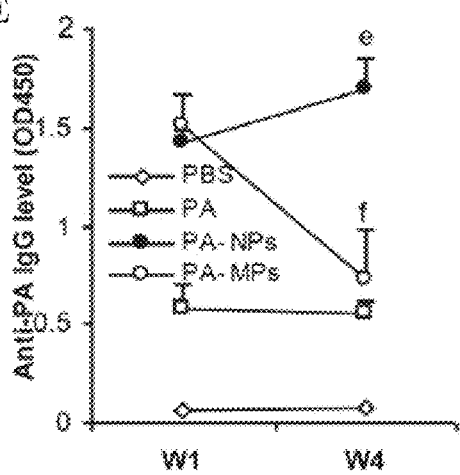

The mean diameters of the resultant PA-adsorbed aluminum hydroxide nanoparticles and microparticles were 204±25 nm and 7.1±3.4 μm, respectively (FIG. 14A, open bars). Mice were then immunized with the PA-adsorbed aluminum hydroxide nanoparticles or microparticles on days 0 and 14. One week after the first dose, anti-PA IgG was not detectable in any mice. One week after the second dose, significant anti-PA IgG responses were detected in mice that were immunized with the PA-adsorbed aluminum hydroxide nanoparticles or microparticles (FIG. 14B), although the levels of the anti-PA IgG response were not different. However, 4 weeks after the second immunization, the anti-PA IgG levels in mice that were immunized with the PA-adsorbed aluminum hydroxide nanoparticles were significantly higher than that in mice that were immunized with the PA-adsorbed aluminum hydroxide microparticles (FIG. 14C). Anti-PA IgG1 levels 4 weeks after the second immunization are shown in FIG. 14D. Significant higher anti-PA IgG1 level was detected in mice immunized with PA-adsorbed aluminum hydroxide nanoparticles as compared to in mice immunized with PA-adsorbed aluminum hydroxide microparticles. Anti-IgE level was not detected 4 weeks after immunization with PA-adsorbed aluminum hydroxide nanoparticles or microparticles (data not shown). The kinetics of the anti-PA IgG levels within 4 weeks is shown in FIG. 14E. It is clear that during the 4-week period after the second immunization, the anti-PA IgG level significantly increased in mice that were immunized with the PA-adsorbed aluminum hydroxide nanoparticles (p=0.005, week 1 vs. week 4), but significantly decreased in mice that were immunized with the PA-adsorbed aluminum hydroxide microparticles (p=0.005, week 1 vs. week 4).

Figure 15:
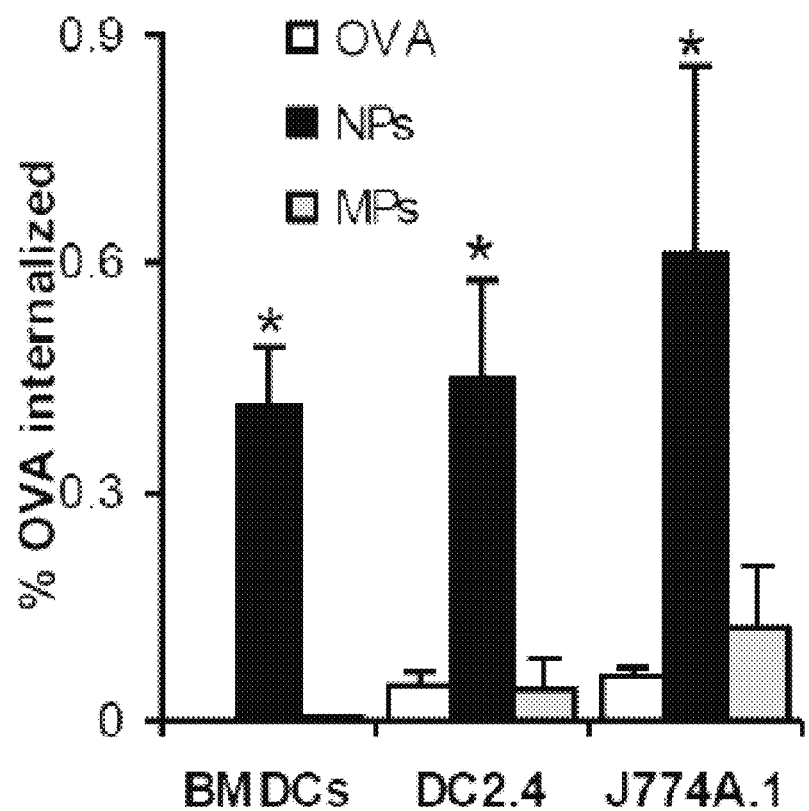
FIG. 15 More OVA was internalized when adsorbed on the aluminum hydroxide nanoparticles than when adsorbed on the aluminum hydroxide microparticles.
Figure 17A:
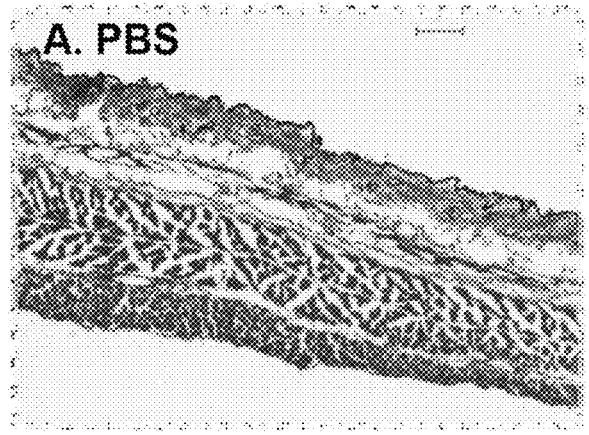
FIG. 17A-D. Microparticles and nanoparticles both induced local cutaneous inflammation in the injection sites when examined 40 days after the last dose, but the inflammation induced by the PA-adsorbed microparticles was much more severe, as shown by a greater number of accumulations of neutrophils around the injection sites and the pronounced epidermal hyperplasia.
Figure 17B:
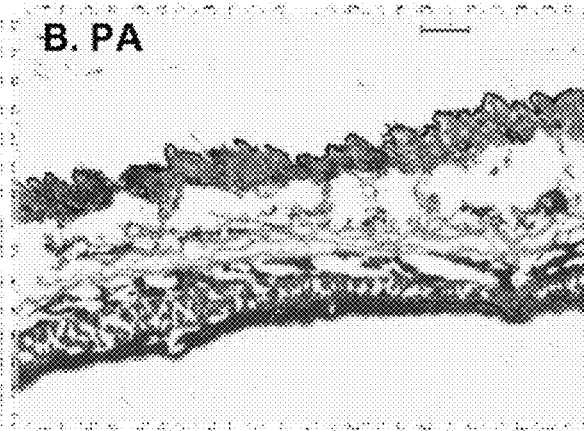
Figure 17C:
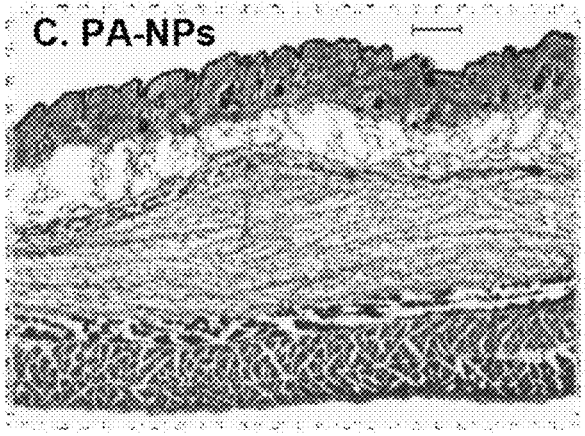
Figure 17D:
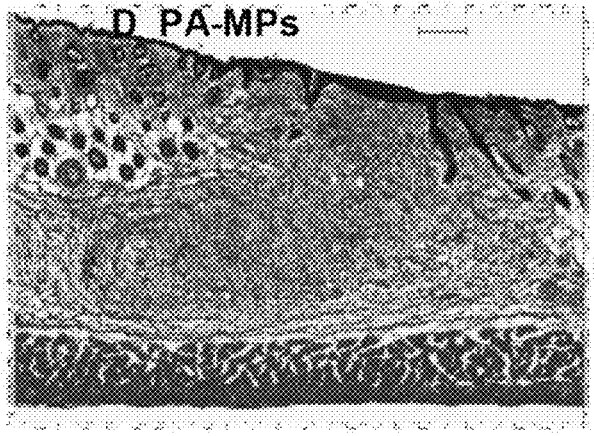
Figure 18A:
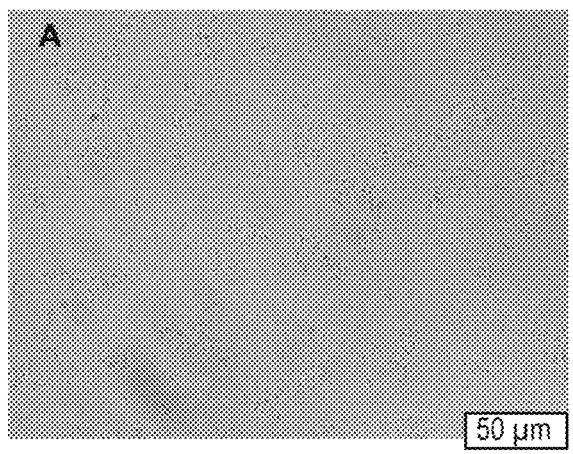
FIG. 18A-B. The Engerix-B human hepatitis B vaccine from GlaxoSmithKline contains aluminum hydroxide as an adjuvant. Trehalose was added into the vaccine suspension to reach a final concentration of 2% (w/v). The vaccine was then subjected to thin-film freeze-drying (TFFD) as mentioned previously. The moisture content in the TFFD powder was 1.15%. Shown in FIG. 18A is a representative image of fresh Engerix-B vaccine under an Olympus BX60 microscope.
Figure 18B:
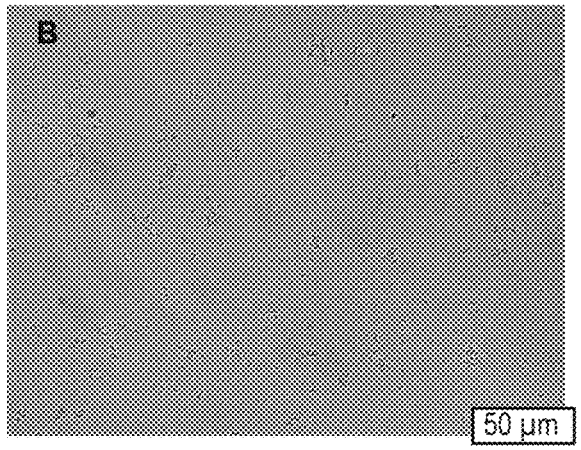
Figure 19A:
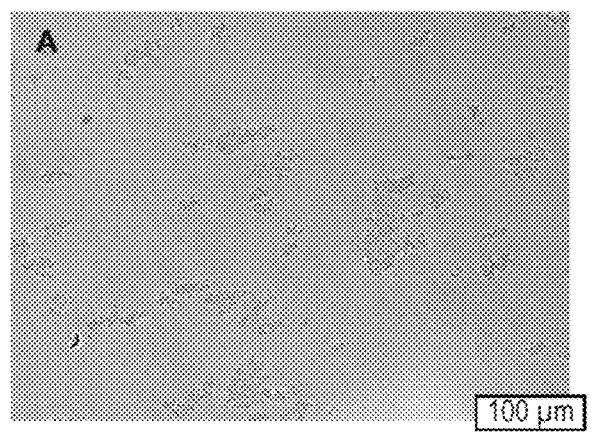
FIG. 19A-C. Concentrated tetanus toxoid (TT vaccine) contains aluminum potassium sulfate as an adjuvant. Trehalose was added into 1-ml vial of TT vaccine to reach a final concentration of 2% (w/v). The vaccine was then subjected to TFFD as mentioned previously. Three vials of the dried TT vaccine powder and three vials of fresh TT vaccine in 2% (w/v) of trehalose were frozen in −20° C. for 8 h and then thawed at 4° C. for 16 h. The freezing-and-thawing was repeated for three cycles. After the third cycle, the dry TT vaccine powder was reconstituted and examined under a microscope.
Figure 19B:
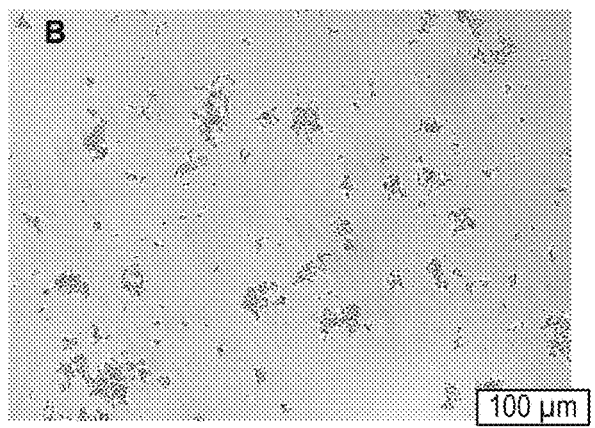
Figure 19C:
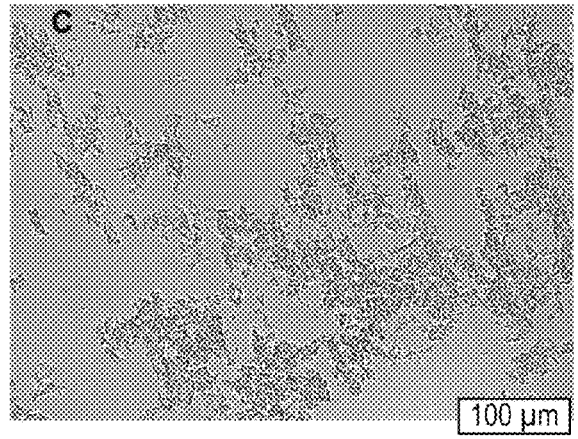
Figure 20A:
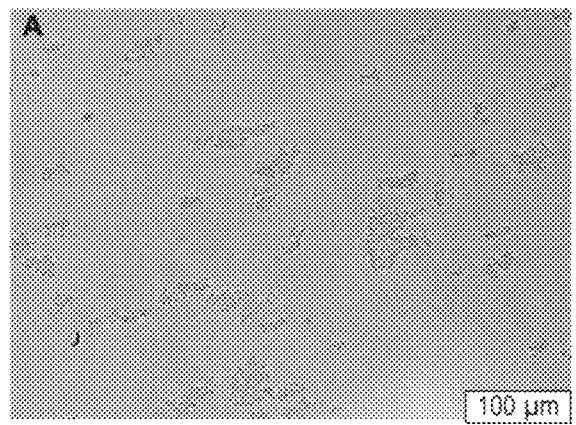
FIG. 20A-C. Concentrated tetanus toxoid (TT) vaccine contains aluminum potassium sulfate as an adjuvant. Trehalose was added into 1-ml vial of the TT vaccine to reach a final concentration of 2% (w/v). The vaccine was then subjected to TFFD. The dry TT vaccine powder was reconstituted and stored at 4° C. for 6 days.
Figure 20B:
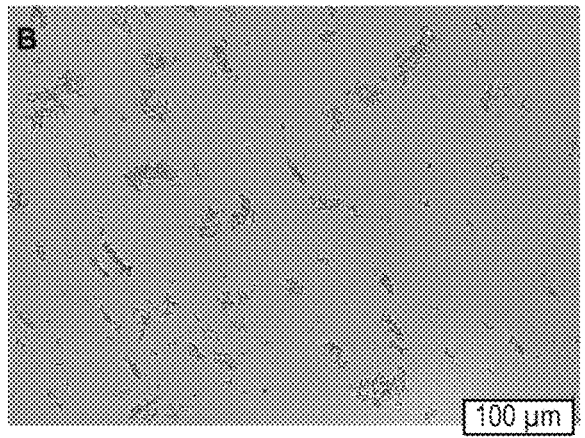
Figure 20C:
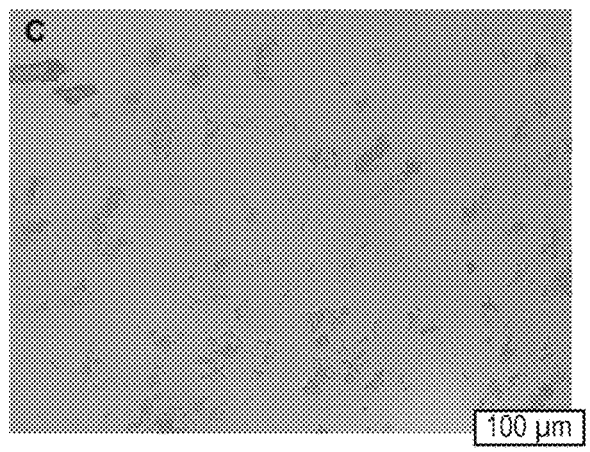
Figure 21A:
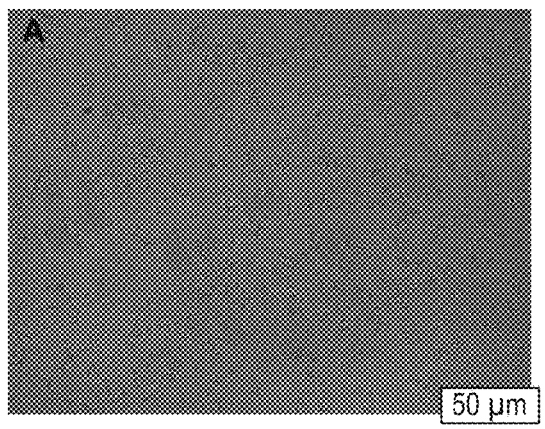
FIG. 21A-B. Alhydrogel™ (25 ml, 10 mg $Al^{3+}$/ml) was added into a 50 ml tube, followed by addition of 25 ml of OVA solution (1 mg/ml) at an OVA to $Al^{3+}$ weight ratio of 1:10. Trehalose was added to a final concentration of 2% (w/v). The sample was subjected to TFFD, and the dried powder was quickly transferred to a sealed container and stored in a desiccator at room temperature. Ten months later, the dry powder was reconstituted and observed under a microscope. Shown in FIG. 21A is a representative image of the OVA/Alhydrogel vaccine powder after 10 months of storage at room temperature. The particle size of the vaccine after reconstitution was 3.78±0.94 μm. A representative image of freshly prepared OVA/Alhydrogel vaccine is shown in FIG. 21B. It appears that there was not any significant aggregation after the dry powder was stored at room temperature for 10 months.
Figure 21B:
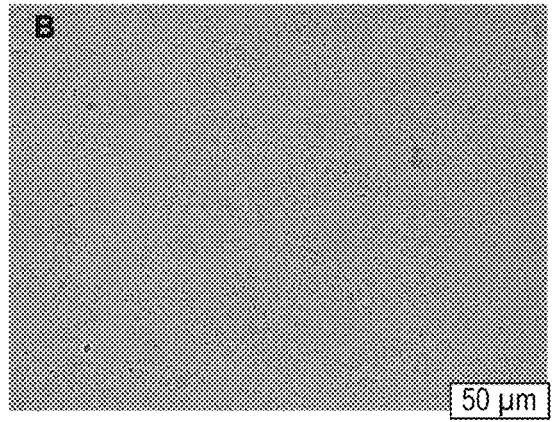

Uptake of OVA-Adsorbed Aluminum Hydroxide Particles by BMDCS, DC2.4 and J774A.1 Cells in Culture One important step for an antigen to induce an immune response is its uptake by APCs. Therefore, we evaluated the extent to which DCs and macrophages, two critical APCs, can take up OVA as an antigen adsorbed on aluminum hydroxide particles of different sizes. BMDCs, DC2.4, or J774A.1 cells in culture were incubated with fluorescein-labeled OVA adsorbed on aluminum hydroxide nanoparticles or microparticles for up to 6 h, and the % of OVA internalized by the cells was determined. In all three cells, more OVA was internalized when adsorbed on the aluminum hydroxide nanoparticles than when adsorbed on the aluminum hydroxide microparticles (FIG. 15). The fluorescence microscopic pictures in FIG. 16A-C are also supportive of the data in FIG. 15, and may explain why the aluminum hydroxide nanoparticles were more effective than the microparticles in facilitating the uptake of OVA by DC2.4 cells. Green fluorescence signal, an indication of the location of the OVA protein, was detected only inside cells that were incubated with OVA-adsorbed aluminum hydroxide nanoparticles, not in cells that were incubated with OVA-adsorbed aluminum hydroxide microparticles (FIG. 16A-C). In fact, for cells that were incubated with the OVA-adsorbed aluminum hydroxide microparticles, almost all fluorescence signals were extracellular (FIG. 16A-C), and it seemed that some OVA-adsorbed aluminum hydroxide microparticles were even larger than the cells (FIG. 16A-C), which may explain why the aluminum hydroxide microparticles did not facilitate the uptake of the OVA adsorbed on them (FIG. 15). Previous data showed that antigens eluted from adjuvants are taken up by DCs by macropinocytosis, while those remaining adsorbed are internalized with adjuvant particles by phagocytosis. Because of close to 100% of the OVA was adsorbed on the aluminum hydroxide nanoparticles, it is likely that phagocytosis or endocytosis was the predominant mechanism for the internalization of the OVA that was adsorbed on the aluminum hydroxide nanoparticles. In contrast, only less than 20% OVA was adsorbed onto the microparticles (at the OVA to particle ratio of 1:2). The small percentage of OVA that was internalized by DC2.4 cells incubated with the OVA-adsorbed aluminum hydroxide microparticles was probably from the macropinocytosis of the unbound OVA and OVA eluted from the microparticles. It has been reported that DCs are able to internalize particles with a diameter larger than that of cells. However, we could not find any internalization of the OVA-adsorbed aluminum hydroxide microparticles using fluorescence microscope. It has also been reported that nanoparticles (200-600 nm) were more efficiently taken up by macrophages in comparison to microparticles (2-8 μm). As shown in FIG. 15, the percentage of OVA internalized by macrophages was significantly higher when adsorbed on the aluminum hydroxide nanoparticles than that when adsorbed on microparticles. Thus, we suspect that ability of the aluminum hydroxide nanoparticles to more effectively facilitate the uptake of the OVA adsorbed on them by APCs is related to their potent adjuvant ability (FIGS. 13A-B to 14A-E).

Finally, a comparison of the internalization of the OVA by the macrophages (J774A.1 cells) and the DCs (BMDCs and DC2.4 cells) indicated that the % of OVA adsorbed on the aluminum hydroxide microparticles that was internalized by the macrophages was relatively higher than by the DCs (FIG. 15). This finding is in agreement with a previous report that macrophages can take up particles larger than 500 nm very effectively, whereas DCs are more effective in taking up smaller nanoparticles (<200 nm).

Aluminum Hydroxide Nanoparticles Induced a Milder Local Inflammation than Aluminum Hydroxide Microparticles Aluminum adjuvants have been administered safely to humans since 1932. Adverse reactions that have been reported with aluminum containing vaccines are generally local reactions including subcutaneous (s.c.) nodule, granulomatous inflammation, and sterile abscesses. In order to evaluate the safety profile of aluminum hydroxide nanoparticles, the injection sites were examined histologically. As shown in FIG. 17A-D, microparticles and nanoparticles both induced local cutaneous inflammation in the injection sites when examined 40 days after the last dose, but the inflammation induced by the PA-adsorbed microparticles was much more severe, as shown by a greater number of accumulations of neutrophils around the injection sites and the pronounced epidermal hyperplasia. It appears that the aluminum hydroxide nanoparticles have a more potent adjuvant activity than aluminum hydroxide microparticles, but are less pre-inflammatory than the microparticles.

33. Thin-Film Freeze Drying of OVA-Adsorbed Aluminum Hydroxide

Figure 22A:
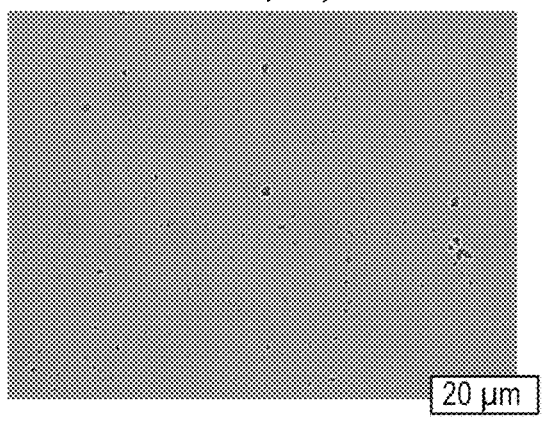
FIG. 22A-D. Representative microscopy images of OVA-adsorbed aluminum hydroxide (before FIG. 22A) and after lyophilization (FIG. 22B-D) with 2% trehalose (w/v)).
Figure 22B:
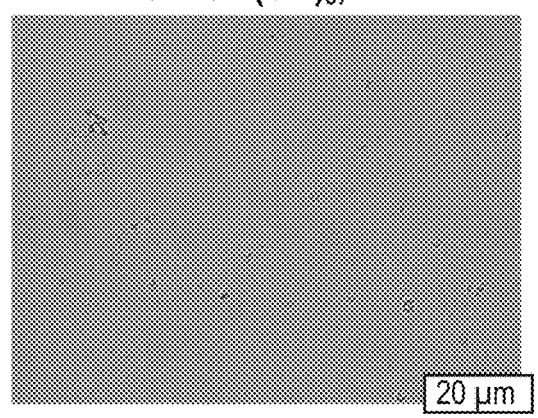
Figure 22C:
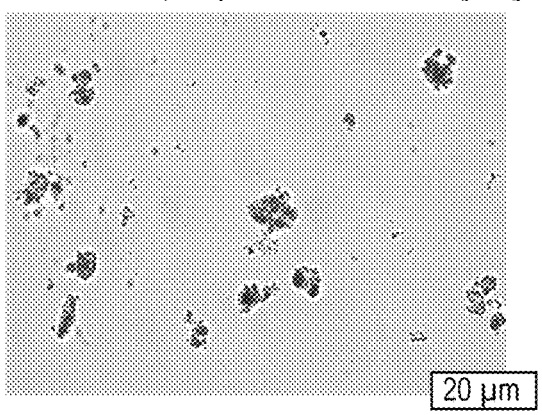
Figure 22D:
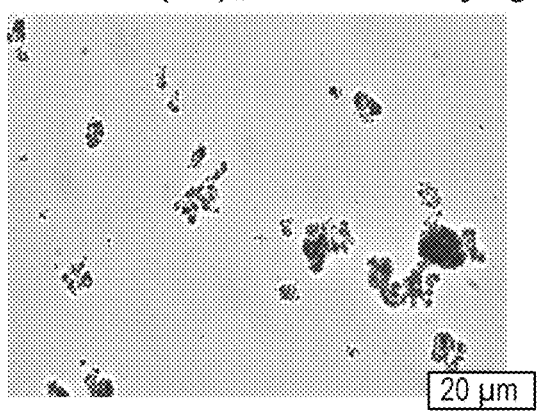

In order to test whether the TFFD can be used to lyophilize an aluminum hydroxide-adjuvanted, protein-based vaccine, OVA-adsorbed aluminum hydroxide was suspended in 2% (w/v) of trehalose and subjected to TFFD. A white powder was formed, which can be readily reconstituted with water, PBS, or normal saline with no or only minimal agitation. The moisture content in the powder was 1-3%. The size of the particles in the reconstituted OVA-adsorbed aluminum hydroxide was 9.7±2.5 μm, which is not different from the size of the particles in freshly prepared OVA-adsorbed aluminum hydroxide suspension (9.4±1.7 μm), demonstrating that the OVA-adsorbed aluminum hydroxide suspension can be successfully lyophilized into a dry powder form using TFFD without significant effect on the size of the particles in the vaccine suspension. The microscopic images in FIGS. 22A-B also show that subjecting the OVA-adsorbed aluminum hydroxide to TFFD did not cause significant aggregation. In contrast, when the same OVA-adsorbed aluminum hydroxide suspension was slowly frozen by placing it on a −80° C. or −20° C. shelf before lyophilization, significant aggregations were detected (FIGS. 22C-D). As mentioned by Zapata et al., aluminum hydroxide gel could form aggregates ranged from 65 to 160 μm after just one freeze-thaw cycle at −24° C. [M. I. Zapata et al., *Journal of pharmaceutical sciences*, 73 (1984) 3-8]. It is thought that the reason of particle coagulation is due to the large water crystals formed during the slow freezing process, which bring aluminum hydroxide particles close enough to overcome repulsive forces and cause aggregation, and the original aluminum hydroxide suspension could not be reproduced upon coagulation [Y. F. Maa et al., *Journal of pharmaceutical sciences*, 92 (2003) 319-332]. By increasing the freezing rate, only smaller ice crystals are formed as a result of a greater rate of nucleation, which are not strong enough to overcome the repulsive forces between particles, and particle aggregation is prevented consequently [Y. F. Maa et al., *Journal of pharmaceutical sciences*, 92 (2003) 319-332]. In TFF process, a solution or suspension is spread out on a cryogenic substrate to form a thin film in less than one second (cooling rate, ~100 K/s) [J. D. Engstrom et al., *Pharmaceutical research*, 25 (2008) 1334-1346], which may explain why there were not significant aggregation after the OVA adsorbed on aluminum hydroxide was subjected to TFFD. As mentioned early, it was reported previously that higher cooling/freezing rates help minimize agglomeration of vaccines adjuvanted with aluminum salts [Y. F. Maa et al., *Journal of pharmaceutical sciences*, 92 (2003) 319-332; A. Clausi et al., *Journal of pharmaceutical sciences*, 97 (2008) 5252-5262].

Figure 23A:
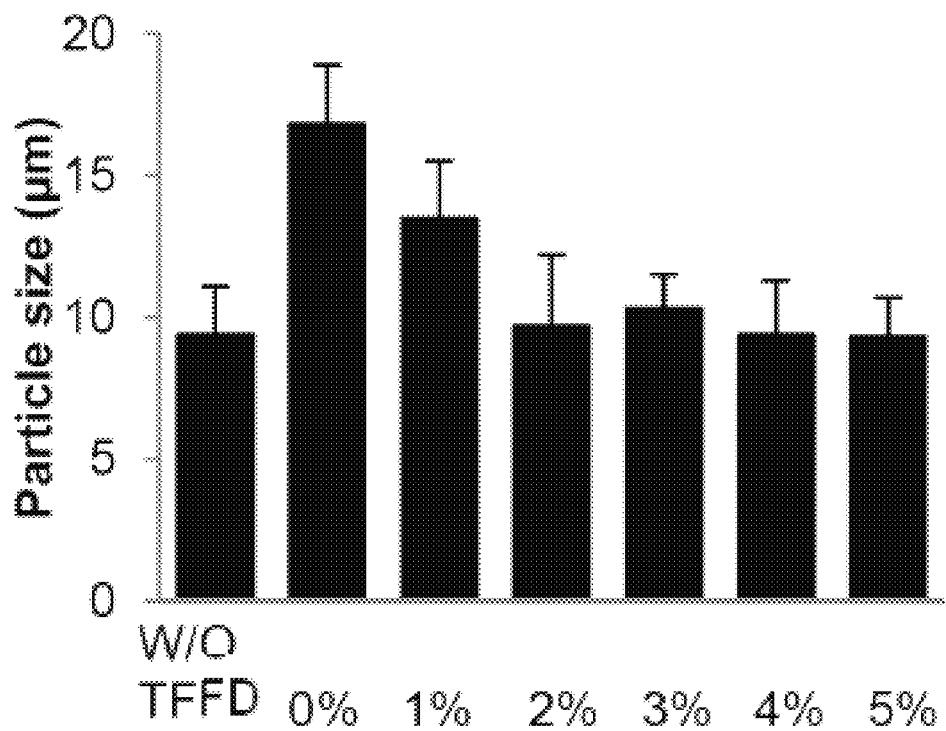
FIG. 23A-B. TFFD of OVA-adsorbed aluminum hydroxide in various concentrations of trehalose.
Figure 23B:
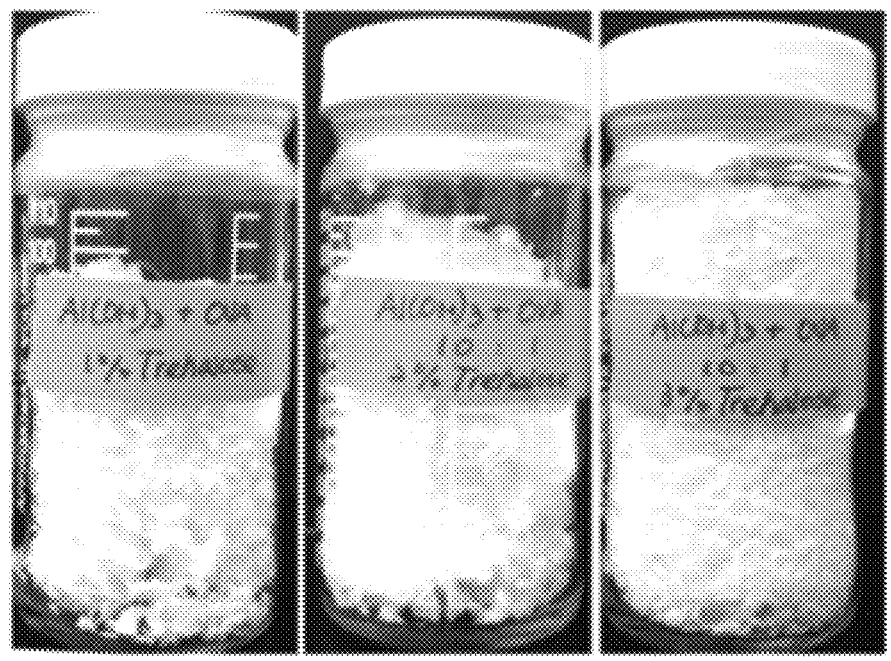

34. Thin-Film Freeze Drying of OVA-Adsorbed Aluminum Hydroxide in Various Concentrations of Trehalose Certain sugars, such as trehalose, mannitol, dextran, and sucrose, have been shown to be effective at maintaining protein activity and stabilize aluminum salts in vaccine formulations during freezing process [K. A. Overhoff et al., *J.DRUG.DEL.SCI. TECH*, 19 (2009) 89-98; A. L. Clausi et al., *Journal of pharmaceutical sciences*, 97 (2008) 2049-2061; L. Wolff et al., *Colloids and Surfaces A: Physicochemical and Engineering Aspects.*, 330 (2008) 116-126]. Trehalose forms fragile glass during freezing, resulting in an increase on the viscosity, which limits the mobility of protein molecules or aluminum salt particles and thus, prevents coagulation [A. L. Clausi et al., *Journal of pharmaceutical sciences*, 97 (2008) 2049-2061; W. Wang, *International journal of pharmaceutics*, 203 (2000) 1-60]. The formation of glass also resulted in a trehalose-containing phase with maximum concentration that prevents the non-ice concentration or pH-induced aggregation of aluminum salts during freezing [A. L. Clausi et al., *Journal of pharmaceutical sciences*, 97 (2008) 2049-2061]. Randolph's group studied the effect of the concentration of trehalose on spray freeze drying vaccines containing aluminum hydroxide or aluminum phosphate, and claimed in their patent that 5-20% (w/v) of trehalose was required to successfully spray freeze dry vaccines adjuvanted with aluminum salts [T. W. Randolph et al., W.I.P. Organization (Ed.), 2008]. To determine the optimal concentration of trehalose needed to prevent aggregation during TFFD, OVA-adsorbed aluminum hydroxide suspended in various concentrations of trehalose (i.e., 0%, 1%, 2%, 3%, 4%, 5%, w/v) was subjected to TFFD. As shown in FIG. 23A, when the OVA-adsorbed aluminum hydroxide suspension was subjected to TFFD in the absence of trehalose, the size of particles after reconstitution was significantly larger than that in the freshly prepared OVA-adsorbed aluminum hydroxide suspension, indicating that a cryoprotectant such as trehalose is needed to successfully convert the OVA-adsorbed aluminum hydroxide into a powder by TFFD. Trehalose at 1% (w/v) was not optimal (FIG. 1A); and at least 2% of trehalose was used to successfully lyophilize the OVA-adsorbed aluminum hydroxide into a powder following thin-film freezing (FIG. 22A). Shown in FIG. 23B are representative images of OVA-adsorbed aluminum hydroxide that were subjected to TFFD with 1%, 2%, and 3% (w/v) of trehalose, respectively. In the present study, trehalose alone was used during the TFFD process. It is expected that other cryoprotectants such as sucrose, glycine and other amino acids, and polyvinylpyrrolidone may also help to prevent aggregation during the TFFD process. Moreover, the concentration of trehalose needed to successfully thin-film freeze dry OVA-adsorbed aluminum hydroxide was only 2% (w/v). Trehalose at concentrations of above 7.5% is generally used when spray freeze dry vaccines adjuvanted with aluminum salts [A. L. Clausi et al., *Journal of pharmaceutical sciences*, 98 (2009) 114-121; A. Clausi et al., *Journal of pharmaceutical sciences*, 97 (2008) 5252-5262; T. W. Randolph et al., W.I.P. Organization (Ed.), 2008]. The particle size of the lysozyme vaccines increased slightly following freeze drying and reconstitution, as compared to the untreated lysozyme vaccines [A. Clausi et al., *Journal of pharmaceutical sciences*, 97 (2008) 5252-5262]. Interestingly, in their lysozyme vaccines, only 10% of the lysozyme was bound to aluminum salts [A. Clausi et al., *Journal of pharmaceutical sciences*, 97 (2008) 5252-5262].

Figure 24A:
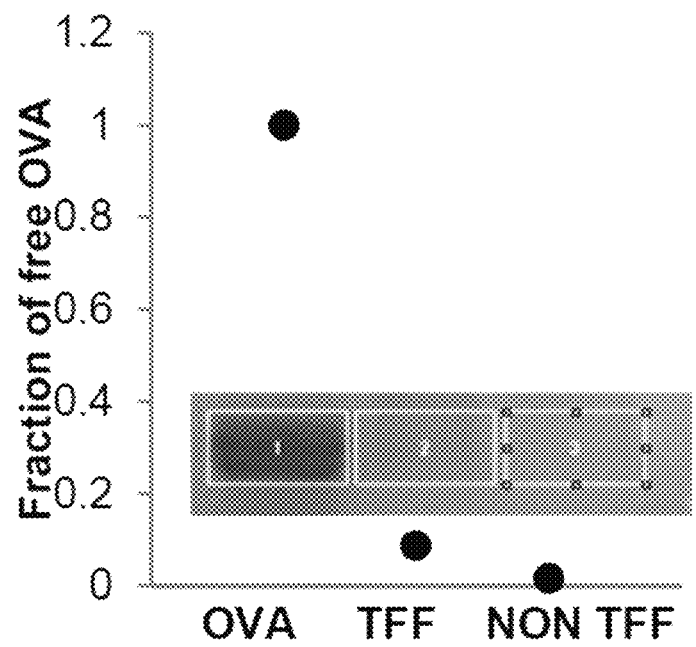
FIG. 24A-D. Characterization of OVA-adsorbed aluminum hydroxide powder prepared with TFFD.

35. Characterization of Thin Film Freeze Dried Powder of OVA-Adsorbed Aluminum Hydroxide To understand the influence of the TFFD process on aluminum hydroxide-adjuvanted vaccines, several studies were conducted to characterize the dried powder of the OVA-adsorbed aluminum hydroxide. Initially, a desorption of OVA from the aluminum hydroxide after the OVA-adsorbed aluminum hydroxide was subjected to TFFD was evaluated using SDS-PAGE. The intensity of the OVA band on the SDS-PAGE gel image is inversely correlated to the level of free unbounded OVA in the OVA-adsorbed aluminum hydroxide preparation (FIG. 24A). At the OVA to $Al^{3+}$ weight ratio of 1:10, all OVA were bound on the aluminum hydroxide (FIG. 24A, NON TFF). After the OVA-adsorbed aluminum hydroxide was subjected to TFFD and reconstitution, the percent of OVA that remained adsorbed on the aluminum hydroxide was estimated to be 92% (FIG. 22A, TFF), indicating that about 8% of the loosely bound OVA protein was desorbed from aluminum hydroxide. This 92% binding efficiency still meets the United States Food and Drug Administration (FDA) requirement for vaccines adjuvanted with aluminum salts. For example, 75% adsorption to aluminum salts is the minimum requirement for diphtheria toxoid and tetanus toxoid antigens [L. J. Braun, *Interactions between antigen and adjuvant: Implications for formulation*, (2012)].

Figure 24B:
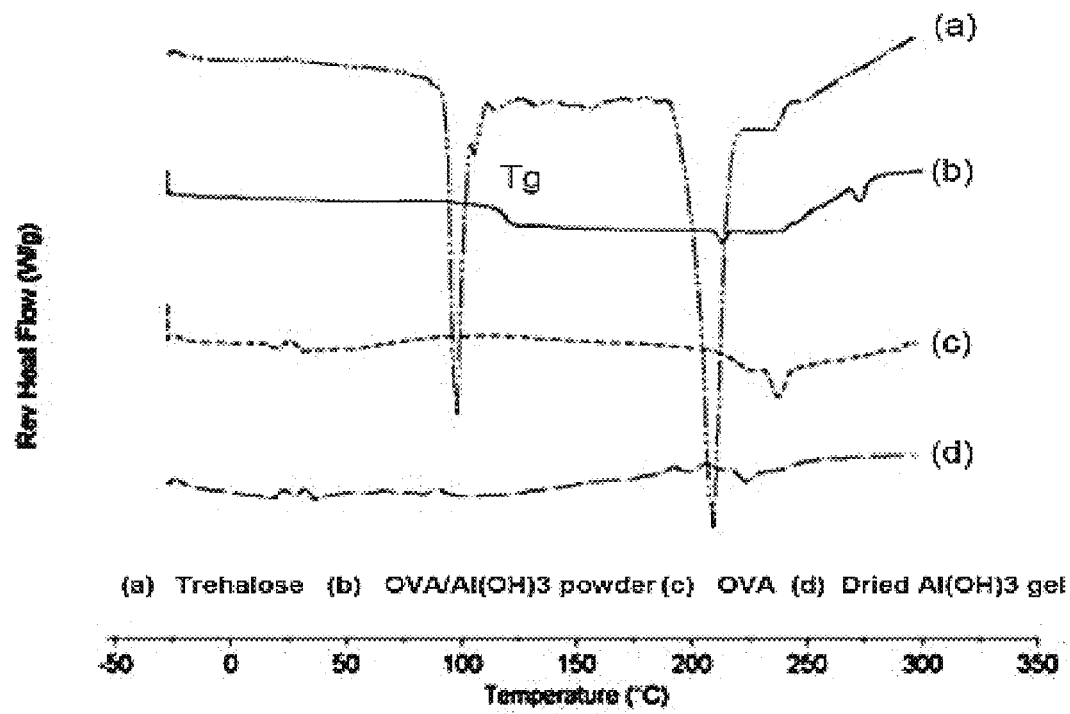

Modulated DSC was used to study the thermal properties of the OVA-adsorbed aluminum hydroxide dry powder. The DSC thermogram of the OVA-adsorbed aluminum hydroxide dry powder shows a glass transition temperature (Tg) of about 120° C. (FIG. 24B), indicating that the OVA-adsorbed aluminum hydroxide particles suspended in trehalose solution may have formed a glass after they were subjected to TFFD [L. M. Crowe et al., *Biophysical Journal*, 71 (1996) 2087-2093]. The high Tg value of ~120° C. suggests that the OVA-adsorbed aluminum hydroxide dry powder is highly stable [J. Buitink et al., *Biophysical Journal*, 79 (2000) 1119-1123; W. Wang, *Internatianl Journal of Pharmaceutics*, 203 (2000) 1-60].

Figure 24C:
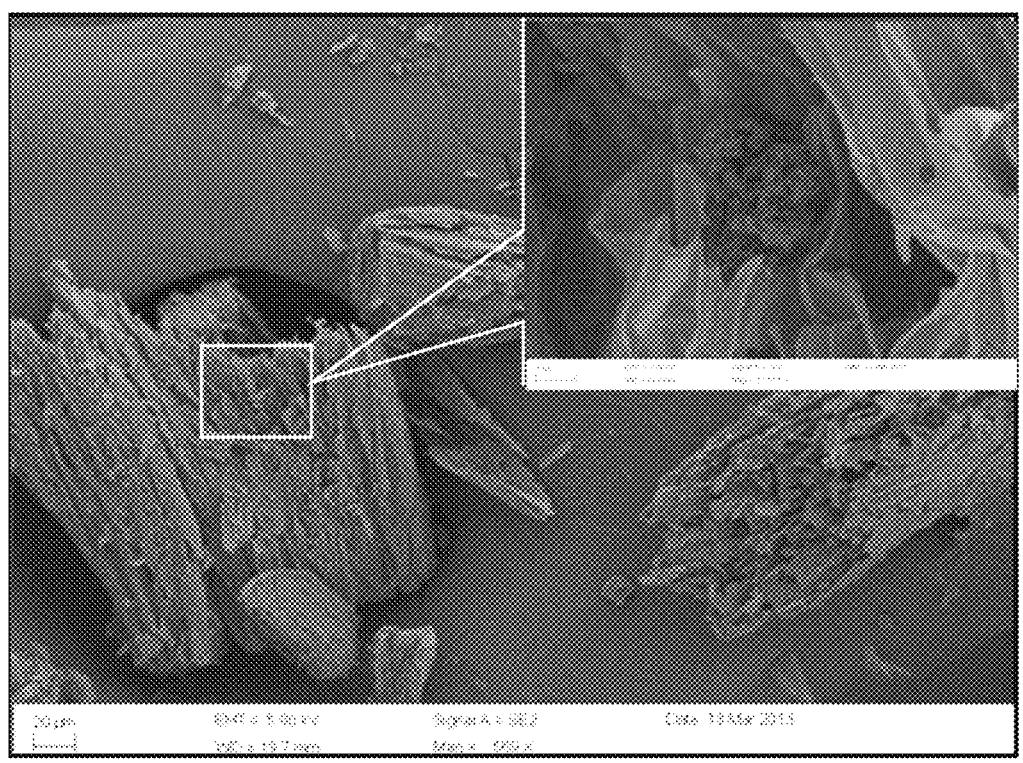
Figure 24D:
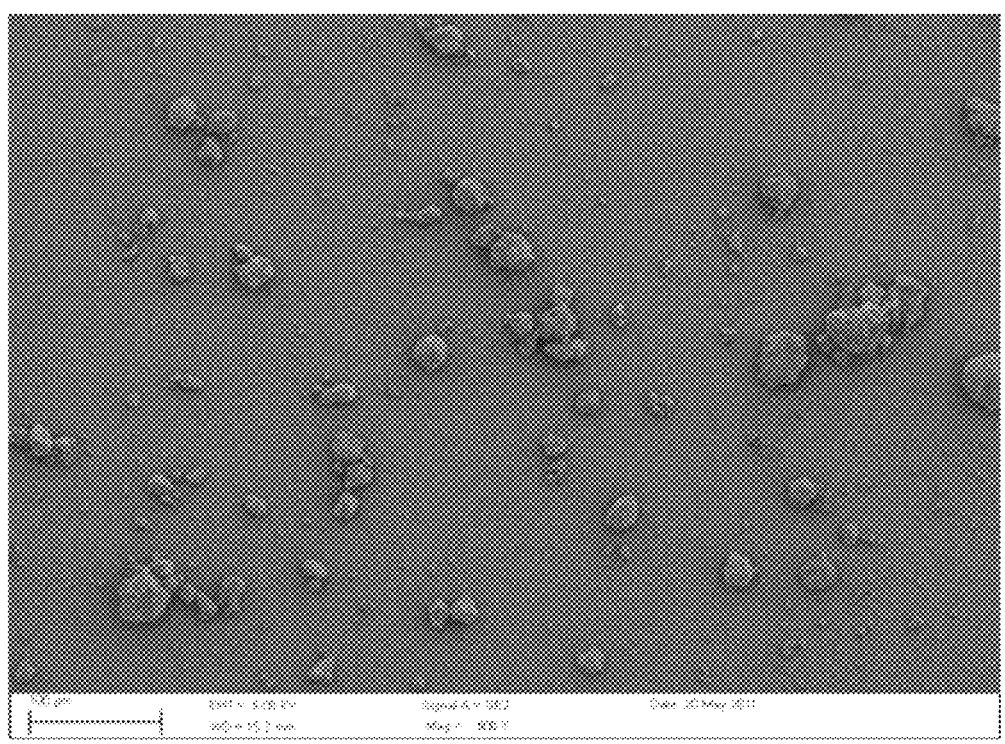

Shown in FIG. 24C is a representative SEM image of the OVA-adsorbed aluminum hydroxide dry powder. It appears that the OVA-adsorbed aluminum hydroxide particles, which have a rough surface and irregular shape (FIG. 24D), are embedded in the bulk structure of the trehalose (FIG. 24C inset). Therefore, it is likely that the trehalose surrounding the OVA-adsorbed aluminum hydroxide particles prevented the particles from interacting with each other during the freeze drying process, and thus prevented their aggregation.

Figure 25A:
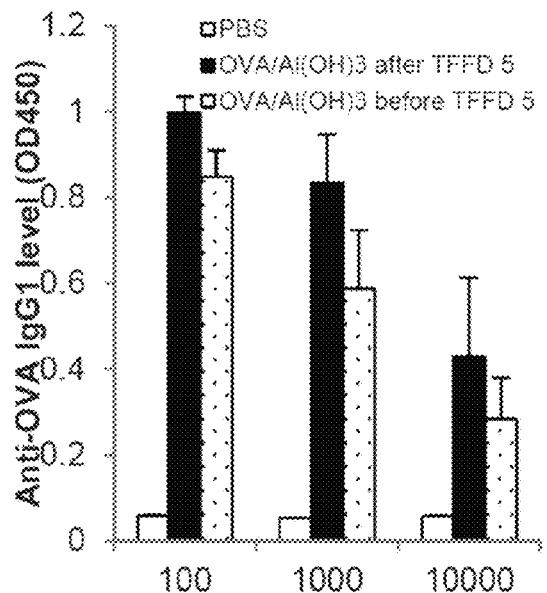
FIG. 25A-C. Anti-OVA IgG levels in mice immunized with OVA-adsorbed aluminum hydroxide, before and after TFFD. Female BALB/c mice (n=5) were s.c. injected with OVA-adsorbed aluminum hydroxide, before or after lyophilization and reconstitution, on days 0, 14 and 28 with 5 μg (FIG. 25A), 10 μg (FIG. 25B), or 20 μg (FIG. 25C) of OVA per mouse. The ratio of OVA to aluminum was 1 to 10. Sterile PBS and OVA alone (10 μg) in PBS were used as controls. Total anti-OVA IgG levels in serum samples were measured 16 days after the third dose.
Figure 25B:
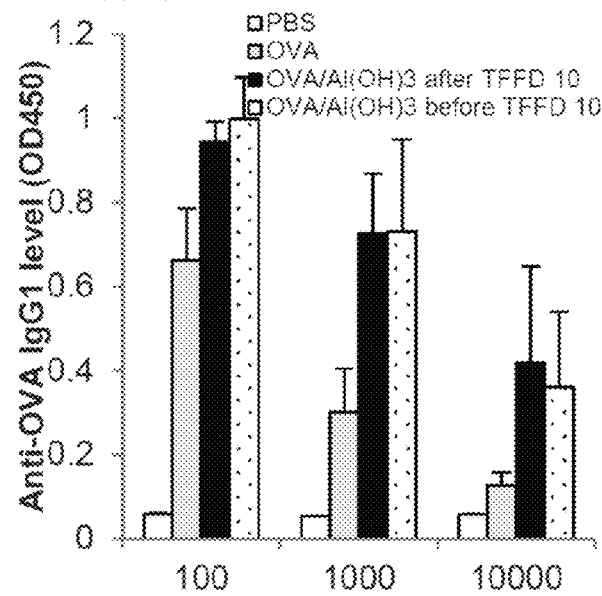
Figure 25C:
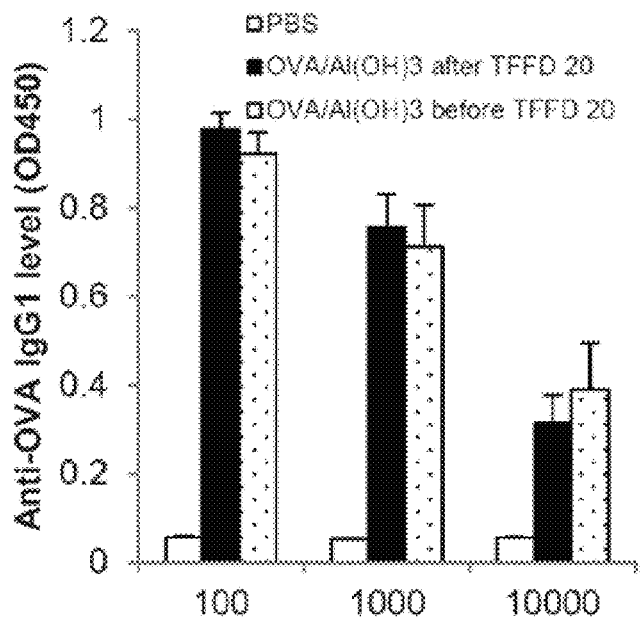

36. The Immunogenicity of the OVA-Adsorbed Aluminum Hydroxide after Thin-Film Freeze Drying A major limitation of current aluminum salt-adjuvanted vaccines is that the vaccine suspensions have to be kept at 2-8° C. and may not be exposed to freezing conditions intentionally or accidentally, because freezing causes irreversible coagulation and aggregation that may damage the vaccines and decrease their potency [H. HogenEsch, *Vaccine*, 20 Suppl 3 (2002) S34-39]. As reported by Diminsky et al, the aggregation formed during freezing often results in immunogenicity loss [D. Diminsky et al., *Vaccine*, 18 (1999) 3-17]. To test whether the OVA-adsorbed aluminum hydroxide after subjected to TFFD retains its immunogenicity, the anti-OVA immune responses induced by OVA-adsorbed aluminum hydroxide, freshly prepared or reconstituted from TFDD powder were evaluated in a mouse model. As shown in FIG. 25, the anti-OVA IgG levels in mice that were immunized with OVA-adsorbed aluminum hydroxide following TFFD and reconstitution were not different from that in mice that were immunized the freshly prepared OVA-adsorbed aluminum hydroxide, regardless of the dose of OVA antigen used (i.e., 5, 10, or 20 µg/mouse/injection). Clearly, the TFFD process not only avoided the aggregation of the OVA-adsorbed aluminum hydroxide particles, but also preserved the immunogenicity of the vaccine.

37. Thin-Film Freeze Drying of OVA-Adsorbed Aluminum Phosphate and OVA-Adsorbed Alhydrogel®

Figure 26A:
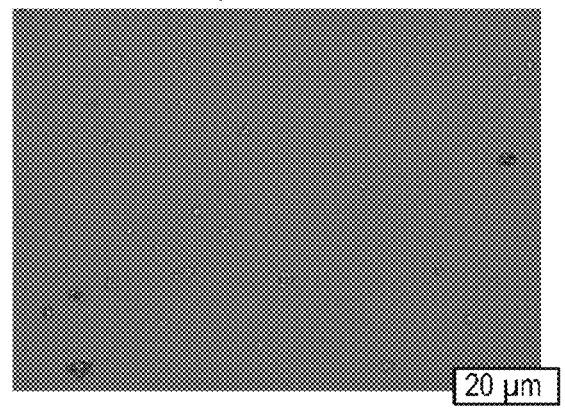
FIG. 26A-C. TFFD of OVA adjuvanted with aluminum phosphate or Alhydrogel® and its stability at room temperature.
Figure 26B:
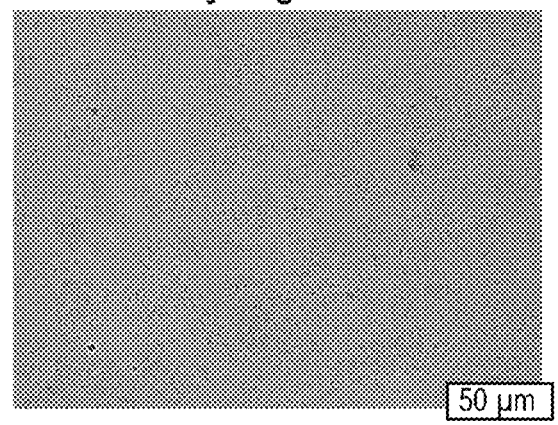

Both aluminum hydroxide and aluminum phosphate are commonly used in human vaccines. Therefore, we also tested whether a protein antigen adjuvanted with aluminum phosphate can be successfully lyophilized by TFFD using OVA as a model antigen. Moreover, in the above studies, the aluminum hydroxide suspension was prepared in our own laboratories by dispersing dried aluminum hydroxide gel (USP grade) in water. Alhydrogel® (2%, w/v) is a commercially available aluminum hydroxide wet gel suspended in normal saline. Therefore, we also tested the feasibility of drying OVA-adsorbed Alhydrogel® using TFFD. Both OVA-adsorbed aluminum phosphate and OVA-adsorbed Alhydrogel® were successfully converted into powders using TFFD. Both dried samples appeared as light white-colored powder and were easily reconstituted in water, normal saline, or PBS with no or minimum agitation. As shown in FIGS. 26A-B, no large aggregation was detected under microscope. The particle size of OVA-adsorbed aluminum phosphate after subjected to TFFD and reconstitution was 9.66±2.52 µm. The particle sizes of OVA-adsorbed Alhydrogel® before and after TFFD and reconstitution were 6.37±0.02 µm and 7.59±0.22 µm, respectively. Clearly, the TFFD can be used to convert vaccines adjuvanted with aluminum phosphate or with the commercially available Alhydrogel® into a dry powder.

Figure 26C:
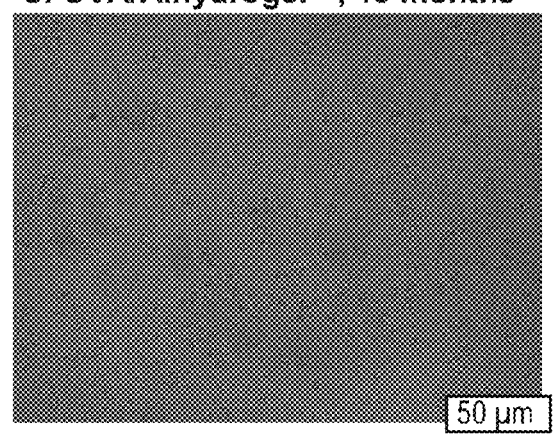

The dry OVA-Alhydrogel powder was stored in a desiccator at room temperature. Shown in FIG. 26C is a representative microscopic image of the OVA-Alhydrogel® powder reconstituted after about 10 months of storage at room temperature. It appears that 10 months of storage of the OVA-Alhydrogel® dry powder at room temperature did not lead to any significant aggregation. It is likely that the amorphous glass of trehalose with OVA-aluminum hydroxide particles embedded in helped prevent the interaction of the particles, and thus their aggregation, during the storage [D. Chen, D. Kristensen, *Expert review of vaccines*, 8 (2009)

547-557; B.S. Chang et al., *Archives of biochemistry and biophysics,* 331 (1996) 249-258]. Therefore, the vaccine powder prepared with TFFD can be kept in a cold-chain (2-8° C.), but may also be stored at room temperature. A comprehensive long-term stability test is underway to test the feasibility of storing the vaccine powder at room temperature.

38. The Preparation of a Dry Powder of an Adjuvanted, Concentrated Tetanus Toxoid Vaccine.

In order to test whether our method of preparing vaccines having aluminum-containing adjuvants in the dry solid form that are suitable for reconstitution is applicable to currently marketed vaccines, we used the Tetanus Toxoid Concentrated, Adjuvanted Detoxified Toxin (Cat. #11411, 10×1 ml, 10×1 dose) from Colorado Serum Company (Denver, Colo.). This tetanus toxoid adsorbed vaccine is used for the vaccination of healthy domestic animals. It is formulated by adsorbing detoxified tetanus toxin (i.e., tetanus toxoid) on aluminum potassium sulfate (as an adjuvant). Initially, we diluted 1 ml of the adjuvanted, concentrated tetanus toxoid vaccine with sodium phosphate buffer (pH 6.3) in a 50 ml tube, followed by the addition of trehalose (2% or 3%, w/v). The vaccine was processed by thin-film freezing as mentioned in Experiment 1, and the frozen liquid was removed using a VirTis Advantage bench top tray lyophilizer. The obtained dry powders were stored in a desiccator at room temperature before use. The morphology and size of the adjuvanted, concentrated tetanus toxoid vaccine and its reconstituted dried powders were examined using an Olympus BX60 microscope (Olympus America, Inc., Center Valley, Pa.) and an Sympatec Helos laser diffraction instrument (Sympatec GmbH, Germany) equipped with a R3 lens.

Figure 9A:
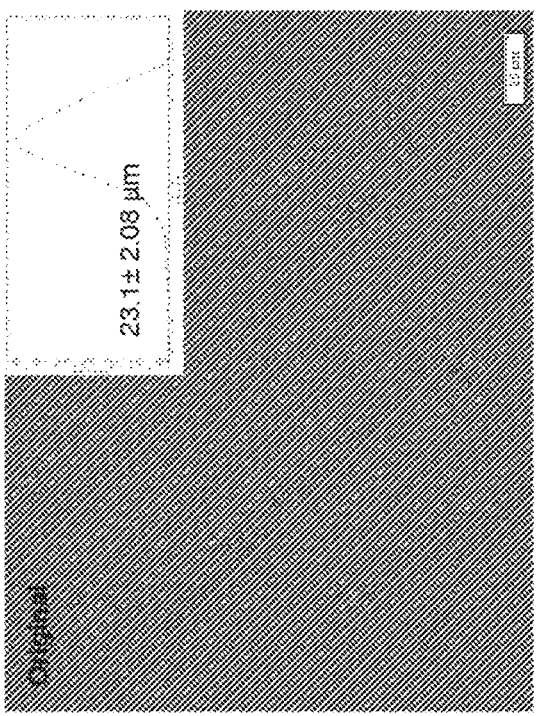
FIG. 9A-C.
Figure 9B:
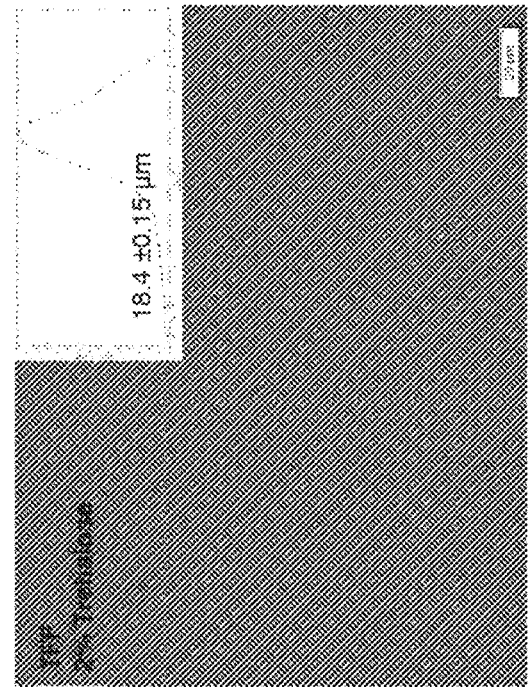
Figure 9C:
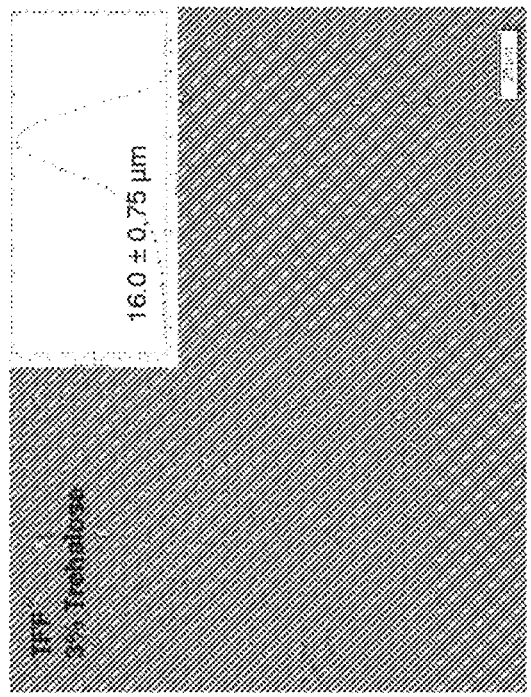

FIG. 9A shows the microscopic image of original adjuvanted, concentrated tetanus toxoid vaccine, which have particles of irregular shapes with a particle diameter of 23.1±2.1 μm. Reversible aggregation was observed in the original suspension. FIGS. 9B-C show the microscopic images of the adjuvanted, concentrated tetanus toxoid vaccine after dried with 2% or 3% trehalose into powders and then reconstituted in sodium phosphate buffer. Shown in the inset are the particle sizes determined using the Sympatec Helos laser diffraction instrument. Apparently, our drying process did not significantly increase the size of the adjuvanted, concentrated tetanus toxoid vaccine.

Figure 27A:
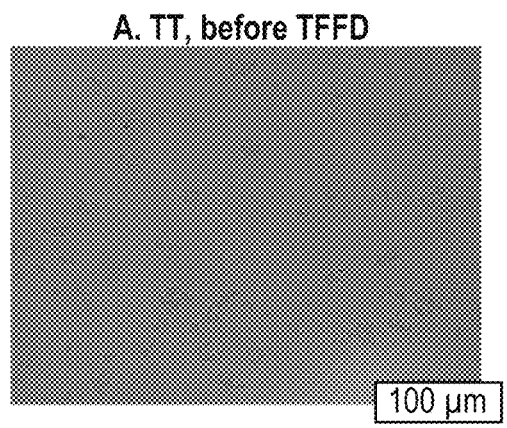
FIG. 27A-H. TFFD of tetanus toxoid vaccine and Engerix-B.
Figure 27B:
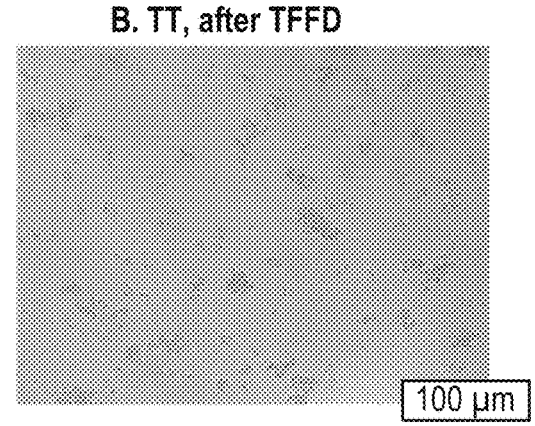

39. Thin-Film Freeze Drying of Commercial Veterinary Tetanus Toxoid Vaccine and Human Hepatitis B Vaccine In order to further validate the applicability of the TFFD in drying vaccines adjuvanted with aluminum salts, tetanus toxoid concentrated, adjuvanted detoxified toxin, a veterinary TT vaccine, and Engerix-B, a human hepatitis B vaccine, were subjected to TFFD. The TT vaccine is formulated by precipitating detoxified tetanus toxin with aluminum potassium sulfate in a phosphate buffer containing phosphate, sulfate, and bicarbonate ions [O. H. D. T., *Vaccine Adjuvants: Preparation methods and Research protocols*, Humana Press, 2000]. The final vaccine formulation is TT adjuvanted with amorphous aluminum hydroxyl phosphate sulfate [O. H. D. T., *Vaccine Adjuvants: Preparation methods and Research protocols*, Humana Press, 2000]. The TT vaccine concentrated was diluted, and trehalose was added to a final concentration of 2% (w/v) before the vaccine was subjected to TFFD. Shown in FIG. 27A and FIG. 27B are representative microscopic images of the original TT vaccine after dilution and the TT vaccine following TFFD and reconstitution, respectively. The particles in the original vaccine have irregular shape and an average diameter of 23.1±2.1 μm. The large particles in FIG. 27A are likely due to reversible flocculation. Large aggregates were not detected in the TT vaccine after TTFD and reconstitution (FIG. 27B), and the average particle size of reconstituted TT vaccine was 18.4±0.2 μm. Clearly, subjecting the TT vaccine to TFFD (and reconstitution) did not cause any significant aggregations.

Figure 27C:
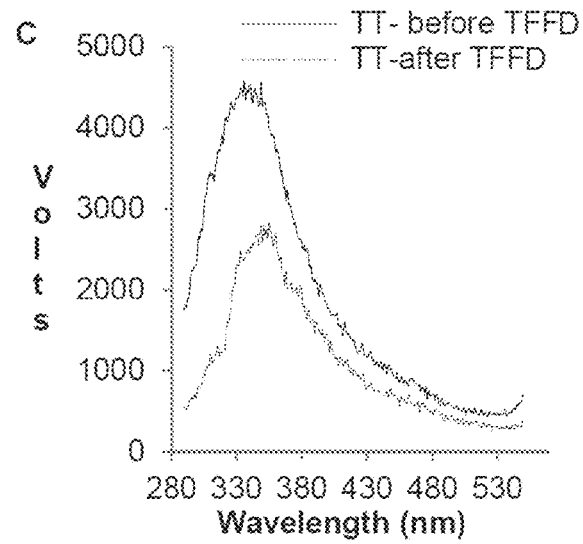
Figure 27D:
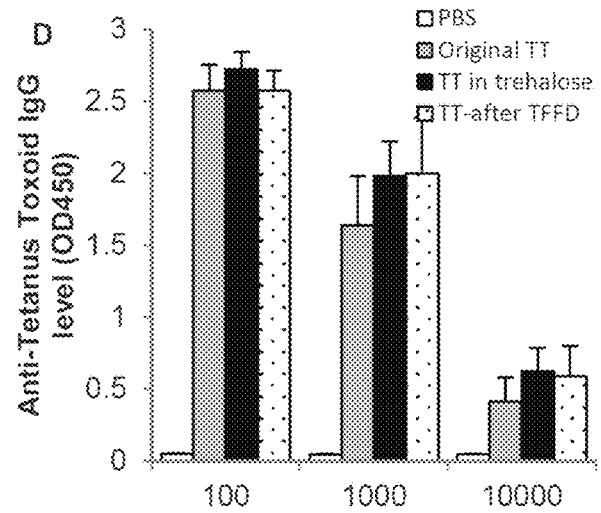

To investigate whether the TFFD process significantly altered the structure of the tetanus toxoid protein, the intrinsic fluorescence spectra of the TT vaccine before and after it was subjected to TFFD were acquired and compared. As shown in FIG. 27C, the fluorescence spectrum of the TT vaccine after TFFD and reconstitution only shifted slightly right (about 20 nm) when compared to the freshly diluted TT vaccine. In addition, the fluorescence intensity of the TT vaccine following TFFD and reconstitution was also relatively lower, probably related at least in part to antigen desorption during the TFFD process as shown in FIG. 24A. In addition, freeze drying is known to perturb the structure of proteins at any stage of the process, including freezing, drying, and reconstitution [A. L. Clausi et al., *Journal of pharmaceutical sciences,* 98 (2009) 114-121; T. Arakawa et al., *Advanced drug delivery reviews,* 46 (2001) 307-326; J. F. Carpenter et al., *Pharmaceutical research,* 14 (1997) 969-975]. The TFFD may have slightly altered the structure of the detoxified tetanus toxoid. However, it is unclear how the TFFD have increased the polarity of the environment surrounding the tryptophan residues in the detoxified tetanus toxoid to induce a slight right shift in the spectrum. Fortunately, when the immunogenicity of the TT vaccine before and after the TFFD (and reconstitution) was tested and compared in a mouse model, the anti-tetanus toxin IgG levels in all the immunized groups were not significantly different (FIG. 27D), demonstrating that the potency of the vaccine was preserved after it was subjected to TFFD and reconstitution. It appears that the slight protein structure change induced by the TFFD process did not significantly change the immunogenicity of the antigen.

Figure 27E:
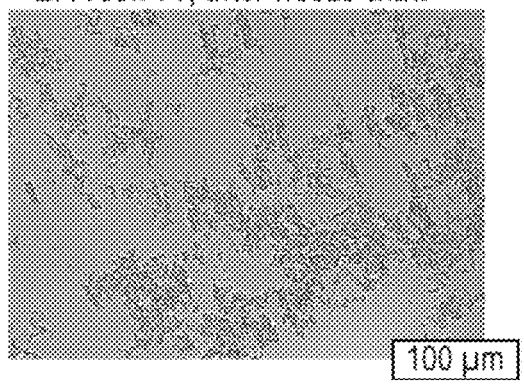
Figure 27F:
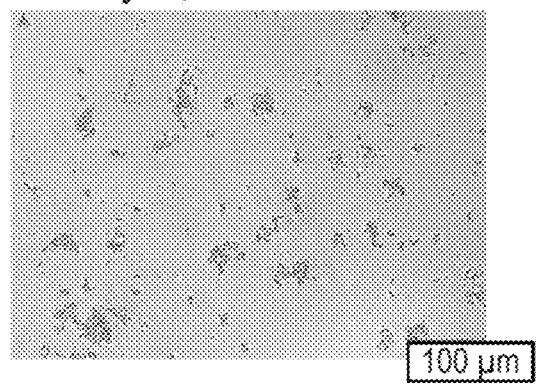

To test whether the TT vaccine after TFFD is still sensitive to inadvertent freezing (and thawing), the dried TT vaccine powder was subjected to three cycles of freeze-and-thaw, reconstituted, and then examined under microscope. As a control, fresh TT vaccine with 2% (w/v) of trehalose was also subjected to the same freeze-and-thaw cycles. As shown in FIG. 27E, repeated freezing-and-thawing of the TT vaccine in suspension caused significant aggregation. However, subjecting the dried TT vaccine powder to the same freezing-and-thawing cycles did not cause any significant aggregation (FIG. 27F), demonstrating that the vaccine powder prepared with TFFD is not sensitive to freezing conditions anymore. It is noted that to prepare the TT vaccine powder that was subjected to the repeated freeze-and-thaw cycles, the trehalose concentration was adjusted to 2% (w/v) by adding trehalose powder directly into the original TT vaccine, without further dilution.

Figure 27G:
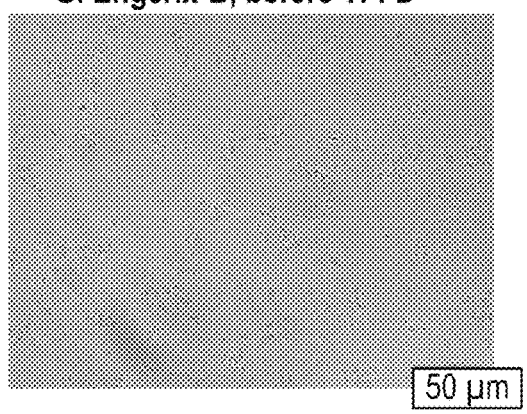
Figure 27H:
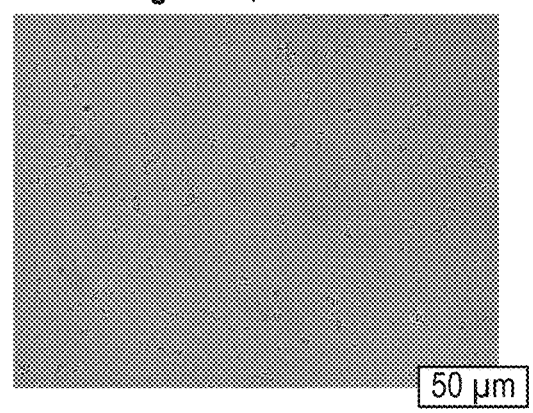

Engerix-B vaccine is a human hepatitis B vaccine, which contains human hepatitis B virus surface antigen adjuvanted with aluminum hydroxide. To further test the applicability of the TFFD process in drying vaccines adjuvanted with aluminum salts, trehalose was added into the Engerix-B vaccine to a final concentration of 2% (w/v) without further dilution, and the preparation was then subjected to TFFD. Shown in FIGS. 27G-H are representative microscopic images of the Engerix-B vaccine before (FIG. 27G) and after it was subjected to TFFD and reconstitution (FIG. 27H). The particle size of the Engerix-B after it was subjected to TFFD and reconstitution was 3.29±0.15 μm, and particle size of the fresh Engerix-B vaccine was 5.64±0.01 μm. Clearly, the subjecting the Engerix-B vaccine to TFFD and reconstition did not cause any significant aggregation. Therefore, it is likely that the TFFD method can be used to convert any vaccines that contain aluminum salts into dry powder.

40. The Preparation of a Dry Vaccine by Thin Film Freezing

Described herein is a method to produce stable dry vaccines. The method is herein referred to as thin film freezing (TFF). In TFF, liquid droplets fall from a given height and impact, spread, and freeze on a cooled solid substrate. In embodiments, the droplet falls from a given height, and impacts a spinning surface that has a temperature of 223 K. As the droplet spreads out, a freezing front is formed in advance of the unfrozen liquid. In embodiments, the size of the completely frozen droplet is about 2-12 mm in diameter (e.g. 2, 4, 6, 8, 10, or 12 mm), with a height of approximately 50 to 500 μm (e.g. 100, 200, 300, 400, or 500). In embodiments, the liquid droplets (~2-4 mm in diameter) are dispensed from a pipet above a cryogenically cooled metal surface. In embodiments, upon impact, the droplets spread out into thin films (~100-400 μm) that freeze on time scales of 70 to 1000 ms, which corresponds to a cooling rate of ~$10^2$ K/s. Liquid vaccines are passed at a flow rate of 4 mL/min either through a 17 gauge (1.1 mm ID, 1.5 mm OD) stainless steel syringe needle producing 3.6 mm diameter droplets or through 3.9 mm ID, 6.4 mm OD stainless steel tubing producing 5.6 mm diameter droplets. The droplets fall from a height of 10 cm above a rotating stainless steel drum 17 cm long and 12 cm in diameter. The stainless steel drum is hollow with 0.7 cm thick walls and is filled with dry ice or liquid nitrogen to maintain drum surface temperatures of 223 K or 133 K, respectively. Before each run, the surface temperature of the drum is verified with a DiGi-Sense® Type K thermometer using a 45° angle surface probe thermocouple attachment (Eutech Instruments). The drum rotates at approximately 12 rpm and is powered by a Heidolph RZR2041 mechanical overhead stirrer (ESSLAB) connected to a speed reducer. On impact the droplets deform into thin films and freeze. The frozen thin films are removed from the drum by a stainless steel blade mounted along the rotating drum surface. The frozen thin films then fall 5 cm into a 400 mL Pyrex® beaker filled with liquid nitrogen. A Virtis Advantage Lyophilizer (The Virtis Company, Inc.) is used to dry the frozen thin films. The 400 mL beakers containing the frozen thin films are covered with a single layer Kim-wipe. Primary drying is carried out at −40° C. for 36 hrs at 300 mTorr and secondary drying at 25° C. for 24 hrs at 100 mTorr. A 12 hour linear ramp of the shelf temperature from −40° C. to +25° C. is used at 100 mTorr.

In the present study, we synthesized aluminum hydroxide nanoparticles with a mean diameter of 112 nm and showed that the adjuvant activity of the aluminum hydroxide nanoparticles was more potent than that of the traditional aluminum hydroxide microparticles. The specific antibody responses induced by protein antigens adsorbed on aluminum hydroxide nanoparticles were stronger and more durable than that induced by the same amount of antigens adsorbed on the traditional aluminum hydroxide microparticles. The more potent adjuvant activity of the aluminum hydroxide nanoparticles may be partially attributed to their ability to more extensively bind to antigens and increase the uptake of the protein antigens adsorbed on them by APCs. Moreover, the aluminum hydroxide nanoparticles induced milder local inflammatory reactions in the injection sites than the microparticles. Therefore, the new aluminum hydroxide nanoparticles have the potential to be developed in an effective adjuvant to develop new vaccines and to reformulate existing vaccines.

Vaccines that are adjuvanted with aluminum salts, aluminum hydroxide, aluminum phosphate, or aluminum potassium sulfate, can be successfully converted from a liquid suspension into a dried powder by thin-film freeze drying using a low concentration of trehalose (2%, w/v) as an excipient, while maintaining the particle size and the immunogenicity of the vaccines. It is expected that this thin-film freeze drying method can be used to formulate new vaccines or to reformulate existing vaccines that are adjuvanted with aluminum salts into dry powder.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for preparing a thin film antigen composition comprising:
   applying a liquid solvent comprising an antigenic protein and an aluminum salt adjuvant directly to a solid freezing surface, wherein the liquid solvent is in the form of droplets at about 0.1 to 5 mm in diameter; and
   allowing said liquid solvent to disperse and freeze on said solid freezing surface, thereby forming a thin film antigen composition on said solid freezing surface,
   wherein the freezing rate is between 10 K/second and $10^3$ K/second.

2. The method of claim 1, wherein said aluminum salt adjuvant comprises aluminum hydroxide, aluminum phosphate, aluminum sulfate, or aluminum potassium sulfate.

3. The method of claim 1, wherein said liquid solvent comprises about 0.5% to 5% (wt/vol) of an aluminum adjuvant/liquid composition.

4. The method of claim 1, wherein said liquid solvent comprises an excipient.

5. The method of claim 1, wherein said liquid solvent comprises about 0.5% to 5% (wt/vol) of an excipient/liquid composition.

6. The method of claim 1, wherein said allowing said liquid solvent to disperse comprises spraying or dripping droplets of said liquid solvent onto said solid freezing surface.

7. The method of claim 6, wherein the droplet vapor-liquid interfaces of said droplets are less than 500 $cm^{-1}$ area/volume.

8. The method of claim 1, wherein a temperature differential of at least 30° C. between the droplets and the solid freezing surface is present.

9. The method of claim 1, further comprising removing the solvent from the thin film to form a dry composition.

10. The method of claim 1, wherein at least 90% of said antigenic protein is not denatured.

11. The method of claim 10, wherein said aluminum salt adjuvant is aluminum hydroxide, aluminum phosphate or aluminum sulfate.

12. The method of claim 9, wherein said dry composition comprises less than 3% water.

13. The method of claim 9, further comprising solvating said dry composition thereby forming a reconstituted liquid composition.

14. The method of claim 13, wherein said reconstituted liquid solvent comprises particles, wherein said particles comprise said antigenic protein adsorbed to said aluminum salt adjuvant.

15. The method of claim 14, wherein at least 60% of the immunogenicity of said antigen protein in said reconstituted liquid solvent is maintained.

16. The method of claim 1, wherein at least 75% of said antigenic protein is adsorbed to said aluminum salt adjuvant.

17. The method of claim 14, wherein said particles have an average diameter of between 10 nm and 1 μm or between 1 μm and 50 μm, and without significant particle aggregation.

18. The method of claim 1, wherein said thin film antigen composition has a thickness of less than 500 micrometers.

19. The method of claim 1, wherein said thin film antigen composition has a thickness of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 micrometers.

* * * * *